US010689447B2

(12) United States Patent
Elliott et al.

(10) Patent No.: US 10,689,447 B2
(45) Date of Patent: Jun. 23, 2020

(54) FC VARIANTS AND METHODS FOR THEIR PRODUCTION

(71) Applicant: Genentech, Inc., South San Francisco, CA (US)

(72) Inventors: J. Michael Elliott, Half Moon Bay, CA (US); Justin Scheer, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/958,318

(22) Filed: Aug. 2, 2013

(65) Prior Publication Data

US 2014/0079689 A1    Mar. 20, 2014

Related U.S. Application Data

(63) Continuation of application No. PCT/US2012/023749, filed on Feb. 3, 2012.

(60) Provisional application No. 61/439,750, filed on Feb. 4, 2011.

(51) Int. Cl.
| C07K 16/30 | (2006.01) |
| C07K 14/705 | (2006.01) |
| C07K 19/00 | (2006.01) |
| C07K 16/28 | (2006.01) |
| C07K 16/24 | (2006.01) |
| C07K 16/46 | (2006.01) |

(52) U.S. Cl.
CPC ........ *C07K 16/2863* (2013.01); *C07K 16/244* (2013.01); *C07K 16/247* (2013.01); *C07K 16/468* (2013.01)

(58) Field of Classification Search
None
See application file for complete search history.

(56) References Cited

U.S. PATENT DOCUMENTS

| 3,773,919 A | 11/1973 | Boswell et al. |
| 3,896,111 A | 7/1975 | Kupchan et al. |
| 4,120,649 A | 10/1978 | Schechter |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,601,978 A | 7/1986 | Karin |
| 4,657,866 A | 4/1987 | Kumar |
| 4,665,077 A | 5/1987 | Stringfellow et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 4,975,278 A | 12/1990 | Senter et al. |
| 5,053,394 A | 10/1991 | Ellestad et al. |
| 5,114,721 A | 5/1992 | Cohen et al. |
| 5,122,469 A | 6/1992 | Mather et al. |
| 5,143,844 A | 9/1992 | Abrahmsen et al. |
| 5,208,020 A | 5/1993 | Chari et al. |
| 5,264,365 A | 11/1993 | Georgiou et al. |
| 5,362,852 A | 11/1994 | Geoghegan |

(Continued)

FOREIGN PATENT DOCUMENTS

| CN | 101089990 B | 1/2008 |
| EP | 0 340 109 B1 | 11/1989 |

(Continued)

OTHER PUBLICATIONS

Paul, Fundamental Immunology, 3rd Edition, 1993, pp. 292-295.*

(Continued)

*Primary Examiner* — Michael Allen
(74) *Attorney, Agent, or Firm* — McNeill Baur PLLC

(57) ABSTRACT

Described herein are Fc variants and methods for the efficient production of antibodies and other multimeric protein complexes (collectively referred to herein as heteromultimeric proteins). Heteromultimeric proteins may be capable of specifically binding to more than one target. The targets may be, for example, different epitopes on a single molecule or located on different molecules. The methods combine efficient, high gene expression level, appropriate assembly, and ease of purification for the heteromultimeric proteins. The invention also provides methods of using these heteromultimeric proteins, and compositions, kits and articles of manufacture comprising these antibodies.

26 Claims, 20 Drawing Sheets

Specification includes a Sequence Listing.

(56) References Cited

U.S. PATENT DOCUMENTS

| | | |
|---|---|---|
| 5,416,064 A | 5/1995 | Chari et al. |
| 5,500,362 A | 3/1996 | Robinson et al. |
| 5,508,192 A | 4/1996 | Georgiou et al. |
| 5,591,828 A | 1/1997 | Bosslet et al. |
| 5,635,483 A | 6/1997 | Pettit et al. |
| 5,639,635 A | 6/1997 | Joly et al. |
| 5,641,870 A | 6/1997 | Rinderknecht et al. |
| 5,648,237 A | 7/1997 | Carter |
| 5,663,149 A | 9/1997 | Pettit et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,821,337 A | 10/1998 | Carter et al. |
| 5,844,093 A | 12/1998 | Kettleborough et al. |
| 5,877,296 A | 2/1999 | Hamann et al. |
| 6,027,888 A | 2/2000 | Georgiou et al. |
| 6,083,715 A | 7/2000 | Georgiou et al. |
| 6,331,415 B1 | 12/2001 | Cabilly et al. |
| 6,358,509 B1 | 3/2002 | Ramanthan et al. |
| 6,534,628 B1 | 3/2003 | Nilsson et al. |
| 6,660,843 B1 | 12/2003 | Feige et al. |
| 6,835,809 B1 | 12/2004 | Liu et al. |
| 6,919,426 B2 | 7/2005 | Boone et al. |
| 6,979,556 B2 | 12/2005 | Simmons et al. |
| 7,183,076 B2 | 2/2007 | Arathoon et al. |
| 7,472,724 B2 | 1/2009 | Lester et al. |
| 7,498,420 B2 | 3/2009 | Michaud et al. |
| 7,501,121 B2 | 3/2009 | Tchistiakova et al. |
| 7,612,181 B2 | 11/2009 | Wu et al. |
| 7,615,213 B2 | 11/2009 | Kasaian et al. |
| 7,642,228 B2 | 1/2010 | Carter et al. |
| 7,674,459 B2 | 3/2010 | Fung et al. |
| 2002/0004587 A1 | 1/2002 | Miller et al. |
| 2003/0078385 A1 | 4/2003 | Arathoon et al. |
| 2003/0176352 A1 | 9/2003 | Min et al. |
| 2003/0195156 A1 | 10/2003 | Min et al. |
| 2003/0229023 A1 | 12/2003 | Oliner et al. |
| 2003/0236193 A1 | 12/2003 | Oliner et al. |
| 2004/0018198 A1* | 1/2004 | Gudas .............. C07K 16/30 424/155.1 |
| 2004/0228845 A1 | 11/2004 | Ildstad |
| 2005/0054832 A1 | 3/2005 | Lazar et al. |
| 2005/0169933 A1 | 8/2005 | Steeves et al. |
| 2005/0186208 A1 | 8/2005 | Fyfe et al. |
| 2005/0238649 A1 | 10/2005 | Doronina et al. |
| 2006/0121032 A1* | 6/2006 | Dahiyat ............. C07K 16/00 424/144.1 |
| 2006/0173170 A1 | 8/2006 | Chamberlain et al. |
| 2006/0204493 A1* | 9/2006 | Huang .............. C07K 16/00 424/133.1 |
| 2007/0122403 A1 | 5/2007 | Dall'Acqua et al. |
| 2007/0178552 A1 | 8/2007 | Arathoon et al. |
| 2008/0241160 A1 | 10/2008 | Carballido Herrera et al. |
| 2008/0274114 A1 | 11/2008 | Beidler et al. |
| 2009/0182127 A1 | 7/2009 | Kjaergaard et al. |
| 2009/0214523 A1 | 8/2009 | Fung et al. |
| 2009/0215991 A1 | 8/2009 | Lazar et al. |
| 2010/0098730 A1 | 4/2010 | Lowman et al. |
| 2010/0174053 A1* | 7/2010 | Johnson ............ C07K 16/283 530/389.7 |
| 2010/0184959 A1* | 7/2010 | Guler-Gane ........ C07K 16/00 530/387.3 |
| 2011/0039729 A1* | 2/2011 | Delisa .............. C07K 16/1278 506/10 |
| 2011/0123532 A1* | 5/2011 | Gurney et al. ............. 424/136.1 |
| 2012/0148580 A1* | 6/2012 | Chennamsetty ........................... A61K 47/48384 424/133.1 |
| 2014/0294810 A1 | 10/2014 | Lowman et al. |

FOREIGN PATENT DOCUMENTS

| | | |
|---|---|---|
| EP | 0 404 097 B1 | 12/1990 |
| EP | 0 425 235 B1 | 5/1991 |
| EP | 1 391 213 A1 | 2/2004 |
| EP | 2 248 829 A1 | 11/2010 |
| RU | 2326127 C | 6/2008 |
| WO | WO-87/00195 A1 | 1/1987 |
| WO | WO-90/03430 A1 | 4/1990 |
| WO | WO-90/08187 A1 | 7/1990 |
| WO | WO-90/11294 A1 | 10/1990 |
| WO | WO-91/01133 A1 | 2/1991 |
| WO | WO-93/11161 A1 | 6/1993 |
| WO | WO-93/21232 A1 | 10/1993 |
| WO | WO-94/11026 A2 | 5/1994 |
| WO | WO-94/11026 A4 | 5/1994 |
| WO | WO-96/27011 A1 | 9/1996 |
| WO | WO-97/34631 A1 | 9/1997 |
| WO | 98/50431 A2 | 11/1998 |
| WO | WO-98/50431 A2 | 11/1998 |
| WO | WO-98/50431 A3 | 11/1998 |
| WO | WO-00/24770 A2 | 5/2000 |
| WO | WO-00/24770 A3 | 5/2000 |
| WO | WO-00/24770 A9 | 5/2000 |
| WO | WO-00/29004 A1 | 5/2000 |
| WO | WO-00/42072 A2 | 7/2000 |
| WO | WO-02/051870 A2 | 7/2002 |
| WO | WO-02/051870 A3 | 7/2002 |
| WO | WO-02/060919 A2 | 8/2002 |
| WO | WO-02/088172 A2 | 11/2002 |
| WO | WO-02/088172 A3 | 11/2002 |
| WO | WO-02/088172 C1 | 11/2002 |
| WO | WO-02/092620 A2 | 11/2002 |
| WO | WO-02/092620 A3 | 11/2002 |
| WO | WO-03/031589 A2 | 4/2003 |
| WO | WO-03/031589 A8 | 4/2003 |
| WO | WO-03/035694 A2 | 5/2003 |
| WO | WO-03/035694 A3 | 5/2003 |
| WO | WO-03/057134 A2 | 7/2003 |
| WO | WO-03/057134 A3 | 7/2003 |
| WO | WO-03/057134 C1 | 7/2003 |
| WO | WO-2004/026329 A1 | 4/2004 |
| WO | WO-2004/029207 A2 | 4/2004 |
| WO | WO-2004/029207 A3 | 4/2004 |
| WO | WO-2004/056312 A2 | 7/2004 |
| WO | WO-2004/056312 A3 | 7/2004 |
| WO | WO-2004/092215 A2 | 10/2004 |
| WO | WO-2004/092215 A3 | 10/2004 |
| WO | WO-2005/035572 A2 | 4/2005 |
| WO | WO-2005/035572 A3 | 4/2005 |
| WO | WO-2005/063816 A2 | 7/2005 |
| WO | WO-2005/063816 A3 | 7/2005 |
| WO | WO-2006/019447 A1 | 2/2006 |
| WO | WO-2006/028936 A2 | 3/2006 |
| WO | WO-2006/028936 A3 | 3/2006 |
| WO | WO-2006/031370 A2 | 3/2006 |
| WO | WO-2006/053301 A2 | 5/2006 |
| WO | WO-2006/085938 A2 | 8/2006 |
| WO | WO-2006/085938 A3 | 8/2006 |
| WO | WO-2007/147901 A1 | 12/2007 |
| WO | WO-2008/114011 A2 | 9/2008 |
| WO | WO-2008/114011 A3 | 9/2008 |
| WO | WO-2009/058492 A2 | 5/2009 |
| WO | WO-2009/086320 A2 | 7/2009 |
| WO | WO-2009/089004 A1 | 7/2009 |
| WO | WO 2009155513 * | 12/2009 |
| WO | WO-2010/045193 A1 | 4/2010 |
| WO | 2010115589 A | 10/2010 |
| WO | WO 2010/115589 A1 | 10/2010 |
| WO | WO-2012/106587 A1 | 8/2012 |

(56) References Cited

OTHER PUBLICATIONS

Bendig M. M. (Methods: A Companion to Methods in Enzymology, 1995; 8:83-93).*
Higel (European Journal of Pharmaceutics and Biopharmaceutics, vol. 100, p. 94-100, 2016) (Year: 2016).*
Raju (Current Opinion in Immunology, vol. 20, p. 471-478, 2008) (Year: 2008).*
Toyama (Analytical Chemistry, vol. 84, p. 9655-9662, 2012) (Year: 2012).*
Arie et al., "Chaperone function of FkpA, a heat shock prolyl isomerase, in the periplasm of *Escherichia coli*" *Mol Microbiol* 39(1):199-210 (2001).
Bachmann, "Derivations and Genotypes of Some Mutant Derivatives of *Escherichia coli* K-12." *Escherichia coli* and *Salmonella typhimurium*: Cellular and Molecular Biology. (Washington, DC: American Society for Microbiology.), Chapter 72, 2:1190-1219 (1987).
Baldwin et al., "Treatment of Cancer. Monoclonal Antibodies in Cancer Treatment" *The Lancet* 1:603-605 (Mar. 15, 1986).
Barnes and Sato, "Methods for growth of cultured cells in serum-free medium" *Analytical Biochem*. 102:255-270 (1980).
Bass et al., "Hormone Phage: An Enrichment Method for Variant Proteins with Altered Binding Properties" *Proteins* 8(4):309-314 (1990).
Berg et al., "Bispecific antibodies that mediate killing of cells infected with human immunodeficiency virus of any strain" *Proc. Natl. Acad. Sci. USA* 88:4723-4727 (Jun. 1991).
Bostrom et al., "Variants of the antibody herceptin that interact with HER2 and VEGF at the antigen binding site" *Science* 323:1610-1614 (Mar. 2009).
Bothmann and Pluckthun, "The periplasmic *Escherichia coli* peptidylprolyl cis,trans-isomerase FkpA" *J Biol. Chem*. 275(22):17100-17105 (Jun. 2, 2000).
Capel et al., "Heterogeneity of human IgG Fc receptors" *Immunomethods* 4:25-34 (1994).
Carlsson et al., "Protein thiolation and reversible protein-protein conjugation" *Biochem J* 173:723-737 (1978).
Chamow et al., "A humanized, bispecific immunoadhesin-antibody that retargets CD3+ effectors to kill HIV-1-infected cells" *J Hematotherapy* 4:439-446 (1995).
Chari et al., "Immunoconjugates containing novel maytansinoids: Promising anticancer drugs" *Cancer Res* 52:127-131 (1992).
Chen et al., "Chaperone Activity of DsbC" *J Biol Chem* 274(28):19601-19605 (Jul. 1999).
Chen et al., "Selection and analysis of an optimized anti-VEGF antibody: Crystal structure of an affinity-matured Fab in complex with antigen" *J Mol Biol* 293:865-881 (1999).
Chothia, "The Nature of the Accessible and Buried Surfaces in Proteins" *Journal Mol. Biol*. 105:1-14 (1976).
Clackson et al., "Making antibody fragments using phage display libraries" *Nature* 352(6336):624-628 (Aug. 15, 1991).
Clynes et al., "Fc receptors are required in passive and active immunity to melanoma" *Proc. Natl. Acad. Sci. USA* 95(2):652-656 (Jan. 1998).
Daeron, "Fc receptor biology" *Annu Rev Immunol* 15:203-234 (1997).
Davies and Riechmann, "'Camelising' human antibody fragments: NMR studies on VH domains" *Febs Lett* 339:285-290 (1994).
De Haas et al., "Fcγ receptors of phagocytes" *J Lab Clin Med* 126:330-341 (Oct. 1995).
Dooley and Flajnik, "Antibody repertoire development in cartilaginous fish" *Developmental and Comparative Immunol* 30:43-56 (2006).
Doronina et al., "Development of potent monoclonal antibody auristatin conjugates for cancer therapy" *Nat Biotechnol* 21(7):778-784 (Jul. 2003).
Ellman et al., "Biosynthetic method for introducing unnatural amino acids site-specifically into proteins" *Meth Enzym* 202:301-336 (1991).

Fischer and Leger, "Bispecific antibodies: Molecules that enable novel therapeutic strategies" *Pathobiology* 74:3-14 (2007).
Fowlis et al., "Experimental and theoretical analysis of the rate of solvent equilibration in the hanging drop method of protein crystal growth" *Journal of Crystal Growth* 90(1-3):117-129 (Jul. 2, 1988).
Fraker and Speck, "Protein and cell membrane iodinations with a sparingly soluble chloroamide, 1,3,4,6-tetrachloro-3a,6a-diphenylglycoluril" *Biochem Bioph Res Co* 80(4):849-857 (1978).
Gazzano-Santoro et al., "A non-radioactive complement-dependent cytotoxicity assay for anti-CD20 monoclonal antibody" *J Immunol Methods* 202(2):163-171 (Mar. 28, 1997).
Geoghegan and Stroh, "Site-directed conjugation of nonpeptide groups to peptides and proteins via periodate oxidation of a 2-amino alcohol. Application to modification at N-terminal serine" *Bioconjugate Chem*. 3:138-146 ( 1992).
Graham et al., "Characteristics of a human cell line transformed by DNA from human adenovirus type 5" *J Gen Virol* 36(1):59-72 (Jul. 1977).
Gronwall et al., "Generation of Affibody® ligands binding interleukin-2 receptor α/CD25" *Biotechnol Appl Biochem* 50:97-112 (2008).
Guss et al., "Structure of the IgG-binding regions of streptococcal protein G" *Embo J* 5(7):1567-1575 (1986).
Guyer et al., "Immunoglobulin binding by mouse intestinal epithelial cell receptors" *J Immunol* 117(2):587-593 (Aug. 1976).
Ham and McKeehan, "Media and Growth Requirements" *Method Enzymol*. 58:44-93 (1979).
Hara et al., "Overproduction of Penicillin-Binding Protein 7 Suppresses Thermosensitive Growth Defect at Low Osmolarity Due to an spr Mutation of *Escherichia coli*" *Microb Drug Resist* 2(1):63-72 (1996).
Hinman et al., "Preparation and characterization of monoclonal antibody conjugates of the calicheamicins: A novel and potent family of antitumor antibiotics" *Cancer Res* 53:3336-3342 (1993).
Holliger et al., "Diabodies: Small Bivalent and Bispecific Antibody Fragments" *Proc. Natl. Acad. Sci. USA* 90:6444-6448 (Jul. 1993).
Holt et al., "Domain antibodies: proteins for therapy" *Trends Biotechnol* 21(11):484-490 (Nov. 2003).
Humphreys et al., "F(ab')$_2$ molecules made from *Escherichia coli* produced Fab' with hinge sequences conferring increased serum survival in an animal model" *J Immunol Methods* 217:1-10 (1998).
Janeway, C., "Immunotherapy by peptides?" *Nature* 341:482-483 (Oct. 12, 1989).
Jin et al., "MetMAb, the One-armed 5D5 anti-c-Met antibody, inhibits orthotopic pancreatic tumor growth and improves survival" *Cancer Res* 68(11):4360-8 (Jun. 2008).
Joly et al., "Overexpression of *Escherichia coli* Oxidoreductases Increases Recombinant Insulin-Like Growth Factor-I Accumulation" *Proc. Natl. Acad. Sci. USA* 95:2773-2777 (Mar. 1998).
Jones et al. "Replacing the complementarity-determining regions in a human antibody with those from a mouse," *Nature* 321:522-525 (May 29, 1986).
Kabat et al. Sequences of Proteins of Immunological Interest (Table of Contents, Introduction and Constant Region Sequences sections), 5th edition, Bethesda, MD:NIH, vol. 1:647-723 (1991).
Kim et al., "Localization of the site of the murine IgG1 molecule that is involved in binding to the murine intestinal Fc receptor" *Eur J Immunol* 24(10):2429-2434 (Oct. 1994).
Kindt et al. Kuby Immunology "Antigens and Antibodies Chapter 4" 6th edition, N.Y.W.H. Freeman and Co, p. 91 (2007).
Kontermann,, "Recombinant bispecific antibodies for cancer therapy" *Acta Pharmacologica Sinica* 26(1):1-9 (Jan. 2005).
Lee and Kwak, "Expression and functional reconstitution of a recombinant antibody (Fab') specific for human apolipoprotein B-100" *J Biotechnol* 101:189-198 (2003).
Lee et al., "Characterization of the gene encoding heat-stable toxin II and preliminary molecular epidemiological studies of enterotoxigenic *Escherichia coli* heat-stable toxin II producers" *Infect Immun* 42:264-268 (Oct. 1983).
Lindmark et al., "Binding of immunoglobulins to protein A and immunoglobulin levels in mammalian sera" *J Immunol Methods* 62:1-13 (1983).

(56) References Cited

OTHER PUBLICATIONS

Liu et al., "Eradication of large colon tumor xenografts by targeted delivery of maytansinoids" *Proc. Natl. Acad. Sci. USA* 93:8618-8623 (Aug. 1996).
Lode et al., "Targeted therapy with a novel enediyene antibiotic calicheamicin θ$^I$ effectively suppresses growth and dissemination of liver metastases in a syngeneic model of murine neuroblastoma" *Cancer Res* 58:2925-2928 (1998).
Malmborg and Borrebaeck, "BIAcore as a tool in antibody engineering" *J Immunol Methods* 183:7-13 ( 1995).
Mandler et al., "Immunoconjugates of geldanamycin and Anti-HER2 monoclonal antibodies: antiproliferative activity on human breast carcinoma cell lines" *J National Cancer Institute* 92(19):1573-1581 (Oct. 4, 2000).
Mandler et al., "Modifications in synthesis strategy improved the yield and efficacy of geldanamycin-herceptin immunoconjugates" *Bioconjugate Chem* 13:786-791 (2002).
Mandler et al., "Synthesis and Evaluation of Antiproliferative Activity of a Geldanamycin-Herceptin(tm) Immunoconjugate" *Bioorg Med Chem Lett* 10:1025-1028 (2000).
Martens et al., "A novel one-armed anti-c-Met antibody inhibits glioblastoma growth in vivo" *Clin Cancer Res* 12(20):6144-6152 (Oct. 2006).
Marvin and Zhu, "Bispecific antibodies for dual-modality cancer therapy: killing two signaling cascades with one stone" *Curr Opin Drug Discov Devel* 9(2):184-193 (2006).
Marvin and Zhu. "Recombinant approaches to IgG-like bispecific Antibodies," *Acta Pharmacologica Sinica* 26(6):649-658, (Jun. 2005).
Mather et al., "Culture of testicular cells in hormone-supplemented serum-free medium" *Ann NY Acad Sci* 383:44-68 (1982).
Mather, "Establishment and characterization of two distinct mouse testicular epithelial cell lines" *Biol. Reprod.* 23:243-252 (1980).
Morrison et al., "Chimeric human antibody molecules: Mouse antigen-binding domains with human constant region domains" *Proc. Natl. Acad. Sci. USA* 81:6851-6855 (Nov. 1984).
Murakami et al., "Cell Cycle Regulation, Oncogenes, and Antineoplastic Drugs" The Molecular Basis of Cancer., Mendelsohn and Israel, eds, Philadelphia:WB Saunders, Chapter 1, pp. 3-17 (1995).
Muyldermans et al., "Recognition of antigens by single-domain antibody fragments: the superfluous luxury of paired domains" *Trends Biochem SCI* 26(4):230-235 (Apr. 2001).
Nicolaou et al., "Calicheamicin θ$^I_1$: A rationally designed molecule with extremely potent and selective DNA cleaving properties and apoptosis Inducing activity." *Angew Chem Intl Ed Engl* 33(2):183-186 (1994).
Niculescu-Duvaz and Springer, "Antibody-directed enzyme prodrug therapy (ADEPT): a review" *Adv. Drug Deliv. Rev.* 26:151-172 (1997).
Nilsson et al., "A synthetic IgG-binding domain based on staphylococcal protein A" *Protein Eng* 1:107-113 (1987).
Nord et al., "A combinational library of an α-helical bacterial receptor domain" *Protein Eng* 8(6):601-608 (1995).
Nord et al., "Binding proteins selected from combinatorial libraries of an α-helical bacterial receptor domain" *Nature Biotechnol* 15:772-777 (Aug. 1997).
Noren et al., "A general method for site-specific incorporation of unnatural amino acids into proteins" *Science* 244(4901):182-188 (Apr. 14, 1989).
Offner et al., "T cell receptor peptide therapy triggers autoregulation of experimental encephalomyelitis" *Science* 251:430-432 (1991).
Pack et al., "Improved bivalent miniantibodies, with identical avidity as whole antibodies, produced by high cell density fermentation of *Escherichia coli*" *Bio/Technology* 11:1271-1277 (Nov. 1993).
Pack et al., "Miniantibodies: Use of amphipathic helices to produce functional, flexibly linked dimeric $F_v$ fragments with high avidity in *Escherichia coli*" *Biochemistry* 31(6):1579-1584 (1992).

Pettit et al., "Specific activities of dolastatin 10 and peptide derivatives against cryptococcus neoformans" *Antimicrob Agents and Chemotherapy* 42(11):2961-2965 (Nov. 1998).
Pettit et al., "Antineoplastic agents 360. Synthesis and cancer cell growth inhibitory studies of dolastatin 15 structural modifications" *Anticancer Drug Des.* 13(1):47-66 (Jan. 1998).
Pettit et al., "Antineoplastic agents 365. Dolastatin 10 SAR probes" *Anti-Cancer Drug Design* 13:243-277 (1998).
Pettit. "The Dolastatins," Progress in the Chemistry of Organic Natural Products, W. Hertz et al., Springer Wien New York, vol. 70:1-79 (1997).
Pettit et al., "Marine animal biosynthetic constituents for cancer chemotherapy" *J. Nat. Prod.* 44(4):482-485 (Jul. 1981).
Picken et al., "Nucleotide sequence of the gene for heat-stable enterotoxin II of *Escherichia coli*" *Infect Immun* 42(1):269-275 (Oct. 1983).
Pluckthun, A., The Pharmacology of Monoclonal Antibodies: Handbook of Pharmacology "Antibodies from *Escherichia coli*" (Chapter 11), Rosenberg and Moore, eds., Berlin: Springer-Verlag, vol. 113:269-315 ( 1994).
Poncet, "The dolastatins, a family of promising antineoplastic agents" *Curr. Pharm. Des.* 5(3):1369-162 (Mar. 1999).
Ponder and Richards, "Tertiary templates for proteins. Use of packing criteria in the enumeration of allowed sequences for different structural classes" *J Mol Biol.* 193(4):775-791 (Feb. 20, 1987).
Portolano et al., "Lack of promiscuity in autoantigen-specific H and L chain combinations as revealed by human H and L chain 'roulette'" *J Immunol* 150(3):880-7 (Feb. 1, 1993).
Presta, "Antibody Engineering" *Curr Opin Struc Biol* 2:593-596 (1992).
Proba et al., "Functional Antibody Single-Chain Fragments From the Cytoplasm of *Escherichia coli*: Influence of Thioredoxin Reductase (TrxB)" *Gene* 159:203-207 (1995).
Ram and Pluckthun, "The periplasmic *Escherichia coli* peptidylprolyl cis,trans-isomerase FkpA" *J. Biol. Chem.* 275(22):17106-17113 (Jun. 2, 2000).
Ravetch and Kinet, "Fc receptors" *Ann Rev Immunol* 9:457-492 ( 1991).
Ridgway et al., "Identification of a human anti-CD55 single-chain Fv by subtractive panning of a phage library using tumor and nontumor cell lines" *Cancer Res* 59(11):2718-2723 (Jun. 1, 1999).
Riechmann et al., "Reshaping human antibodies for therapy" *Nature* 332:323-327 (Mar. 24, 1988).
Rowland et al., "Drug localisation and growth inhibition studies of vindesine-monoclonal anti-CEA conjugates in a human tumour xenograft" *Cancer Immunol Immunother* 21:183-187 (1986).
Rupert et al., "Cloning and expression of human TAF 250: a TBP-associated factor implicated in cell-cycle regulation" *Nature* 362:175-179 (Mar. 11, 1993).
Schroder and Lubke "The Peptides" Academic Press, vol. 1:76-136 ( 1965).
Siebenlist et al., "*E. coli* RNA Polymerase Interacts Homologously with Two Different Promoters" *Cell* 20:269-281 (Jun. 1980).
Simmons and Yansura, "Translational level is a critical factor for the secretion of heterologous proteins in *Escherichia coli*" *Nat Biotechnol* 14:629-634 (May 1996).
Simmons et al., "Expression of full-length immunoglobulins in *Escherichia coli*: rapid and efficient production of aglycosylated antibodies" *J Immunol. Methods* 263:133-147 (2002).
Starovasnik et al., "Structural mimicry of a native protein by a minimized binding domain" *Proc. Natl. Acad. Sci. USA* 94:10080-10085 (Sep. 16, 1997).
Stella and Himmelstein, "Directed Drug Delivery Prodrugs: A chemical approach to targeted drug delivery" Borchardt et al. Humana Press pp. 247-267 (1985).
Syrigos and Epenetos, "Antibody Directed Enzyme Prodrug Therapy (ADEPT): A Review of the Experimental and Clinical Considerations" *Anticancer Res* 19:605-613 (1999).
Thorpe, "Antibody carriers of cytotoxic agents in cancer therapy: a review" Monoclonal Antibodies '84: Biological and Clinical Applications, (A Pinchera, G. Doria, F. Dammacco and A. Bargellesi, eds. pp. 475-506 (1985).

(56) References Cited

OTHER PUBLICATIONS

Urlaub et al., "Isolation of Chinese hamster cell mutants deficient in dihydrofolate reductase activity" *Proc. Natl. Acad. Sci. USA* 77(7):4216-4220 (Jul. 1980).
Vitetta et al., "Redesigning Nature's Poisons to Create Anti-Tumor Reagents" *Science* 238(4830):1098-1104 (Nov. 20, 1987).
Ward et al., "Binding activities of a repertoire of single immunoglobulin variable domains secreted from *Escherichia coli*" *Nature* 341:544-546 (Oct. 12, 1989).
Wibbenmeyer et al., "Cloning, expression, and characterization of the Fab fragment of the anti-lysozyme antibody HyHEL-5" *Biochimica Et Biophysica Acta* 1430:191-202 ( 1999).
Wilman, D. E. V., Prodrugs in cancer chemotherapy Biochemical Society Transactions, 615th Meeting, Belfast, Ireland, pp. 375-382, vol. 14, (1986).
Woyke et al., "In vitro activities and postantifungal effects of the potent dolastatin 10 derivative auristatin PHE" *Antimicrob Agents Chemother* 45(12):3580-3584 (Dec. 2001).
Yaniv, "Enhancing elements for activation of eukaryotic promoters" *Nature* 297:17-18 (May 6, 1982).
Zamyatnin, "Protein volume in solution" *Prog Biophys Mol. Biol.* 24:107-123 (1972).
Zapata et al., "Engineering linear F(ab')$_2$ fragments for efficient production in *Escherichia coli* and enhanced antiproliferative activity" *Protein Eng* 8(10):1057-1062 (1995).
Zhu et al., "Remodeling domain interfaces to enhance heterodimer formation" *Protein Sci* 6(4):781-788 (Apr. 1997).
Zhu et al., "Tumor localization and therapeutic potential of an antitumor-anti-CD3 heteroconjugate antibody in human renal cell carcinoma xenograft models" *Cancer Letters* 86:127-134 (1994).
Dall' Acqua et al., "Increasing the affinity of a human IgG1 for the neonatal Fc receptor: biological consequences" *J Immunol.* 169(9):5171-5180 (Nov. 1, 2002).
Hinton et al., "An engineered human IgG1 antibody with longer serum half-life" *J Immunol.* 176(1):346-56 (2006).
Martin et al., "Crystal structure at 2.8 A of an FcRn/heterodimeric Fc complex: mechanism of pH-dependent binding" *Molecular Cell* 7(4):867-877 (Apr. 2001).
Petkova et al., "Enhanced half-life of genetically engineered human IgG1 antibodies in a humanized FcRn mouse model: potential application in humorally mediated autoimmune disease" *Int Immunol.* 18(12):1759-69 (Dec. 2006).
Yeung et al., "Engineering Human IgG1 Affinity to Human Neonatal Fc Receptor: Impact of Affinity Improvement on Pharmacokinetics in Primates" *Journal of Immunology* 182:7663-7671 (2009).
Notice of Reasons for Rejection, for Japanese Patent Application No. 2013-552669, dated Jan. 5, 2016, including English translation (10 pages).
Ridgway J.B.B. et al., "'Knobs-into-holes' engineering of antibody CH3 domains for heavy chain heterodimerization." Protein Engineering, Design and Selection, 1996, 9(7): 617-621.
Gunasekaran K. et al. "Enhancing antibody Fc heterodimer formation through electrostatic steering effects: applications to bispecific molecules and monovalent IgG." Journal of Biological Chemistry, 2010, jbc-M110.
Search Report issued in Russian Application No. 2018108836, English translation, 3 pages, dated Feb. 11, 2019.

\* cited by examiner

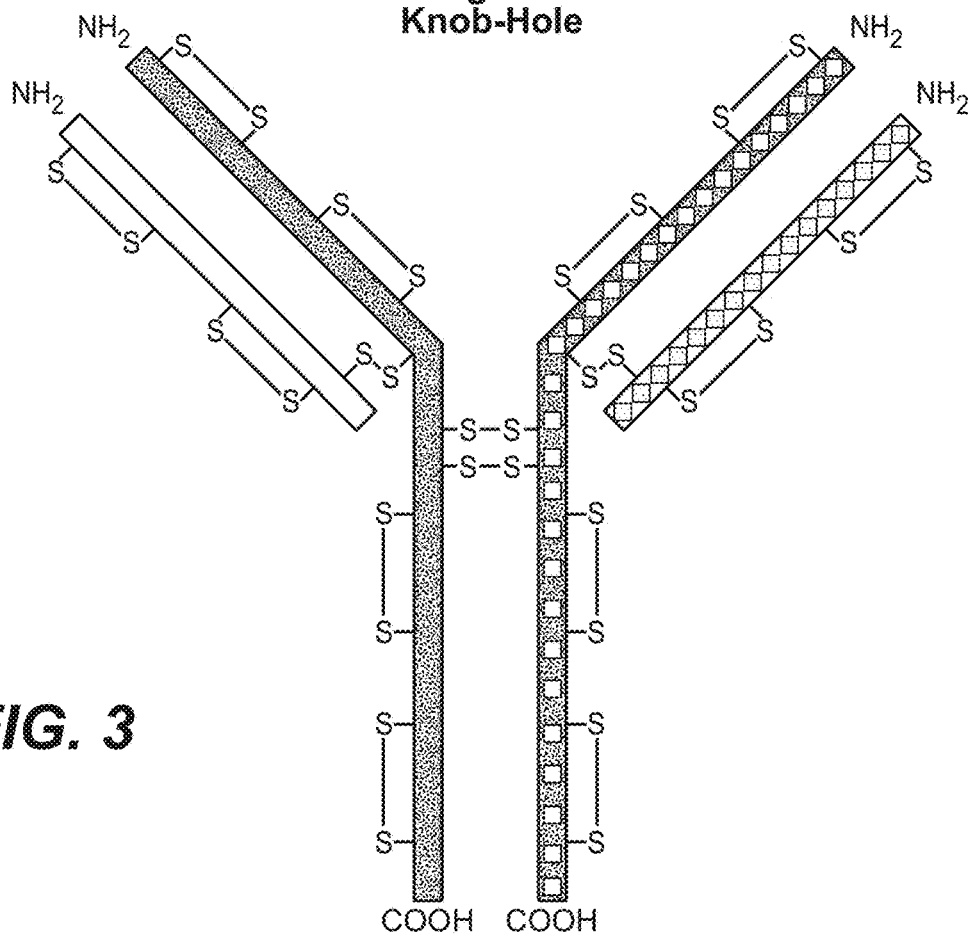
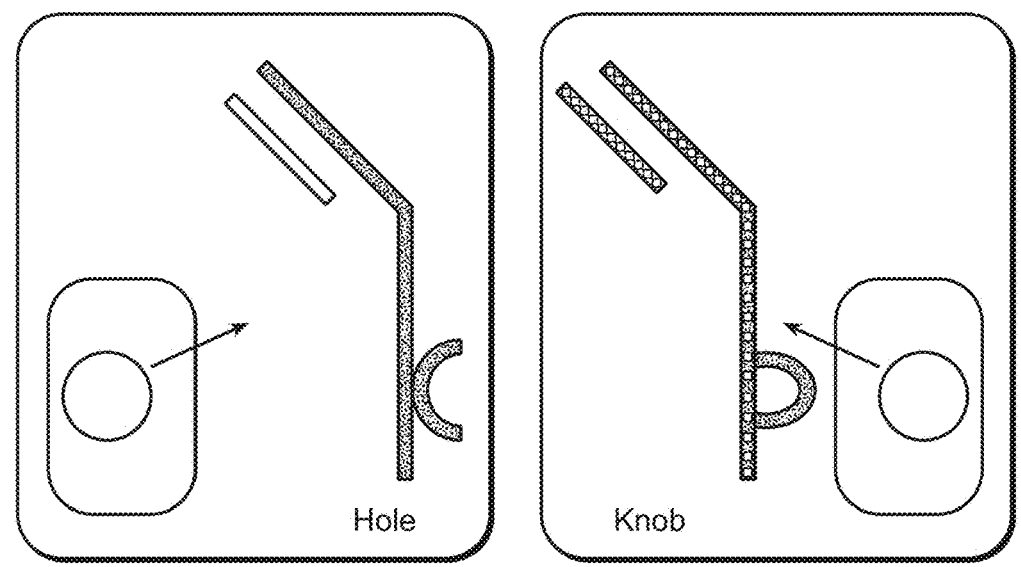
FIG. 3

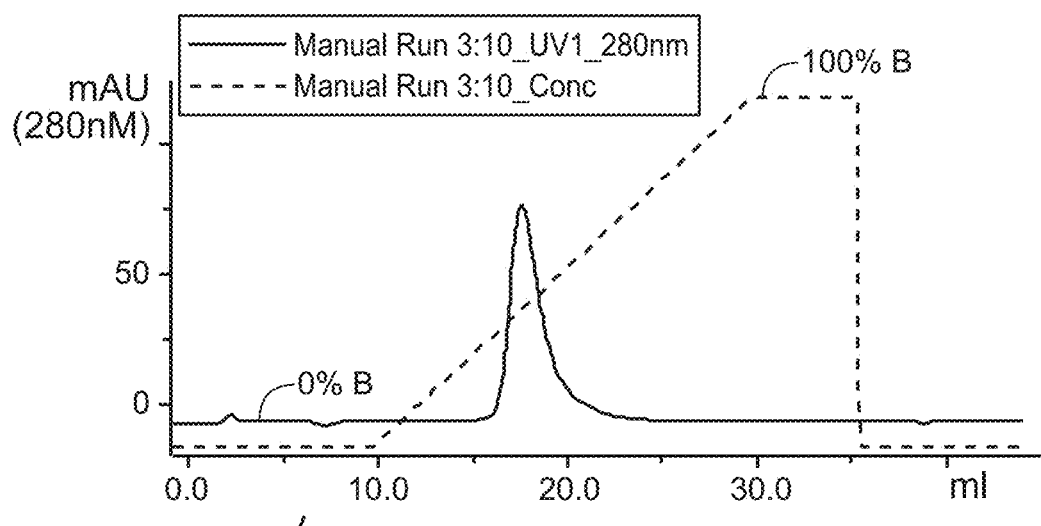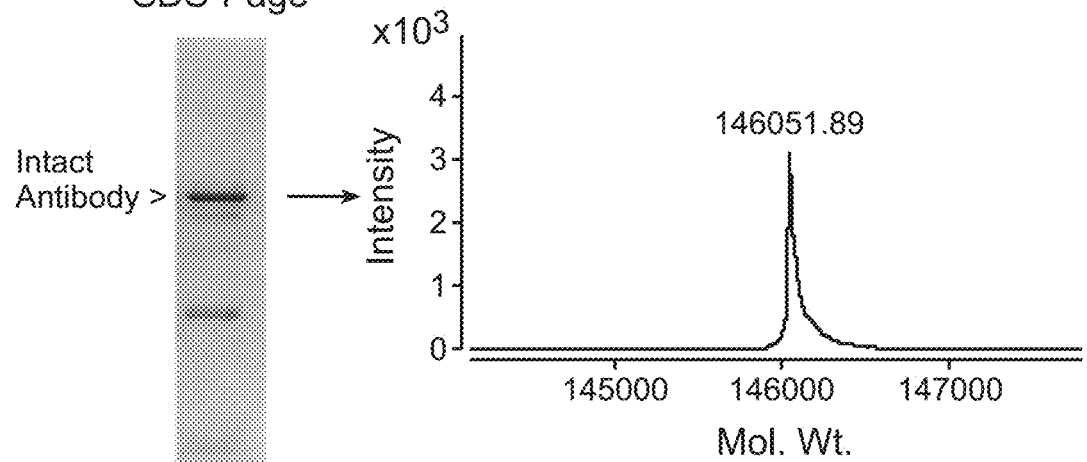
FIG. 4D

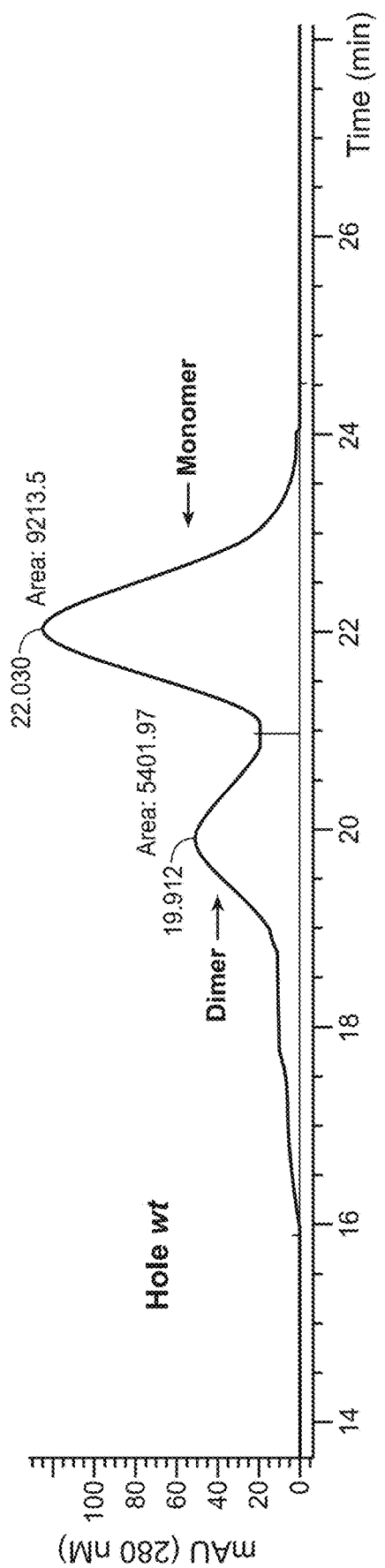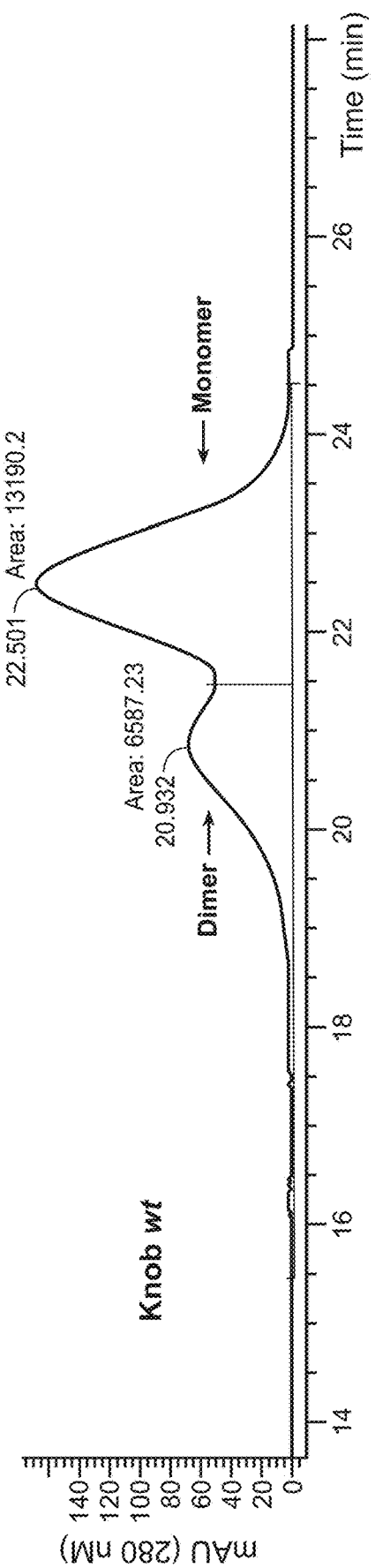

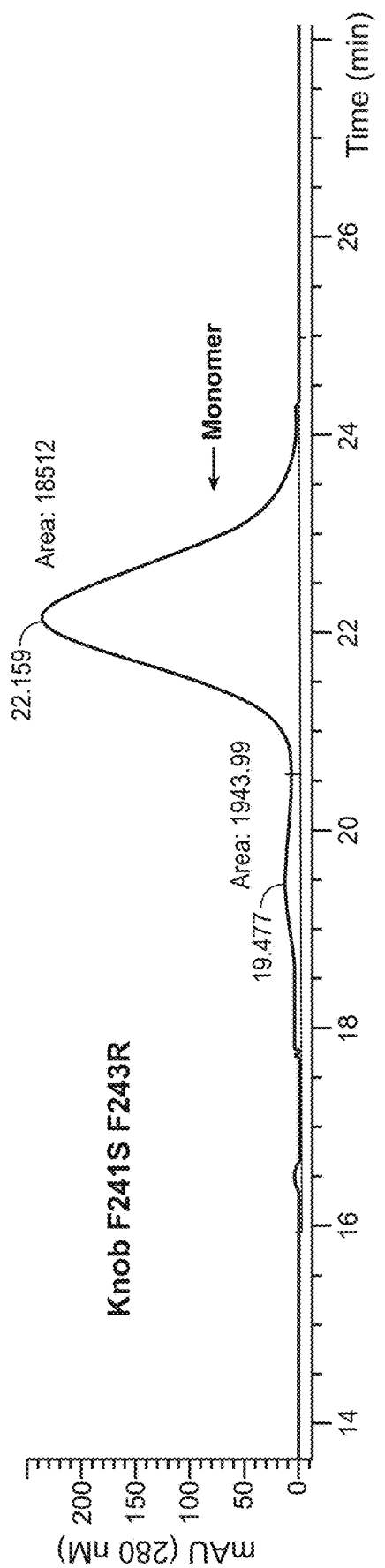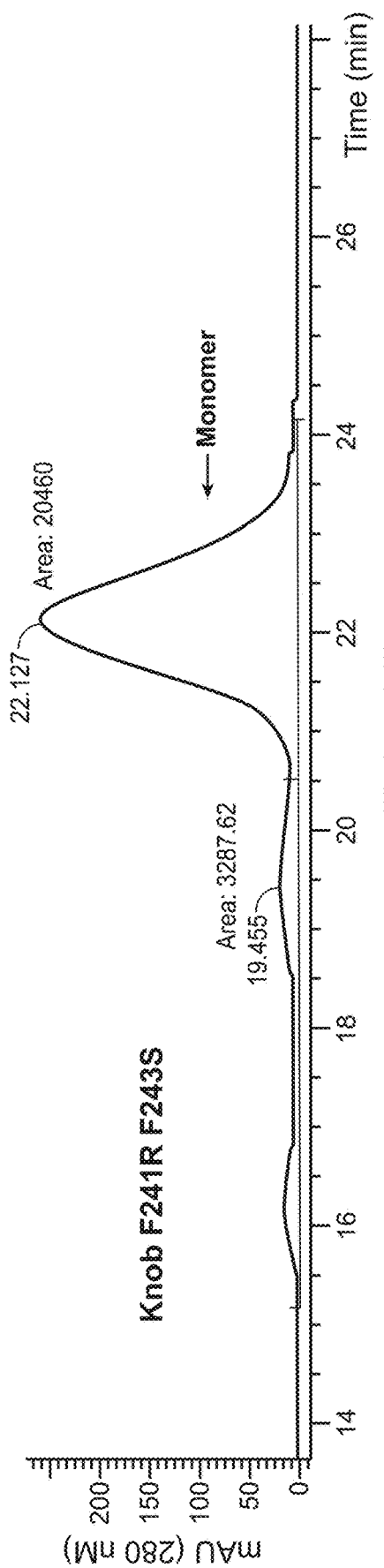

FC VARIANTS AND METHODS FOR THEIR PRODUCTION

CROSS-REFERENCE TO RELATED APPLICATIONS

The present application is a continuation of International Application No. PCT/US2012/023749 having an international filing date of Feb. 3, 2012, the entire contents of which are incorporated herein by reference, and which claims priority to U.S. Provisional Patent Application Ser. No. 61/439,750, entitled "Fc Variants And Methods For Their Production", filed Feb. 4, 2011.

SEQUENCE LISTING

The instant application contains a Sequence Listing submitted via EFS-Web and is hereby incorporated by reference in its entirety. The ASCII text file, created on Aug. 6, 2015, is named 146392014201SEQLIST.txt, and is 9 KB in size.

TECHNICAL FIELD

This invention relates to Fc variants, methods for their generation, and antibodies and Fc fusions comprising Fc variants.

BACKGROUND

Monoclonal antibodies of the IgG type contain two identical antigen-binding arms and a constant domain (Fc). Antibodies with a differing specificity in their binding arms usually do not occur in nature and, therefore, have to be crafted with the help of chemical engineering (e.g., chemical cross-linking, etc), recombinant DNA and/or cell-fusion technology.

Bispecific antibodies can bind simultaneously two different antigens. This property enables the development of therapeutic strategies that are not possible with conventional monoclonal antibodies. The large panel of imaginative bispecific antibody formats that has been developed reflects the strong interest for these molecules. See Berg J, Lotscher E, Steimer K S, et al., "Bispecific antibodies that mediate killing of cells infected with human immunodeficiency virus of any strain," Proc Natl Acad Sci USA (1991) 88(11): 4723-4727 and Fischer N and Leger O., "Biospecific Antibodies: Molecules That Enable Novel Therapeutic Strategies," Pathobiology (2007) 74:3-14.

Another class of multispecific molecules is recombinant fusion proteins. Recombinant fusion proteins consisting of the extracellular domain of immunoregulatory proteins and the constant (Fc) domain of immunoglobulin (Ig) represent a growing class of human therapeutics. Immunoadhesins combine the binding region of a protein sequence, with a desired specificity, with the effector domain of an antibody. Immunoadhesins have two important properties that are significant to their potential as therapeutic agents: the target specificity, and the pharmacokinetic stability (half-life in vivo that is comparable to that of antibodies). Immunoadhesins can be used as antagonist to inhibit or block deleterious interactions or as agonist to mimic or enhance physiological responses. See Chamow S M, Zhang D Z, Tan X Y, et al., "A humanized, bispecific immunoadhesin-antibody that retargets CD3+ effectors to kill HIV-1-infected cells," J Hematother 1995; 4(5): 439-446.

Other multispecific molecules have been discussed elsewhere. Examples include but are not limited to: Fisher et al., Pathobiology (2007) 74:3-14 (review of various bispecific formats); U.S. Pat. No. 6,660,843, issued Dec. 9, 2003 to Feige et al. (peptibodies); US Pat. Publ. No. 2002-004587 published Jan. 10, 2002 (multispecific antibodies); U.S. Pat. No. 7,612,181 issued Nov. 3, 2009 to Wu et al. (Dual Variable Domain format); U.S. Pat. No. 6,534,628, Nord K et al., Prot Eng (1995) 8:601-608, Nord K et al., Nat Biotech (1997) 15:772-777, and Grönwall et al., Biotechnol Appl Biochem. (2008) June; 50(Pt 2):97-112 (Affibodies); Martens et al., Clin Cancer Res (2006), 12: 6144-6152 and Jin et al., Cancer Res (2008) 68(11):4360-4368 (one armed antibodies); Bostrom et al., Science (2009) 323:1610-1614 (Dual Action Fab, aka mixed valency antibodies). Other formats are known to those skilled in the art.

The manufacturing of clinical grade material remains challenging for antibodies generally and especially for the multispecific molecules described above. As noted above, there are many paths to the production of molecules with mixed binding arms, i.e., binding arms that are not identical to each other. Each of these methods has its drawbacks.

Chemical cross-linking is labor intensive as the relevant species may yet need to be purified from homodimers and other undesired by-products. In addition, the chemical modification steps can alter the integrity of the proteins thus leading to poor stability. Thus, this method is often inefficient and can lead to loss of antibody activity.

Cell-fusion technology (e.g., hybrid hybridomas) express two heavy and two light chains that assemble randomly leading to the generation of 10 antibody combinations. The desired heteromultimeric antibodies are only a small fraction of the antibodies thus produced. Purification of the desired heteromultimeric proteins dramatically reduces production yields and increases manufacturing costs.

Recombinant DNA techniques have been used to generate various heteromultimeric formats, e.g., single chain Fv, diabodies, etc., that do not comprise an Fc domain. A major drawback for this type of antibody molecule is the lack of the Fc domain and thus the ability of the antibody to trigger an effector function (e.g., complement activation, Fc-receptor binding etc.). Thus, a bispecific antibody comprising a functional Fc domain is desired.

Recombinant DNA techniques have also been used to generate 'knob into hole' bispecific antibodies. See US Patent Application 20030078385 (Arathoon et al.—Genentech). One constraint of this strategy is that the light chains of the two parent antibodies have to be identical to prevent mispairing and formation of undesired and/or inactive molecules due to being expressed in the same cell.

In addition, the limiting event during annealing and purification is the redox efficiency. Oxidized heterodimer typically only makes up 70-80% of the protein after this step (BioAnalyzer and MS-TOF). The remaining 20-30% of antibody is dimeric and lacks a covalent linkage (SEC-LLS). This can be removed but significantly impacts overall yields. Thus, there remains a need to improve the overall yield in antibody production, especially heterodimers. Described herein are Fc variants that may improve overall yield of antibodies, heterodimers and the like as well as methods for their generation. These and other aspects and advantages of the invention will be apparent from the description of the invention provided herein.

BRIEF SUMMARY OF THE INVENTION

Production of heteromultimeric proteins, e.g., multispecific antibodies, using current techniques has drawbacks including the production of a mixture of products, reduced yield and decreased/elimination of effector function among others. Thus, it is desirable to produce heteromultimeric proteins efficiently and at high levels.

The production of antibody molecules, by various means, is generally well understood. U.S. Pat. No. 6,331,415 (Cabilly et al.), for example, describes a method for the recombinant production of immunoglobulin where the heavy and light chains are expressed simultaneously from a single vector or from two separate vectors in a single cell. Wibbenmeyer et al., (1999, Biochim Biophys Acta 1430(2): 191-202) and Lee and Kwak (2003, J. Biotechnology 101: 189-198) describe the production of monoclonal antibodies from separately produced heavy and light chains, using plasmids expressed in separate cultures of E. coli. Various other techniques relevant to the production of antibodies are described in, e.g., Harlow, et al., ANTIBODIES: A LABORATORY MANUAL, Cold Spring Harbor Laboratory Press, Cold Spring Harbor, N.Y., (1988) and WO2006028936. Yet each of these have draw backs such as low yield, use of chemicals, etc.

Disclosed herein are Fc variants that comprise at least two mutations at amino acid residues that provide a basis for improving overall yields in the production of heteromultimeric proteins.

This invention provides an easy and efficient production process/method that allows for the economical production of heteromultimeric proteins, e.g., multispecific antibodies, which comprise a variant Fc polypeptide.

In a first embodiment, a variant heteromultimeric protein comprising an Fe variant of a wild-type Fe polypeptide is provided. In various embodiments, the Fe variant comprises at least one, two, three, four, five, six, seven, eight, nine or ten amino acid modifications in the Fe region of said wild-type Fe polypeptide resulting in a variant protein that exhibits decreased mispairing (e.g., knob/knob pairing), decreased head-to-tail formation or increased overall yield as compared to the wild-type Fe polypeptide. In some embodiments, it is preferred that the Fe variant comprises two, three or four amino acid modifications capable of disrupting homodimer formation as described herein. In some embodiments, the Fe variant comprises a substitution at residues 241 and 243 on at least one heavy chain with an amino acid which is different from that present in a wild-type Fe polypeptide. In some embodiments, the mutations on at least one heavy chain are selected from F241 RIF243S and F241 S/F243R. In some embodiments, the Fe variant further comprises knob-into-hole modification(s).

In a second embodiment, an isolated nucleic acid encoding the variant heteromultimeric protein or the modified IgG antibody as described herein is provided.

In a third embodiment, an expression vector encoding the variant heteromultimeric protein or the modified IgG antibody as described herein is provided.

In a fourth embodiment, a host cell comprising a nucleic acid molecule or an expression vector comprising the nucleic acid molecule as described herein is provided. In some embodiments, the host cell is a CHO cell. In some embodiments, the host cell is an E. coli cell.

In an embodiment, a method of producing the variant heteromultimeric protein or the modified IgG antibody described herein comprises:
(a) culturing a host cell; and
(b) recovering the variant heteromultimeric protein or the modified IgG antibody from the cell culture.
In some embodiments, the recovery comprises lysing the cells.

In some embodiments, the method of preparing a heteromultimeric protein comprising heteromultimeric protein comprising a first Fc-containing polypeptide having a first heterodimerization domain and a second Fc-containing polypeptide having a second heterodimerization domain, wherein the second heterodimerization domain interacts with the first heterodimerization domain, and wherein the first and second Fc-containing polypeptides are linked by at least one interchain disulfide bond, the method comprising the steps of:
(a) providing a purified first Fc-containing polypeptide having a first heterodimerization domain;
(b) providing a purified second Fc-containing polypeptide having a second heterodimerization domain;
(c) combining the first and second Fc-containing polypeptides;
(d) refolding the first hinge-containing polypeptide with the second hinge-containing polypeptide; and
(e) recovering the heteromultimeric protein complex.

In some embodiments, the first and second Fc-containing polypeptides further comprise mutations that facilitates the proper orientation of the Fc-containing polypeptides relative to each other. In some embodiments, the mutations comprise substitutions at residues 241 and 243 on at least one heavy chain with an amino acid which is different from that present in an wild-type Fc polypeptide.

In an embodiment, there are provided the heteromultimeric proteins produced by the methods described herein.

It is to be understood that methods of the invention can include other steps which generally are routine steps evident for initiating and/or completing the process encompassed by methods of the invention as described herein. For example, in one embodiment, step (a) of a method of the invention is preceded by a step wherein a nucleic acid encoding a Fc variant polypeptide is introduced into a first host cell, and a nucleic acid encoding a second hinge-containing polypeptide is introduced into a second host cell. In one embodiment, methods of the invention further comprise a step of purifying heteromultimeric proteins having binding specificity to at least two distinct targets. In one embodiment, no more than about 10%, 15%, 20% or 30% of isolated polypeptides are present as monomers and/or heavy-light chain dimers prior to the step of purifying the heteromultimeric proteins. In one embodiment, the monomers can be less than about 30% of undesired polypeptide contaminants which need to be removed prior to purifying the heteromultimeric proteins.

In an embodiment, the first and/or second Fc-containing polypeptide is an antibody heavy chain. In a further embodiment, the antibody heavy chain is paired with an antibody light chain to provide a heavy-light chain pair. In some embodiments, the heavy-light chain pair are covalently linked. In another embodiment, the heavy-light chain pair defines a target binding arm. In some embodiments, the target binding arms are identical. In some embodiments, the target binding arms each recognize two distinct targets.

In another embodiment, the first and/or second Fc-containing polypeptide comprises a variable heavy chain domain. In another embodiment, the first and/or second Fc-containing polypeptide comprises a receptor binding domain. In some embodiments, the first and/or second Fc-containing polypeptide are substantially identical (i.e., the heterodimerization domain may not be identical with the regions outside of the heterodimerization domain being identical). In some embodiments, the first and/or second Fc-containing polypeptide are not identical.

In some embodiments, the heteromultimeric protein is selected from the group consisting of an antibody, a bispecific antibody, a multispecific antibody, one-armed antibody, monospecific monovalent antibody, a multispecific monovalent antibody, a bispecific maxibody, an immunoadhesin, a peptibody, a bispecific peptibody, a monovalent peptibody, an affibody and a receptor fusion protein.

In some embodiments, said heteromultimeric proteins comprise a hinge region that has at least one, at least two, at least three, at least four, or any integer number up to all, of the cysteine residues that are normally capable of forming an inter-heavy chain disulfide linkage. In some embodiments, additional cysteines have been introduced into the hinge region.

A heteromultimeric protein of the invention may also be an antibody fragment, such as, for example, an Fc or Fc fusion polypeptide, so long as it comprises the Fc region of an immunoglobulin. An Fc fusion polypeptide generally comprises an Fc polypeptide (or fragment thereof) fused to a heterologous polypeptide sequence (such as an antigen binding domain), such as a receptor extracellular domain (ECD) fused to an immunoglobulin Fc polypeptide (e.g., Flt receptor ECD fused to a IgG2 Fc). For example, in one embodiment, an Fc fusion polypeptide comprises a VEGF binding domain, which may be a VEGF receptor, which includes flt, flk, etc. A heteromultimeric protein of the invention generally comprises a heavy chain constant domain and a light chain constant domain. In one embodiment, a heteromultimeric protein of the invention comprises a modification (for example, but not limited to, insertion of one or more amino acids, e.g., to form a dimerization sequence such as leucine zipper) for formation of inter-heavy chain dimerization or multimerization. In some of these embodiments, the heteromultimeric protein comprises a dimerization domain (such as a leucine zipper sequence), for example fused to the C-terminus of the heavy chain fragment. In some of these embodiments, the heteromultimeric protein comprises a dimerization domain comprising mutations to provide for a "knob into hole" dimerization domain (as further defined below).

In some embodiments of the methods and heteromultimeric proteins of the invention, the Fc-containing polypeptides comprise at least one characteristic that promotes proper orientation of the Fc-containing polypeptides relative to each other, while improving overall yield, of the first and second Fc-containing polypeptides. Such characteristic(s) improves yield and/or purity and/or homogeneity of the heteromultimeric protein populations obtainable by methods of the invention as described herein. In one embodiment, the Fc polypeptides of a first Fc-containing polypeptide and a second Fc-containing polypeptide meet/interact at an interface. In some embodiments wherein the Fc polypeptides of the first and second Fc-containing polypeptides meet at an interface, the interface of the second Fc polypeptide comprises a protuberance which is positionable in a cavity in the interface of the first Fc polypeptide. In one embodiment, the first Fc polypeptide has been altered from a template/original polypeptide to encode the cavity or the second Fc polypeptide has been altered from a template/original polypeptide to encode the protuberance, or both. In one embodiment, the first Fc polypeptide has been altered from a template/original polypeptide to encode the cavity and the second Fc polypeptide has been altered from a template/original polypeptide to encode the protuberance, or both. In one embodiment, the interface of the second Fc polypeptide comprises a protuberance which is positionable in a cavity in the interface of the first Fc polypeptide, wherein the cavity or protuberance, or both, have been introduced into the interface of the first and second Fc polypeptides, respectively. In some embodiments wherein the first and second Fc polypeptides meet at an interface, the interface of the first Fc polypeptide comprises a protuberance which is positionable in a cavity in the interface of the second Fc polypeptide. In one embodiment, the second Fc polypeptide has been altered from a template/original polypeptide to encode the cavity or the first Fc polypeptide has been altered from a template/original polypeptide to encode the protuberance, or both. In one embodiment, the second Fc polypeptide has been altered from a template/original polypeptide to encode the cavity and the first Fc polypeptide has been altered from a template/original polypeptide to encode the protuberance, or both. In one embodiment, the interface of the first Fc polypeptide comprises a protuberance which is positionable in a cavity in the interface of the second Fc polypeptide, wherein the protuberance or cavity, or both, have been introduced into the interface of the first and second Fc polypeptides, respectively.

In one embodiment, the protuberance and cavity each comprises a naturally occurring amino acid residue. In one embodiment, the Fc polypeptide comprising the protuberance is generated by replacing an original residue from the interface of a template/original polypeptide with an import residue having a larger side chain volume than the original residue. In one embodiment, the Fc polypeptide comprising the protuberance is generated by a method comprising a step wherein nucleic acid encoding an original residue from the interface of said polypeptide is replaced with nucleic acid encoding an import residue having a larger side chain volume than the original. In one embodiment, the original residue is threonine. In one embodiment, the import residue is arginine (R). In one embodiment, the import residue is phenylalanine (F). In one embodiment, the import residue is tyrosine (Y). In one embodiment, the import residue is tryptophan (W). In one embodiment, the import residue is R, F, Y or W. In one embodiment, a protuberance is generated by replacing two or more residues in a template/original polypeptide. In one embodiment, the Fc polypeptide comprising a protuberance comprises replacement of threonine at position 366 with tryptophan, amino acid numbering according to the EU numbering scheme of Kabat et al. (pp. 688-696 in Sequences of proteins of immunological interest, 5th ed., Vol. 1 (1991; NIH, Bethesda, Md.)).

In some embodiments, the Fc polypeptide comprising a cavity is generated by replacing an original residue in the interface of a template/original polypeptide with an import residue having a smaller side chain volume than the original residue. For example, the Fc polypeptide comprising the cavity may be generated by a method comprising a step wherein nucleic acid encoding an original residue from the interface of said polypeptide is replaced with nucleic acid encoding an import residue having a smaller side chain volume than the original. In one embodiment, the original residue is threonine. In one embodiment, the original residue is leucine. In one embodiment, the original residue is tyrosine. In one embodiment, the import residue is not cysteine (C). In one embodiment, the import residue is alanine (A). In one embodiment, the import residue is serine (S). In one embodiment, the import residue is threonine (T). In one embodiment, the import residue is valine (V). A cavity can be generated by replacing one or more original residues of a template/original polypeptide. For example, in one embodiment, the Fc polypeptide comprising a cavity comprises replacement of two or more original amino acids selected from the group consisting of threonine, leucine and tyrosine. In one embodiment, the Fc polypeptide comprising a cavity comprises two or more import residues selected from the group consisting of alanine, serine, threonine and valine. In some embodiments, the Fc polypeptide comprising a cavity comprises replacement of two or more original amino acids selected from the group consisting of threonine, leucine and tyrosine, and wherein said original amino acids are replaced with import residues selected from the group consisting of alanine, serine, threonine and valine. In one embodiment, the Fc polypeptide comprising a cavity comprises replacement of threonine at position 366 with serine, amino acid numbering according to the EU numbering scheme of Kabat et al., supra. In one embodiment, the Fc polypeptide comprising a cavity comprises replacement of leucine at position 368 with alanine, amino acid numbering according to the EU numbering scheme of Kabat et al., supra. In one embodiment, the Fc polypeptide comprising a cavity comprises replacement of tyrosine at position 407 with valine, amino acid numbering according to the EU numbering scheme of Kabat et al., supra. In one embodiment, the Fc polypeptide comprising a cavity comprises two or more amino acid replacements selected from the group consisting of T366S, L368A and Y407V, amino acid numbering according to the EU numbering scheme of Kabat et al., supra. In some embodiments of these antibody fragments, the Fc polypeptide comprising the protuberance comprises replacement of threonine at position 366 with tryptophan, amino acid numbering according to the EU numbering scheme of Kabat et al., supra.

In one embodiment, the interface of the first Fc polypeptide and/or the second Fc polypeptide have been mutated to comprise substitutions at residues 241 and 243 on at least one heavy chain with an amino acid which is different from that present in an wild-type Fc polypeptide. In some embodiments, the mutations on at least Fc polypeptide, e.g., one heavy chain, are selected from F241 R/F243S and F241 S/F243R. In some embodiments, the Fc variant further comprises knob-into-hole modification(s).

In various embodiments, the Fc polypeptide of the first and second heavy chain polypeptides may or may not be identical, provided they are capable of dimerizing to form an Fc region (as defined herein). A first Fc polypeptide is generally contiguously linked to one or more domains of an immunoglobulin heavy chain in a single polypeptide, for example with hinge, constant and/or variable domain sequences. In one embodiment, the first Fc polypeptide comprises at least a portion (including all) of a hinge sequence, at least a portion (including all) of a $C_H2$ domain and/or at least a portion (including all) of a $C_H3$ domain. In one embodiment, the first Fc polypeptide comprises the hinge sequence and the $C_H2$ and $C_H3$ domains of an immunoglobulin. In one embodiment, the second Fc polypeptide comprises at least a portion (including all) of a hinge sequence, at least a portion (including all) of a $C_H2$ domain and/or at least a portion (including all) of a $C_H3$ domain. In one embodiment, the second Fc polypeptide comprises the hinge sequence and the $C_H2$ and $C_H3$ domains of an immunoglobulin. In one embodiment, an antibody of the invention comprises first and second Fc polypeptides each of which comprising at least a portion of at least one antibody constant domain. In one embodiment, the antibody constant domain is a $C_H2$ and/or $C_H3$ domain. In any of the embodiments of an antibody of the invention that comprises a constant domain, the antibody constant domain can be from any immunoglobulin class, for example an IgG. The immunoglobulin source can be of any suitable species of origin (e.g., an IgG may be human $IgG_1$) or of synthetic form.

In one embodiment, a first light chain polypeptide and a second light chain polypeptide in a first and second target molecule binding arm, respectively, of an antibody of the invention comprise different/distinct antigen binding determinants (e.g., different/distinct variable domain sequences). In one embodiment, a first light chain polypeptide and a second light chain polypeptide in a first and second target molecule binding arm, respectively, of an antibody of the invention comprise the same (i.e., a common) antigen binding determinant e.g., the same variable domain sequence).

Methods of the invention are capable of generating heteromultimeric molecules at high homogeneity. According, the invention provides methods wherein at least about 40%, 45%, 50%, 55%, 60%, 65%, 70%, 75%, 80%, 85%, 90%, 95%, 96%, 97%, 98%, 99% of polypeptides are in a complex comprising a first heavy and light chain polypeptide pair and a second heavy and light chain polypeptide pair. In one embodiment, the invention provides methods wherein between about 60 and 99%, 70 and 98%, 75 and 97%, 80 and 96%, 85 and 96%, or 90 and 95% of polypeptides are in a complex comprising a first heavy and light chain polypeptide pair and a second heavy and light chain polypeptide pair.

In one embodiment, an antibody of the invention is selected from the group consisting of IgG, IgE, IgA, IgM and IgD. In some embodiments, the hinge region of an antibody of the invention is preferably of an immunoglobulin selected from the group consisting of IgG, IgA and IgD. For example, in some embodiments, an antibody or hinge region of an antibody is of IgG, which in some embodiments is IgG1 or IgG2 (e.g., IgG2a or IgG2b). In some embodiments, an antibody of the invention is selected from the group consisting of IgG, IgA and IgD. In one embodiment, the antibody is of human, humanized, chimeric or non-human (e.g., murine) origin.

Heteromultimeric proteins of the invention generally are capable of binding, preferably specifically, to antigens. Such antigens include, for example, tumor antigens, cell survival regulatory factors, cell proliferation regulatory factors, molecules associated with (e.g., known or suspected to contribute functionally to) tissue development or differentiation, cell surface molecules, lymphokines, cytokines, molecules involved in cell cycle regulation, molecules involved in vasculogenesis and molecules associated with (e.g., known or suspected to contribute functionally to) angiogenesis. An antigen to which a heteromultimeric protein of the invention is capable of binding may be a member of a subset of one of the above-mentioned categories, wherein the other subset (s) of said category comprise other molecules/antigens that have a distinct characteristic (with respect to the antigen of interest). An antigen of interest may also be deemed to belong to two or more categories. In one embodiment, the invention provides a heteromultimeric protein that binds, preferably specifically, a tumor antigen that is not a cell surface molecule. In one embodiment, a tumor antigen is a cell surface molecule, such as a receptor polypeptide. In another example, in some embodiments, a heteromultimeric protein of the invention binds, preferably specifically, a tumor antigen that is not a cluster differentiation factor. In another example, a heteromultimeric protein of the invention is capable of binding, preferably specifically, to a cluster differentiation factor, which in some embodiments is not, for example, CD3 or CD4. In some embodiments, a heteromultimeric protein of the invention is an anti-VEGF antibody. In some embodiments, a heteromultimeric protein of the invention is a bispecific antibody selected from the group consisting of IL-Ialpha/IL-Ibeta, IL-12/IL-18; IL-13/IL-9;

IL-13/IL-4; IL-13/IL-5; IL-5/IL-4; IL-13/IL-Ibeta; IL-13/IL-25; IL-13/TARC; IL-13/MDC; IL-13/MEF; IL-13/TGF-β; IL-13/LHR agonist; IL-12/TWEAK, IL-13/CL25; IL-13/SPRR2a; IL-13/SPRR2b; IL-13/ADAM8, IL-13/PED2, IL17A/IL17F, CD3/CD19, CD138/CD20; CD138/CD40; CD19/CD20; CD20/CD3; CD38/CD138; CD38/CD20; CD38/CD40; CD40/CD20; CD-8/IL-6; CD20/BR3, TNFalpha/TGF-beta, TNFalpha/IL-Ibeta; TNFalpha/IL-2, TNF alpha/IL-3, TNFalpha/IL-4, TNFalpha/IL-5, TNFalpha/IL6, TNFalpha/IL8, TNFalpha/IL-9, TNFalpha/IL-10, TNFalpha/IL-11, TNFalpha/IL-12, TNFalpha/IL-13, TNFalpha/IL-14, TNFalpha/IL-15, TNFalpha/IL-16, TNFalpha/IL-17, TNFalpha/IL-18, TNFalpha/IL-19, TNFalpha/IL-20, TNFalpha/IL-23, TNFalpha/IFNalpha, TNFalpha/CD4, TNFalpha/VEGF, TNFalpha/MIF, TNFalpha/ICAM-1, TNFalpha/PGE4, TNFalpha/PEG2, TNFalpha/RANK ligand, TNFalpha/Te38; TNFalpha/BAFF; TNFalpha/CD22; TNFalpha/CTLA-4; TNFalpha/GP130; TNFα/IL-12p40; VEGF/HER2, VEGF-A/HER2, VEGF-A/PDGF, HER1/HER2, VEGF-A/VEGF-C, VEGF-C/VEGF-D, HER2/DR5, VEGF/IL-8, VEGF/MET, VEGFR/MET receptor, VEGFR/EGFR, HER2/CD64, HER2/CD3, HER2/CD16, HER2/HER3; EGFR/HER2, EGFR/HER3, EGFR/HER4, IL-13/CD40L, IL4/CD40L, TNFR1/IL-1R, TNFR1/IL-6R, TNFR1/IL-18R, EpCAM/CD3, MAPG/CD28, EGFR/CD64, CSPGs/RGM A; CTLA-4/BTNO2; IGF1/IGF2; IGF1/2/Erb2B; MAG/RGM A; NgR/RGM A; NogoA/RGM A; OMGp/RGM A; PDL-I/CTLA-4; and RGM A/RGM B, IL1β/IL18, NRP1/VEGFA, VEGFA/NRP2, cMET/EGFR, ALK1/BMP9, VEGFA/α5β1, HER1/HER3-BU, and CMV. In some embodiments, a heteromultimeric protein of the invention binds to at least two target molecules selected from the group consisting of: α5β1, ALK1, BMP9, IL-Ialpha, IL-Ibeta, TARC, MDC, MEF, TGF-β, LHR agonist, TWEAK, CL25, SPRR2a, SPRR2b, ADAM8, PED2, CD3, CD4, CD16, CD19, CD20, CD22, CD28, CD40, CD38, CD64, CD138, CD-8, BR3, TNFalpha, TGF-beta, IL-2, IL-3, IL-4, IL-5, IL-6, IL-8, IL-9, IL-10, IL-11, IL-12, IL-13, IL-14, IL-15, IL-16, IL-17, IL-17A, IL-17F, IL-18, IL-19, IL-20, IL-23, IL-25, IFNalpha, MIF, ICAM-1, PGE4, PEG2, RANK ligand, Te38, BAFF, CTLA-4, GP130, IL-12p40, VEGF, VEGF-A, PDGF, HER1, HER2, HER3, HER3-BU, HER4, VEGF-C, VEGF-D, DR5, cMET, MET, MET receptor, VEGFR, EGFR, CD40L, TNFR1, IL-1R, IL-6R, IL-18R, EpCAM, MAPG, CSPGs, BTNO2, IGF1, IGF2, IGF1/2, Erb2B, MAG, NgR, NogoA, NRP1, NRP2, OMGp, PDL-I, RGM A and RGM B. In some embodiments, a heteromultimeric protein of this invention binds to CD3 and at least one additional target molecule selected from BLR1, BR3, CD19, CD20, CD22, CD72, CD79A, CD79B, CD180 (RP105), CR2, FcRH1, FcRH2, FcRH5, FCER2, FCRL4, HLA-DOB, and NAG14.

First and second host cells in methods of the invention can be cultured in any setting that permits expression and isolation of the polypeptides of interest. For example, in one embodiment, the first host cell and the second host cell in a method of the invention are grown as separate cell cultures. In another embodiment, the first host cell and the second host cell in a method of the invention are grown as a mixed culture comprising both host cells.

Heteromultimeric proteins may be modified to enhance and/or add additional desired characteristics. Such characteristics include biological functions such as immune effector functions, a desirable in vivo half life/clearance, bioavailability, biodistribution or other pharmacokinetic characteristics. Such modifications are well known in the art and can also be determined empirically, and may include modifications by moieties that may or may not be peptide-based. For example, antibodies may be glycosylated or aglycosylated, generally depending at least in part on the nature of the host cell. Preferably, antibodies of the invention are aglycosylated. An aglycosylated antibody produced by a method of the invention can subsequently be glycosylated by, for example, using in vitro glycosylation methods well known in the art. As described above and herein, heteromultimeric proteins of the invention can be produced in a prokaryotic cell, such as, for example, E. coli. E. coli-produced heteromultimeric proteins are generally aglycosylated and lack the biological functions normally associated with glycosylation profiles found in mammalian host cell (e.g., CHO) produced heteromultimeric proteins.

The invention also provides immunoconjugates comprising a heteromultimeric protein of the invention conjugated with a heterologous moiety. Any heterologous moiety would be suitable so long as its conjugation to the antibody does not substantially reduce a desired function and/or characteristic of the antibody. For example, in some embodiments, an immunoconjugate comprises a heterologous moiety which is a cytotoxic agent. In some embodiments, said cytotoxic agent is selected from the group consisting of a radioactive isotope, a chemotherapeutic agent and a toxin. In some embodiments, said toxin is selected from the group consisting of calichemicin, maytansine and trichothene. In some embodiments, an immunoconjugate comprises a heterologous moiety which is a detectable marker. In some embodiments, said detectable marker is selected from the group consisting of a radioactive isotope, a member of a ligand-receptor pair, a member of an enzyme-substrate pair and a member of a fluorescence resonance energy transfer pair.

In one embodiment, the invention provides compositions comprising a heteromultimeric protein of the invention and a carrier, which in some embodiments is pharmaceutically acceptable.

In another embodiment, the invention provides compositions comprising an immunoconjugate as described herein and a carrier, which in some embodiments is pharmaceutically acceptable.

In one embodiment, the invention provides a composition comprising a population of multispecific heteromultimeric proteins of the invention. As would be evident to one skilled in the art, generally such a composition would not be completely (i.e., 100%) homogeneous. However, as described herein, methods of the invention are capable of producing a substantially homogeneous population of multispecific heteromultimeric proteins. For example, the invention provides a composition comprising heteromultimeric proteins, wherein at least 40%, 45%, 50%, 55%, 60%, 65%, 70%, 80%, 85%, 90%, 95%, 96%, 97%, 98%, 99% of said heteromultimeric proteins are a multispecific antibody (e.g., a bispecific antibody, etc.) of the invention as described herein.

In another embodiment, the invention provides articles of manufacture comprising a container and a composition contained therein, wherein the composition comprises a heteromultimeric protein (e.g., an antibody) of the invention. In another embodiment, the invention provides articles of manufacture comprising a container and a composition contained therein, wherein the composition comprises an immunoconjugate as described herein. In some embodiments, these articles of manufacture further comprise instructions for using said composition.

In yet another embodiment, the invention provides polynucleotides encoding a heteromultimeric protein of the invention. In still another embodiment, the invention provides polynucleotides encoding an immunoconjugate as described herein. In some embodiments, the nucleic acids (i.e., polynucleotides) are isolated.

In one embodiment, the invention provides recombinant vectors for expressing a molecule (e.g., an antibody) of the invention. In another embodiment, the invention provides recombinant vectors for expressing an immunoconjugate of the invention.

Any of a number of host cells can be used in methods of the invention. Such cells are known in the art (some of which are described herein) or can be determined empirically with respect to suitability for use in methods of the invention using routine techniques known in the art. In one embodiment, a host cell is prokaryotic. In some embodiments, a host cell is a gram-negative bacterial cell. In one embodiment, a host cell is *E. coli*. In some embodiments, the *E. coli* is of a strain deficient in lipoprotein (ΔIpp). In some embodiments, the genotype of an *E. coli* host cell lacks degP and prc genes and harbors a mutant spr gene. In one embodiment, a host cell is mammalian, for example, a Chinese Hamster Ovary (CHO) cell.

In one embodiment, the invention provides host cells comprising a polynucleotide or recombinant vector of the invention. In one embodiment, a host cell is a mammalian cell, for example a Chinese Hamster Ovary (CHO) cell. In one embodiment, a host cell is a prokaryotic cell. In some embodiments, a host cell is a gram-negative bacterial cell, which in some embodiments is *E. coli*. Host cells of the invention may further comprise a polynucleotide or recombinant vector encoding a molecule the expression of which in a host cell enhances yield of a heteromultimeric protein in a method of the invention. For example, such molecule can be a chaperone protein. In one embodiment, said molecule is a prokaryotic polypeptide selected from the group consisting of DsbA, DsbC, DsbG and FkpA. In some embodiments, said polynucleotide or recombinant vector encodes both DsbA and DsbC. In some embodiments, an *E. coli* host cell is of a strain deficient in endogenous protease activities. In some embodiments, the genotype of an *E. coli* host cell is that of an *E. coli* strain that lacks degP and prc genes and harbors a mutant spr gene. In some embodiments, the genotype of an *E. coli* host cell is ΔIpp.

Heteromultimeric proteins of the invention find a variety of uses in a variety of settings. In one example, a heteromultimeric protein of the invention is a therapeutic antibody. In another example, a heteromultimeric protein of the invention is an agonist antibody. In another example, a heteromultimeric protein of the invention is an antagonistic antibody. A heteromultimeric protein of the invention may also be a diagnostic antibody. In yet another example, a heteromultimeric protein of the invention is a blocking antibody. In another example, a heteromultimeric protein of the invention is a neutralizing antibody.

In one embodiment, the invention provides methods of treating or delaying a disease in a subject, said methods comprising administering a heteromultimeric protein of the invention to said subject. In one embodiment, the disease is cancer. In another embodiment, the disease is associated with dysregulation of angiogenesis. In another embodiment, the disease is an immune disorder, such as rheumatoid arthritis, immune thrombocytopenic purpura, systemic lupus erythematosus, etc.

In one embodiment, the invention provides use of a heteromultimeric protein (e.g., an antibody) of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one embodiment, the invention provides use of a nucleic acid of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one embodiment, the invention provides use of an expression vector of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one embodiment, the invention provides use of a host cell of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one embodiment, the invention provides use of an article of manufacture of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one embodiment, the invention provides use of a kit of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 3 illustrates the production of heteromultimeric proteins, e.g., bispecific antibodies, using separately engineered and expressed half-antibodies. The produced BsAb typically has two different heavy chains, each paired with its cognate light chain. In this method each light chain is not necessarily the same for each half-antibody.

FIG. 4D shows the carboxymethyl (CM) chromatogram, a photo of a SDS-PAGE gel and the deconvoluted mass for the production of an anti-EGFR/anti-c-met bispecific antibody. The CM chromatography produces a single peak that is subsequently analyzed by SDS-PAGE. The major band on the gel is the full-length (i.e., intact) bispecific antibody. A minor band can also be seen at the 75 kD range. The major band was subsequently analyzed by mass spectrometry and indicated that the only detectable intact antibody product was in agreement with theoretical MW of an anti-EGFR/anti-c-met bispecific antibody.

FIGS. 8A-D show the dimer content of different Fc variants. Gel filtration analysis of Fc's show different extents of dimerization. The Knob mutants demonstrate decreased non-covalent homodimerization when compared to the wild-type versions of both knob and hole.

FIG. 9A shows the hydrophobic contacts. Knob-knob Fc homodimers are rendered as cartoons with chain A shaded light and chain B shaded dark. Hydrophobic residues Y349, L368, K370, F405 and Y407 in chain As CH2 domain associate with residues F241, F243, V262, and V264 in chain B's CH3 domain. P395 and P396 create a hydrophobic pocket between the two CH2 domains. FIG. 9B shows the hydrophilic contacts are shown in this panel. Knob-knob Fc homodimers are rendered as cartoons with chain A shaded light and chain B shaded dark. Residues T350, K370, and D399 in chain As CH2 domain associate with residues S239, V240, R301, and K334 in chain B's CH3 domain. N389, Y391 and K392 form interactions between the two CH2 domains.

ABBREVIATIONS

Figure 1A:
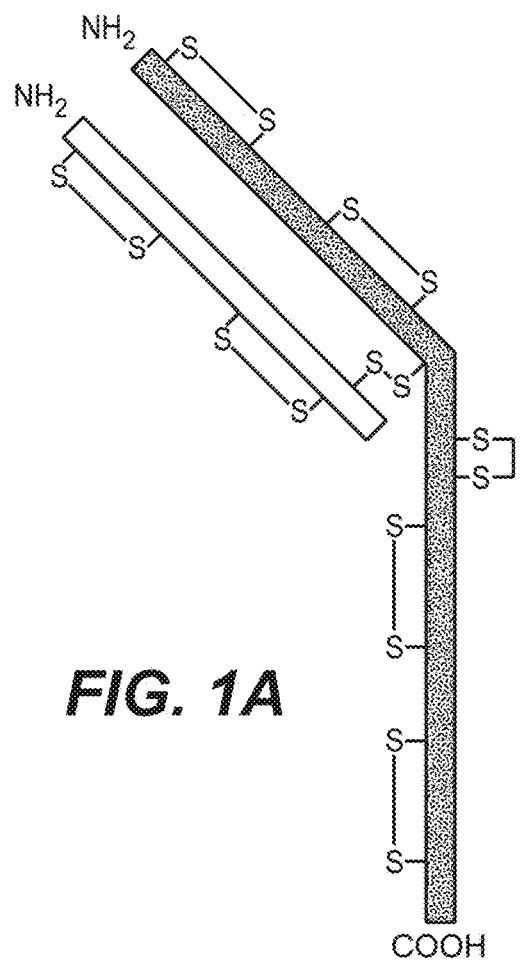
FIG. 1A illustrates a fully oxidized half-antibody. Not shown are the "knob" or "hole" or other heterodimerization domains. The half-antibody depicted in this figure is an IgG1 isotype. One skilled in the art will appreciate that the other immunoglobulin isotypes can be envisioned as half-antibodies with the corresponding inter- and intra-chain bonds. In an intact Ab the hinge cysteines will form inter-chain disulfide bonds.

ADCC=Antibody-dependent cell-mediated cytotoxicity
API=Anti-pathogen immunoadhesins
BPI=Bactericidal/permeability-increasing protein
C1q=Complement factor 1q
CD=Cluster of Differentiation
CDC=Complement-dependent cytotoxicity
CH1 or $C_H1$=Heavy chain first constant domain
CH2 or $C_H2$=Heavy chain second constant domain
CH3 or $C_H3$=Heavy chain third constant domain
CH4 or $C_H4$=Heavy chain fourth constant domain
CL or $C_L$=Light chain constant domain
CTLA=Cytotoxic T lymphocyte-associated molecule
Fc=Fragment crystallizable
Fc(R=Receptor gamma for the Fc portion of IgG
HIV=Human immunodeficiency virus
ICAM=Intercellular adhesion molecule
BsAb=Bispecific antibody
BsDb=Bispecific diabody
dsFv=Disulfide-stabilized Fv
Fc=Constant fragment of an antibody
Fd=$V_H$+$C_H1$ of an antibody
FcR=Fc receptor
Fv=Variable fragment of an antibody
IgG=Immunoglobulin G
mAb=Monoclonal antibody
PBL=Peripheral blood lymphocyte
scDb=Single-chain diabody
scFv=Single-chain Fv
$(scFv)_2$=scFv-scFv tandem
Tandab=Tandem diabody
VH or $V_H$=Variable domain of the heavy chain of an antibody
VL or $V_L$=Variable domain of the light chain of an antibody

DETAILED DESCRIPTION

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

I. DEFINITIONS

A "heteromultimer", "heteromultimeric complex", or "heteromultimeric protein" refers to a molecule comprising at least a first Fc-containing polypeptide and a second Fc-containing polypeptide, wherein the second Fc-containing polypeptide differs in amino acid sequence from the first Fc-containing polypeptide by at least one amino acid residue. The heteromultimer can comprise a "heterodimer" formed by the first and second Fc-containing polypeptides or can form higher order tertiary structures where polypeptides in addition to the first and second Fc-containing polypeptides are present. The polypeptides of the heteromultimer may interact with each other by a non-peptidic, covalent bond (e.g., disulfide bond) and/or a non-covalent interaction (e.g., hydrogen bonds, ionic bonds, van der Waals forces, and/or hydrophobic interactions).

As used herein, "heteromultimerization domain" refers to alterations or additions to a biological molecule so as to promote heteromultimer formation and hinder homomultimer formation. Any heterodimerization domain having a strong preference for forming heterodimers over homodimers is within the scope of the invention. Illustrative examples include but are not limited to, for example, US Patent Application 20030078385 (Arathoon et al.—Genentech; describing knob into holes); WO2007147901 (Kjærgaard et al.—Novo Nordisk: describing ionic interactions); WO 2009089004 (Kannan et al.—Amgen: describing electrostatic steering effects); U.S. Provisional Patent Application 61/243,105 (Christensen et al.—Genentech; describing coiled coils). See also, for example, Pack, P. & Plueckthun, A., Biochemistry 31, 1579-1584 (1992) describing leucine zipper or Pack et al., Bio/Technology 11, 1271-1277 (1993) describing the helix-turn-helix motif. The phrase "heteromultimerization domain" and "heterodimerization domain" are used interchangeably herein.

The term "antibody" herein is used in the broadest sense and refers to any immunoglobulin (Ig) molecule comprising two heavy chains and two light chains, and any fragment, mutant, variant or derivation thereof so long as they exhibit the desired biological activity (e.g., epitope binding activity). Examples of antibodies include monoclonal antibodies, polyclonal antibodies, multispecific antibodies (e.g., bispecific antibodies) and antibody fragments as described herein. An antibody can be human, humanized and/or affinity matured.

Figure 1B:
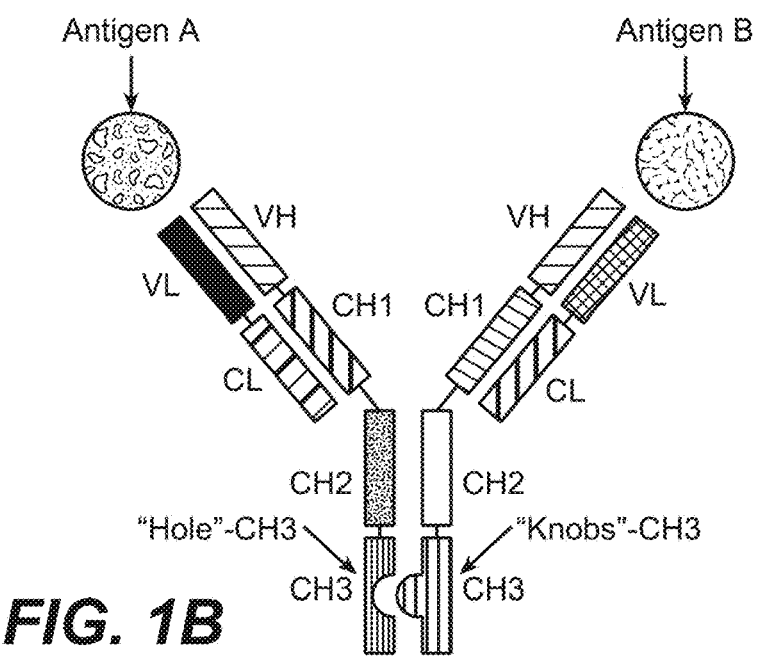
FIG. 1B illustrates a full-length bispecific antibody. Not depicted are the inter-heavy chain disulfide bonds in the hinge region.

As a frame of reference, as used herein an antibody will refer to the structure of an immunoglobulin G (IgG). However, one skilled in the art would understand/recognize that an antibody of any immunoglobulin class may be utilized in the inventive method described herein. For clarity, an IgG molecule contains a pair of identical heavy chains (HCs) and a pair of identical light chains (LCs). Each LC has one variable domain ($V_L$) and one constant domain ($C_L$), while each HC has one variable ($V_H$) and three constant domains ($C_H1$, $C_H2$, and $C_H3$). The $C_H1$ and $C_H2$ domains are connected by a hinge region. This structure is well known in the art. Reference is made to FIG. 1B.

As used herein, "half-antibody" refers to one immunoglobulin heavy chain associated with one immunoglobulin light chain. An exemplary half-antibody is depicted in FIG. 1A. One skilled in the art will readily appreciate that a half-antibody may also have an antigen binding domain consisting of a single variable domain.

The term "maxibody" refers to a fusion protein comprising a scFv fused to an Fc polypeptide. Reference is made to FIG. 8a of WO 2009089004. Reference is made to FIG. 2 of WO 2009089004 for a bispecific maxibody.

The term "$C_H2$ domain" of a human IgG Fc region usually extends from about residues 231 to about 340 of the IgG according to the EU numbering system. The $C_H2$ domain is unique in that it is not closely paired with another domain. Rather, two N-linked branched carbohydrate chains are interposed between the two $C_H2$ domains of an intact native IgG molecule. It has been speculated that the carbohydrate may provide a substitute for the domain-domain pairing and help stabilize the $C_H2$ domain. Burton, Molec. Immunol. 22:161-206 (1985).

The term "$C_H3$ domain" comprises the stretch of residues C-terminal to a $C_H2$ domain in an Fc region (i.e., from about amino acid residue 341 to about amino acid residue 447 of an IgG according to the EU numbering system).

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. The Fc sequence of an immunoglobulin generally comprises two constant domains, a $C_H2$ domain and a $C_H3$ domain, and optionally comprises a $C_H4$ domain. By "Fc polypeptide" herein is meant one of the polypeptides that make up an Fc region, e.g., a monomeric Fc. An Fc polypeptide may be obtained from any suitable immunoglobulin, such as $IgG_1$, $IgG_2$, $IgG_3$, or $IgG_4$ subtypes, IgA, IgE, IgD or IgM. The Fc region comprises the carboxy-terminal portions of both H chains held together by disulfides. The effector functions of antibodies are determined by sequences in the Fc region; this region is also the part recognized by Fc receptors (FcR) found on certain types of cells. In some embodiments, an Fc polypeptide comprises part or all of a wild type hinge sequence (generally at its N terminus). In some embodiments, an Fc polypeptide does not comprise a functional or wild type hinge sequence.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g., B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human $IgG_1$ Fc region (non-A and A allotypes); native sequence human $IgG_2$ Fc region; native sequence human $IgG_3$ Fc region; and native sequence human $IgG_4$ Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95%, at least about 96%, at least about 97%, at least about 98% or at least about 99% homology therewith.

"Fc component" as used herein refers to a hinge region, a $C_H2$ domain or a $C_H3$ domain of an Fc region.

In certain embodiments, the Fc-containing polypeptide comprises an IgG Fc region, preferably derived from a wild-type human IgG Fc region. By "wild-type" human IgG Fc it is meant a sequence of amino acids that occurs naturally within the human population. Of course, just as the Fc sequence may vary slightly between individuals, one or more alterations may be made to a wildtype sequence and still remain within the scope of the invention. For example, the Fc region may contain additional alterations that are not related to the present invention, such as a mutation in a glycosylation site or inclusion of an unnatural amino acid. When used in conjunction with knob, hole or knob/hole, "wild-type" is meant to refer to the protein sequence having only the knob, hole or knob/hole mutations introduced but is otherwise comprise the sequence that occurs naturally within the human population.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hypervariable regions (HVRs). (See, e.g., Kindt et al. *Kuby Immunology*, $6^{th}$ ed., W.H. Freeman and Co., page 91 (2007).) A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., *J. Immunol.* 150:880-887 (1993); Clarkson et al., *Nature* 352: 624-628 (1991).

The term "Fab" as used herein refers to an antigen-binding fragment of an antibody. As noted above, papain may be used to digest an intact antibody. Papain digestion of antibodies produces two identical antigen-binding fragments, i.e., "Fab" fragments, and a residual "Fc" fragment (i.e., the Fc region, supra). The Fab fragment consists of an entire L chain along with the variable region domain of the H chain ($V_H$), and the first constant domain of one heavy chain ($C_H1$).

The phrase "antigen binding arm", "target molecule binding arm", "target binding arm" and variations thereof, as used herein, refers to a component part of a heteromultimeric protein of the invention that has an ability to specifically bind a target of interest. Generally and preferably, the antigen binding arm is a complex of immunoglobulin polypeptide sequences, e.g., CDR and/or variable domain sequences of an immunoglobulin light and heavy chain.

A "target" or "target molecule" refers to a moiety recognized by a binding arm of the heteromultimeric protein. For example, if the heteromultimeric protein is an antibody, then the target may be epitopes on a single molecule or on different molecules, or a pathogen or a tumor cell, depending on the context. Similarly, if the heteromultimeric protein is a receptor-Fc fusion protein the target would be the cognate binding partner for the receptor. One skilled in the art will appreciate that the target is determined by the binding specificity of the target binding arm and that different target binding arms may recognize different targets. A target preferably binds to a heteromultimeric protein of this invention with affinity higher than 1 uM Kd (according to scatchard analysis). Examples of target molecules include, but are not limited to, serum soluble proteins and/or their receptors, such as cytokines and/or cytokine receptors, adhesins, growth factors and/or their receptors, hormones, viral particles (e.g., RSV F protein, CMV, StaphA, influenza, hepatitis C virus), microorganisms (e.g., bacterial cell proteins, fungal cells), adhesins, CD proteins and their receptors.

One example of an "intact" or "full-length" antibody is one that comprises an antigen-binding arm as well as a $C_L$ and at least heavy chain constant domains, $C_H1$, $C_H2$, and $C_H3$. The constant domains can be native sequence constant domains (e.g., human native sequence constant domains) or amino acid sequence variants thereof.

The term "coupling" as used herein refers to the steps necessary to link the first and second Fc-containing polypeptides to each other, e.g., formation of a covalent bond. Such steps comprise the reducing, annealing and/or oxidizing of cysteine residues in the hinge region of the first and second Fc-containing polypeptides to form an inter-chain disulfide bond. The coupling may be achieved by chemical cross-linking or the use of a redox system. See, e.g., Humphreys et al., J. Immunol. Methods (1998) 217:1-10 and Zhu et al., Cancer Lett., (1994) 86: 127-134.

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), wherein the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 μM to 0.001 pM, 3 μM to 0.001 pM, 1 μM to 0.001 pM, 0.5 μM to 0.001 pM, or 0.1 μM to 0.001 pM. An illustrative drawing of a bispecific is provided in FIG. 1B.

"Antibody fragments" comprise a portion of an intact antibody, preferably the antigen binding or a variable region of the intact antibody. Examples of antibody fragments include Fab, Fab', F(ab')$_2$, and Fv fragments; diabodies (Db); tandem diabodies (taDb), linear antibodies (e.g., U.S. Pat. No. 5,641,870; Zapata et al., Protein Eng. 8(10):1057-1062 (1995)); one-armed antibodies, single variable domain antibodies, minibodies, single-chain antibody molecules; and multispecific antibodies formed from antibody fragments (e.g., including but not limited to, Db-Fc, taDb-Fc, taDb-$C_H3$ and (scFV)4-Fc).

The expression "single domain antibodies" (sdAbs) or "single variable domain (SVD) antibodies" generally refers to antibodies in which a single variable domain ($V_H$ or $V_L$) can confer antigen binding. In other words, the single variable domain does not need to interact with another variable domain in order to recognize the target antigen. Single domain antibodies consist of a single monomeric variable antibody domain ($V_H$ or $V_L$) on each antigen binding arm. Examples of single domain antibodies include those derived from camelids (llamas and camels) and cartilaginous fish (e.g., nurse sharks) and those derived from recombinant methods from humans and mouse antibodies (Ward et al., Nature (1989) 341:544-546; Dooley and Flajnik, Dev Comp Immunol (2006) 30:43-56; Muyldermans et al., Trend Biochem Sci (2001) 26:230-235; Holt et al., Trends Biotechnol (2003):21:484-490; WO 2005/035572; WO 03/035694; Davies and Riechmann, Febs Lett (1994) 339:285-290; WO00/29004; WO 02/051870). A single variable domain antibody can be present in an antigen binding arm (e.g., homo- or hetero-multimer) with other variable regions or variable domains, in which case it is not a single domain antibody.

The term "knob-into-hole" or "KnH" technology as mentioned herein refers to the technology directing the pairing of two polypeptides together in vitro or in vivo by introducing a perturbance (knob) into one polypeptide and a cavity (hole) into the other polypeptide at an interface in which they interact. For example, KnHs have been introduced in the Fc:Fc binding interfaces, $C_L:C_H1$ interfaces or $V_H/V_L$ interfaces of antibodies (e.g., US2007/0178552, WO 96/027011, WO 98/050431 and Zhu et al. (1997) Protein Science 6:781-788). This is especially useful in driving the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains, which enables the sFv to form the desired structure for antigen binding. For a review of sFv, see Pluckthun, The Pharmacology of Monoclonal Antibodies, vol. 113, Rosenburg and Moore eds., Springer-Verlag, New York, pp. 269-315 (1994); Malmborg et al., J. Immunol. Methods 183:7-13, 1995.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA 90:6444-6448 (1993).

The term "one-armed antibody" or "one-armed antibodies" refers to an antibody that comprises (1) a variable domain joined by a peptide bond to polypeptide comprising a $C_H2$ domain, a $C_H3$ domain or a $C_H2$-$C_H3$ domain and (2) a second $C_H2$, $C_H3$ or $C_H2$-$C_H3$ domain, wherein a variable domain is not joined by a peptide bond to a polypeptide comprising the second $C_H2$, $C_H3$ or $C_H2$-$C_H3$ domain. In one embodiment, the one-armed antibody comprises 3 polypeptides (1) a first polypeptide comprising a variable domain (e.g., $V_H$), $C_H1$, $C_H2$ and $C_H3$, (2) a second polypeptide comprising a variable domain (e.g., $V_L$) and a $C_L$ domain, and (3) a third polypeptide comprising a $C_H2$ and $C_H3$ domain. In another embodiment, the one-armed antibody has a partial hinge region containing the two cysteine residues which form disulphide bonds linking the constant heavy chains. In one embodiment, the variable domains of the one armed antibody form an antigen binding region. In another embodiment, the variable domains of the one armed antibody are single variable domains, wherein each single variable domain is an antigen binding region. In an embodiment, the one-armed antibody is a single variable domain antibody.

Antibodies of the invention can be "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, provided that they exhibit the desired biological activity (U.S. Pat. No. 4,816,567; and Morrison et al., Proc. Natl. Acad. Sci. USA 81:6851-6855 (1984)). Chimeric antibodies of interest herein include primatized antibodies comprising variable domain antigen-binding sequences derived from a non-human primate (e.g., Old World Monkey, Ape, etc.) and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Peptibody" or "peptibodies" refers to a fusion of randomly generated peptides with an Fc domain. See U.S. Pat. No. 6,660,843, issued Dec. 9, 2003 to Feige et al. (incorporated by reference in its entirety). They include one or more peptides linked to the N-terminus, C-terminus, amino acid sidechains, or to more than one of these sites. Peptibody technology enables design of therapeutic agents that incorporate peptides that target one or more ligands or receptors, tumor-homing peptides, membrane-transporting peptides, and the like. Peptibody technology has proven useful in design of a number of such molecules, including linear and disulfide-constrained peptides, "tandem peptide multimers" (i.e., more than one peptide on a single chain of an Fc domain). See, for example, U.S. Pat. No. 6,660,843; U.S. Pat. App. No. 2003/0195156, published Oct. 16, 2003 (corresponding to WO 02/092620, published Nov. 21, 2002); U.S. Pat. App. No. 2003/0176352, published Sep. 18, 2003 (corresponding to WO 03/031589, published Apr. 17, 2003); U.S. Ser. No. 09/422,838, filed Oct. 22, 1999 (corresponding to WO 00/24770, published May 4, 2000); U.S. Pat. App. No. 2003/0229023, published Dec. 11, 2003; WO 03/057134, published Jul. 17, 2003; U.S. Pat. App. No. 2003/0236193, published Dec. 25, 2003 (corresponding to PCT/US04/010989, filed Apr. 8, 2004); U.S. Ser. No. 10/666,480, filed Sep. 18, 2003 (corresponding to WO 04/026329, published Apr. 1, 2004), each of which is hereby incorporated by reference in its entirety.

"Affibodies" or "Affibody" refers to the use of a protein linked by peptide bond to an Fc region, wherein the protein is used as a scaffold to provide a binding surface for a target molecule. The protein is often a naturally occurring protein such as staphylococcal protein A or IgG-binding B domain, or the Z protein derived therefrom (see Nilsson et al (1987), Prot Eng 1, 107-133, and U.S. Pat. No. 5,143,844) or a fragment or derivative thereof. For example, affibodies can be created from Z proteins variants having altered binding affinity to target molecule(s), wherein a segment of the Z protein has been mutated by random mutagenesis to create a library of variants capable of binding a target molecule. Examples of affibodies include U.S. Pat. No. 6,534,628, Nord K et al, Prot Eng 8:601-608 (1995) and Nord K et al, Nat Biotech 15:772-777 (1997). Biotechnol Appl Biochem. 2008 June; 50(Pt 2):97-112.

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous" compared to a constant region of an antibody), and an immunoglobulin constant domain sequence (e.g., $C_H2$ and/or $C_H3$ sequence of an IgG). Exemplary adhesin sequences include contiguous amino acid sequences that comprise a portion of a receptor or a ligand that binds to a protein of interest. Adhesin sequences can also be sequences that bind a protein of interest, but are not receptor or ligand sequences (e.g., adhesin sequences in peptibodies). Such polypeptide sequences can be selected or identified by various methods, include phage display techniques and high throughput sorting methods. The immunoglobulin constant domain sequence in the immunoadhesin can be obtained from any immunoglobulin, such as IgG1, IgG2, IgG3, or IgG4 subtypes, IgA (including IgA1 and IgA2), IgE, IgD, or IgM.

"Complex" or "complexed" as used herein refers to the association of two or more molecules that interact with each other through bonds and/or forces (e.g., van der waals, hydrophobic, hydrophilic forces) that are not peptide bonds. In one embodiment, the complex is heteromultimeric. It should be understood that the term "protein complex" or "polypeptide complex" as used herein includes complexes that have a non-protein entity conjugated to a protein in the protein complex (e.g., including, but not limited to, chemical molecules such as a toxin or a detection agent).

A heteromultimeric protein of this invention "which binds an antigen of interest is one that binds the target with sufficient affinity such that the heteromultimeric protein is useful as a diagnostic and/or therapeutic agent in targeting a protein or a cell or tissue expressing the target, and does not significantly cross-react with other proteins. In such embodiments, the extent of binding of the heteromultimeric protein to a "non-target" protein will be less than about 10% of the binding of the antibody to its particular target protein as determined by fluorescence activated cell sorting (FACS) analysis or radioimmunoprecipitation (RIA) or ELISA. With regard to the binding of a heteromultimeric protein to a target molecule, the term "specific binding" or "specifically binds to" or is "specific for" a particular polypeptide or an epitope on a particular polypeptide target means binding that is measurably different from a non-specific interaction (e.g., a non-specific interaction may be binding to bovine serum albumin or casein). Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In one embodiment, the term "specific binding" refers to binding where a heteromultimeric protein binds to a particular polypeptide or epitope on a particular polypeptide without substantially binding to any other polypeptide or polypeptide epitope.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

In one embodiment, the "Kd" or "Kd value according to this invention is measured by using surface plasmon resonance assays using a BIAcore™-2000 or a BIAcore™-3000 (BIAcore, Inc., Piscataway, N.J.) at 25° C. with immobilized target (e.g., antigen) CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 μg/ml (~0.2 μM) before injection at a flow rate of 5 μl/minute to achieve approximately 10 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 μl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

"Biologically active" and "biological activity" and "biological characteristics" with respect to a heteromultimeric protein of this invention, such as an antibody, fragment, or derivative thereof, means having the ability to bind to a biological molecule, except where specified otherwise.

"Isolated," when used to describe the various heteromultimer polypeptides means a heteromultimer which has been separated and/or recovered from a cell or cell culture from which it was expressed. Contaminant components of its natural environment are materials which would interfere with diagnostic or therapeutic uses for the heteromultimer, and may include enzymes, hormones, and other proteinaceous or nonproteinaceous solutes. In certain embodiments, the heteromultimer will be purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Ordinarily, however, isolated polypeptide will be prepared by at least one purification step.

The heteromultimers of the present invention are generally purified to substantial homogeneity. The phrases "substantially homogeneous", "substantially homogeneous form" and "substantial homogeneity" are used to indicate that the product is substantially devoid of by-products originated from undesired polypeptide combinations (e.g., homomultimers).

Expressed in terms of purity, substantial homogeneity means that the amount of by-products does not exceed 10%, 9%, 8%, 7%, 6%, 4%, 3%, 2% or 1% by weight or is less than 1% by weight. In one embodiment, the by-product is below 5%.

"Biological molecule" refers to a nucleic acid, a protein, a carbohydrate, a lipid, and combinations thereof. In one embodiment, the biologic molecule exists in nature.

By "linked" or "links as used herein is meant either a direct peptide bond linkage between a first and second amino acid sequence or a linkage that involves a third amino acid sequence that is peptide bonded to and between the first and second amino acid sequences. For example, a linker peptide bonded to the C-terminal end of one amino acid sequence and to the N-terminal end of the other amino acid sequence.

By "linker" as used herein is meant an amino acid sequence of two or more amino acids in length. The linker can consist of neutral polar or nonpolar amino acids. A linker can be, for example, 2 to 100 amino acids in length, such as between 2 and 50 amino acids in length, for example, 3, 5, 10, 15, 20, 25, 30, 35, 40, 45, or 50 amino acids in length. A linker can be "cleavable," for example, by auto-cleavage, or enzymatic or chemical cleavage. Cleavage sites in amino acid sequences and enzymes and chemicals that cleave at such sites are well known in the art and are also described herein.

By a "tether" as used herein is meant an amino acid linker that joins two other amino acid sequences. A tether as described herein can link the N-terminus of an immunoglobulin heavy chain variable domain with the C-terminus of an immunoglobulin light chain constant domain. In particular embodiments, a tether is between about 15 and 50 amino acids in length, for example, between 20 and 26 amino acids in length (e.g., 20, 21, 22, 23, 24, 25, or 26 amino acids in length). A tether may be "cleavable," for example, by auto-cleavage, or enzymatic or chemical cleavage using methods and reagents standard in the art.

Enzymatic cleavage of a "linker" or a "tether" may involve the use of an endopeptidase such as, for example, Lys-C, Asp-N, Arg-C, V8, Glu-C, chymotrypsin, trypsin, pepsin, papain, thrombin, Genenase, Factor Xa, TEV (tobacco etch virus cysteine protease), Enterokinase, HRV C3 (human rhinovirus C3 protease), Kininogenase, as well as subtilisin-like proprotein convertases (e.g., Furin (PC1), PC2, or PC3) or N-arginine dibasic convertase. Chemical cleavage may involve use of, for example, hydroxylamine, N-chlorosuccinimide, N-bromosuccinimide, or cyanogen bromide.

A "Lys-C endopeptidase cleavage site" as used herein is a Lysine residue in an amino acid sequence that can be cleaved at the C-terminal side by Lys-C endopeptidase. Lys-C endopeptidase cleaves at the C-terminal side of a Lysine residue.

By a "chaotropic agent" is meant a water-soluble substance which disrupts the three-dimensional structure of a protein (e.g., an antibody) by interfering with stabilizing intra-molecular interactions (e.g., hydrogen bonds, van der Waals forces, or hydrophobic effects). Exemplary chaotropic agents include, but are not limited to, urea, Guanidine-HCl, lithium perchlorate, Histidine, and Arginine.

By a "mild detergent" is meant a water-soluble substance which disrupts the three-dimensional structure of a protein (e.g., an antibody) by interfering with stabilizing intra-molecular interactions (e.g., hydrogen bonds, van der Waals forces, or hydrophobic effects), but which does not permanently disrupt the protein structure as to cause a loss of biological activity (i.e., does not denature the protein). Exemplary mild detergents include, but are not limited to, Tween (e.g., Tween-20), Triton (e.g., Triton X-100), NP-40 (nonyl phenoxylpolyethoxylethanol), Nonidet P-40 (octyl phenoxylpolyethoxylethanol), and Sodium Dodecyl Sulfate (SDS).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxic agents. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. Nos. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al., Proc. Natl. Acad. Sci. USA 95:652-656 (1998).

"Fc receptor" or "FcR" describes a receptor that binds to the Fc region of an antibody. The preferred FcR is a human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. Daëron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), can be performed.

The term "therapeutically effective amount" refers to an amount of an antibody, antibody fragment, or derivative to treat a disease or disorder in a subject. In the case of tumor (e.g., a cancerous tumor), the therapeutically effective amount of the antibody or antibody fragment (e.g., a multispecific antibody or antibody fragment) may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The terms "cancer" and "cancerous" refer to or describe the physiological condition in mammals that is typically characterized by unregulated cell growth/proliferation. Included in this definition are benign and malignant cancers. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastric or stomach cancer including gastrointestinal cancer, pancreatic cancer, glioblastoma, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer (e.g., renal cell carcinoma), liver cancer, prostate cancer, vulval cancer, thyroid cancer, hepatic carcinoma, anal carcinoma, penile carcinoma, melanoma, and various types of head and neck cancer. By "early stage cancer" is meant a cancer that is not invasive or metastatic or is classified as a Stage 0, I, or II cancer. The term "precancerous" refers to a condition or a growth that typically precedes or develops into a cancer. By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

An "allergic or inflammatory disorder" herein is a disease or disorder that results from a hyper-activation of the immune system of an individual. Exemplary allergic or inflammatory disorders include, but are not limited to, asthma, psoriasis, rheumatoid arthritis, atopic dermatitis, multiple sclerosis, systemic lupus, erythematosus, eczema, organ transplantation, age-related muscular degeneration, Crohn's disease, ulcerative colitis, eosinophilic esophagitis, and autoimmune diseases associated with inflammation.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and auto-immune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia areata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as Leishmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigenantibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

The term "cytotoxic agent" as used herein refers to a substance that inhibits or prevents the function of a cell and/or causes destruction of a cell. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $Ra^{223}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor, anticancer, and chemotherapeutic agents disclosed herein. Other cytotoxic agents are described herein. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-am inocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1 (see, e.g., Agnew, Chem Intl. Ed. Engl. 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (e.g., vincristine and vinblastine), taxanes, and topoisomerase II inhibitors such as doxorubicin, epirubicin, daunorubicin, etoposide, and bleomycin. The agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Anti-cancer therapy" as used herein refers to a treatment that reduces or inhibits cancer in a subject. Examples of anti-cancer therapy include cytotoxic radiotherapy as well as the administration of a therapeutically effective amount of a cytotoxic agent, a chemotherapeutic agent, a growth inhibitory agent, a cancer vaccine, an angiogenesis inhibitor, a prodrug, a cytokine, a cytokine antagonist, a corticosteroid, an immunosuppressive agent, an anti-emetic, an antibody or antibody fragment, or an analgesic to the subject.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone (HGH), N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor (EGF); hepatic growth factor; fibroblast growth factor (FGF); prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-1beta, IL-2, IL-3, IL-4, IL-5, IL-6, IL-7, IL-8, IL-9, IL-10, IL-11, IL-12; IL-18 a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

By "cytokine antagonist" is meant a molecule that partially or fully blocks, inhibits, or neutralizes a biological activity of at least one cytokine. For example, the cytokine antagonists may inhibit cytokine activity by inhibiting cytokine expression and/or secretion, or by binding to a cytokine or to a cytokine receptor. Cytokine antagonists include antibodies, synthetic or native-sequence peptides, immunoadhesins, and small-molecule antagonists that bind to a cytokine or cytokine receptor. The cytokine antagonist is optionally conjugated with or fused to a cytotoxic agent. Exemplary TNF antagonists are etanercept (ENBREL®), infliximab (REMICADE®), and adalimumab (HUMIRA™).

The term "immunosuppressive agent" as used herein refers to substances that act to suppress or mask the immune system of the subject being treated. This includes substances that suppress cytokine production, downregulate or suppress self-antigen expression, or mask the MHC antigens. Examples of immunosuppressive agents include 2-amino-6-aryl-5-substituted pyrimidines (see U.S. Pat. No. 4,665, 077); mycophenolate mofetil such as CELLCEPT®; azathioprine (IMURAN®, AZASAN®/6-mercaptopurine; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids and glucocorticosteroids, e.g., prednisone, prednisolone such as PEDIAPRED® (prednisolone sodium phosphate) or ORAPRED® (prednisolone sodium phosphate oral solution), methylprednisolone, and dexamethasone; methotrexate (oral or subcutaneous) (RHEUMATREX®, TREXALL™); hydroxycloroquine/chloroquine; sulfasalazine; leflunomide; cytokine or cytokine receptor antagonists including anti-interferon-$\gamma$, -$\beta$, or -$\alpha$ antibodies, anti-tumor necrosis factor-$\alpha$ antibodies (infliximab or adalimumab), anti-TNF$\alpha$ immunoadhesin (ENBREL®, etanercept), anti-tumor necrosis factor-$\beta$ antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; polyclonal or pan-T antibodies, or monoclonal anti-CD3 or anti-CD4/CD4a antibodies; soluble peptide containing a LFA-3 binding domain (WO 90/08187); streptokinase; TGF-$\beta$; streptodornase; RNA or DNA from the host; FK506; RS-61443; deoxyspergualin; rapamycin; T-cell receptor (Cohen et al., U.S. Pat. No. 5,114,721); T-cell receptor fragments (Offner et al. Science 251: 430-432 (1991); WO 90/11294; Ianeway, Nature 341:482 (1989); and WO 91/01133); T cell receptor antibodies (EP 340,109) such as T10B9; cyclophosphamide (CYTOXAN®); dapsone; penicillamine (CUPRIMINE®); plasma exchange; or intravenous immunoglobulin (IVIG). These may be used alone or in combination with each other, particularly combinations of steroid and another immunosuppressive agent or such combinations followed by a maintenance dose with a non-steroid agent to reduce the need for steroids.

An "analgesic" refers to a drug that acts to inhibit or suppress pain in a subject. Exemplary analgesics include non-steroidal anti-inflammatory drugs (NSAIDs) including ibuprofen (MOTRIN®), naproxen (NAPROSYN®), acetylsalicylic acid, indomethacin, sulindac, and tolmetin, including salts and derivatives thereof, as well as various other medications used to reduce the stabbing pains that may occur, including anticonvulsants (gabapentin, phenyloin, carbamazepine) or tricyclic antidepressants. Specific examples include acetaminophen, aspirin, amitriptyline (ELAVIL®), carbamazepine (TEGRETOL®), phenyltoin (DILANTIN®), gabapentin (NEURONTIN®), (E)-N-Vanillyl-8-methyl-6-noneamid (CAPSAICIN®), or a nerve blocker.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone), dexamethasone triamcinolone, and betamethasone.

A "cancer vaccine," as used herein is a composition that stimulates an immune response in a subject against a cancer. Cancer vaccines typically consist of a source of cancer-associated material or cells (antigen) that may be autologous (from self) or allogenic (from others) to the subject, along with other components (e.g., adjuvants) to further stimulate and boost the immune response against the antigen. Cancer vaccines can result in stimulating the immune system of the subject to produce antibodies to one or several specific antigens, and/or to produce killer T cells to attack cancer cells that have those antigens.

"Cytotoxic radiotherapy" as used herein refers to radiation therapy that inhibits or prevents the function of cells and/or causes destruction of cells. Radiation therapy may include, for example, external beam irradiation or therapy with a radioactive labeled agent, such as an antibody. The term is intended to include use of radioactive isotopes (e.g., $At^{211}$, $I^{131}$, $I^{125}$, $Y^{90}$, $Re^{186}$, $Re^{188}$, $Sm^{153}$, $Bi^{212}$, $Ra^{223}$, $P^{32}$, and radioactive isotopes of Lu).

A "subject" is a vertebrate, such as a mammal, e.g., a human. Mammals include, but are not limited to, farm animals (such as cows), sport animals, pets (such as cats, dogs and horses), primates, mice, and rats.

Except where indicated otherwise by context, the terms "first" polypeptide and "second" polypeptide, and variations thereof, are merely generic identifiers, and are not to be taken as identifying a specific or a particular polypeptide or component of antibodies of the invention.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., Current Protocols in Molecular Biology (Green Publishing Associates and Wiley Interscience, NY, 1989); Innis et al., PCR Protocols: A Guide to Methods and Applications (Academic Press, Inc., NY, 1990); Harlow et al., Antibodies: A Laboratory Manual (Cold Spring Harbor Press, Cold Spring Harbor, 1988); Gait, Oligonucleotide Synthesis (IRL Press, Oxford, 1984); Freshney, Animal Cell Culture, 1987; Coligan et al., Current Protocols in Immunology, 1991.

Throughout this specification and claims, the word "comprise," or variations such as "comprises" or "comprising," will be understood to imply the inclusion of a stated integer or group of integers but not the exclusion of any other integer or group of integers.

II. CONSTRUCTION OF HETEROMULTIMERIC PROTEINS

Typically, the heteromultimeric proteins described herein will comprise a significant portion of an antibody Fc region.
Heteromultimerization Domains The heteromultimeric proteins comprise a heteromultimerization domain. To generate a substantially homogeneous population of heterodimeric molecule, the heterodimerization domain must have a strong preference for forming heterodimers over homodimers. Although the heteromultimeric proteins exemplified herein use the knobs into holes technology to facilitate heteromultimerization those skilled in the art will appreciate other heteromultimerization domains useful in the instant invention.
Knobs into Holes The use of knobs into holes as a method of producing multispecific antibodies is well known in the art. See U.S. Pat. No. 5,731,168 granted 24 Mar. 1998 assigned to Genentech, PCT Pub. No. WO2009089004 published 16 Jul. 2009 and assigned to Amgen, and US Pat. Pub. No. 20090182127 published 16 Jul. 2009 and assigned to Novo Nordisk A/S.

See also Marvin and Zhu, Acta Pharmacologica Sincia (2005) 26(6):649-658 and Kontermann (2005) Acta Pharacol. Sin., 26:1-9. A brief discussion is provided here.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g. by altering nucleic acid encoding the interface). Normally, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The upper limit for the number of original residues which are replaced is the total number of residues in the interface of the first polypeptide. The side chain volumes of the various amino residues are shown in the following table.

TABLE 2

Properties of Amino Acid Residues

| Amino Acid | One-Letter Abbreviation | MASS[a] (daltons) | VOLUME[b] (Angstrom$^3$) | Accessible Surface Area[c] (Angstrom$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalinine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight amino acid minus that of water. Values from *Handbook of Chemistry and Physics*, 43rd ed. Cleveland, Chemical Rubber Publishing Co., 1961.
[b]Values from A. A. Zamyatnin, *Prog. Biophys. Mol. Biol.* 24: 107-123, 1972.
[c]Values from C. Chothia, *J. Mol. Biol.* 105: 1-14, 1975. The accessible surface area is defined in FIGS. 6-20 of this reference.

The preferred import residues for the formation of a protuberance are generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The side chain volumes of the various amino residues are shown in Table 2 above. The preferred import residues for the formation of a cavity are usually naturally occurring amino acid residues and are preferably selected from alanine (A), serine (S), threonine (T) and valine (V). Most preferred are serine, alanine or threonine. In one embodiment, the original residue for the formation of the cavity has a large side chain volume, such as tyrosine, arginine, phenylalanine or tryptophan.

An "original" amino acid residue is one which is replaced by an "import" residue which can have a smaller or larger side chain volume than the original residue. The import amino acid residue can be a naturally occurring or non-naturally occurring amino acid residue, but preferably is the former. "Naturally occurring" amino acid residues are those residues encoded by the genetic code and listed in Table 2 above. By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., *Meth. Enzym.* 202:301-336 (1991), for example. To generate such non-naturally occurring amino acid residues, the procedures of Noren et al. *Science* 244: 182 (1989) and Ellman et al., supra can be used. Briefly, this involves chemically activating a suppressor tRNA with a non-naturally occurring amino acid residue followed by in vitro transcription and translation of the RNA. The method of the instant invention involves replacing at least one original amino acid residue, but more than one original residue can be replaced. Normally, no more than the total residues in the interface of the first or second polypeptide will comprise original amino acid residues which are replaced. Typically, original residues for replacement are "buried". By "buried" is meant that the residue is essentially inaccessible to solvent. Generally, the import residue is not cysteine to prevent possible oxidation or mispairing of disulfide bonds.

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art.

By "original or template nucleic acid" is meant the nucleic acid encoding a polypeptide of interest which can be "altered" (i.e. genetically engineered or mutated) to encode a protuberance or cavity. The original or starting nucleic acid may be a naturally occurring nucleic acid or may comprise a nucleic acid which has been subjected to prior alteration (e.g. a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in *Mutagenesis: a Practical Approach*, M. J. McPherson, Ed., (IRL Press, Oxford, UK. (1991), and include site-directed mutagenesis, cassette mutagenesis and polymerase chain reaction (PCR) mutagenesis, for example. By mutating an original/template nucleic acid, an original/template polypeptide encoded by the original/template nucleic acid is thus correspondingly altered.

The protuberance or cavity can be "introduced" into the interface of a first or second polypeptide by synthetic means, e.g. by recombinant techniques, in vitro peptide synthesis, those techniques for introducing non-naturally occurring amino acid residues previously described, by enzymatic or chemical coupling of peptides or some combination of these techniques. Accordingly, the protuberance or cavity which is "introduced" is "non-naturally occurring" or "non-native", which means that it does not exist in nature or in the original polypeptide (e.g. a humanized monoclonal antibody).

Generally, the import amino acid residue for forming the protuberance has a relatively small number of "rotamers" (e.g. about 3-6). A "rotomer" is an energetically favorable conformation of an amino acid side chain. The number of rotomers of the various amino acid residues are reviewed in Ponders and Richards, *J. Mol. Biol.* 193: 775-791 (1987).

Other Mutations

The Fc polypeptides described herein may have mutations that confer decreased mispairing, decreased head-to-tail formation or increased overall yield as compared to the wild-type Fc polypeptide or knob-into-hole Fc polypeptide. The Fc variant comprises at least one, two, three, four, five, six, seven, eight, nine or ten substitutions at residues selected from S239, V240, F241, F243, V264, R301, K334, Y349, T350, L368, K370, N389, Y391, K392, P395, P396, D399, F405, Y407 on at least one heavy chain with an amino acid which is different from that present in an wild-type Fc polypeptide. It may be desirable to alter effector function and it is contemplated that some of the mutations may enhance or decrease effector function. It is preferred that the mutations do not significantly alter other functional characteristics of the antibody, e.g., effector function.

III. VECTORS, HOST CELLS AND RECOMBINANT METHODS

For recombinant production of a heteromultimeric protein (e.g., an antibody) of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian, but also including fungi (e.g., yeast), insect, plant, and nucleated cells from other multicellular organisms) origin. It will be appreciated that constant regions of any isotype can be used for this purpose, including IgG, IgM, IgA, IgD, and IgE constant regions, and that such constant regions can be obtained from any human or animal species.

a. Generating Heteromultimeric Proteins Using Prokaryotic Host Cells i. Vector Construction Polynucleotide sequences encoding polypeptide components of the heteromultimeric proteins (e.g., an antibody) of the invention can be obtained using standard recombinant techniques. Desired polynucleotide sequences may be isolated and sequenced from, for example, antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. An inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding, for example, the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of the expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker to operably ligate them to cistrons encoding the genes of the heteromultimeric protein, e.g., the target light and heavy chains (Siebenlist et al., (1980) Cell 20: 269), using linkers or adaptors to supply any required restriction sites.

In one embodiment of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, Lam B, PhoE, PelB, OmpA and MBP. In one embodiment of the invention, the signal sequences used in both cistrons of the expression system are STII signal sequences or variants thereof.

In another embodiment, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the $E.$ $coli$ trxB⁻ strains) provide cytoplasm conditions that are favorable for disulfide bond formation, thereby permitting proper folding and assembly of expressed protein subunits. See Proba and Pluckthun $Gene$, 159:203 (1995).

Prokaryotic host cells suitable for expressing heteromultimeric proteins (e.g., antibodies) of the invention include $Archaebacteria$ and $Eubacteria$, such as Gram-negative or Gram-positive organisms. Examples of useful bacteria include $Escherichia$ (e.g., $E.$ $coli$), $Bacilli$ (e.g., $B.$ $subtilis$), $Enterobacteria$, $Pseudomonas$ species (e.g., $P.$ $aeruginosa$), $Salmonella$ $typhimurium$, $Serratia$ $marcescans$, $Klebsiella$, $Proteus$, $Shigella$, $Rhizobia$, $Vitreoscilla$, or $Paracoccus$. In one embodiment, gram-negative cells are used. In one embodiment, $E.$ $coli$ cells are used as hosts for the invention. Examples of $E.$ $coli$ strains include strain W3110 (Bachmann, $Cellular$ $and$ $Molecular$ $Biology$, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kan$^R$ (U.S. Pat. No. 5,639,635). Other strains and derivatives thereof, such as $E.$ $coli$ 294 (ATCC 31,446), $E.$ $coli$ B, $E.$ $coli_\lambda$ 1776 (ATCC 31,537) and $E.$ $coli$ RV308 (ATCC 31,608) are also suitable. In one embodiment, $E.$ $coli$ Δlpp finds particular use. These examples are illustrative rather than limiting. Methods for constructing derivatives of any of the above-mentioned bacteria having defined genotypes are known in the art and described in, for example, Bass et al., $Proteins$, 8:309-314 (1990). It is generally necessary to select the appropriate bacteria taking into consideration replicability of the replicon in the cells of a bacterium. For example, $E.$ $coli$, $Serratia$, or $Salmonella$ species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Polypeptide Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For $E.$ $coli$ growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For $E.$ $coli$, the pH is preferably from about 6.8 to about 7.4, and more preferably about 7.0.

If an inducible promoter is used in the expression vector of the invention, protein expression is induced under conditions suitable for the activation of the promoter. In one embodiment of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

In one embodiment, the first and second Fc-containing host cells are cultured separately and the expressed polypeptides of the present invention are secreted into and recovered from the periplasm of the host cells separately. In a second embodiment, the first and second Fc-containing host cells are cultured separately and prior to the isolation of the Fc-containing polypeptides, the two host cell cultures are mixed together and the cells pelleted. In a third embodiment, the first and second Fc-containing host cells are cultured separately, centrifuged and resuspended separately and then mixed together prior to isolation of the Fc-containing polypeptides. In a fourth embodiment, the first and second Fc-containing host cells are cultured together in the same culture vessel. Protein recovery typically involves disrupting the microorganism cell membrane, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay. The isolated polypeptides will be used to produce the heteromultimeric proteins at In one embodiment of the invention, heteromultimeric protein (e.g., antibody) production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted heteromultimeric proteins (e.g., antibodies), additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275:17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), *Proc. Natl. Acad. Sci. USA* 95:2773-2777; Georgiou et al., U.S. Pat. No. 5,264,365; Georgiou et al., U.S. Pat. No. 5,508,192; Hara et al., *Microbial Drug Resistance*, 2:63-72 (1996).

In one embodiment, *E. coli* strains deficient for proteolytic enzymes and transformed with plasmids overexpressing one or more chaperone proteins are used as host cells in the expression system of the invention. In a second embodiment, the *E. coli* strain is deficient for a lipoprotein of the outer membrane (Δlpp).

iii. Heteromultimeric Protein Purification

In one embodiment, the heteromultimeric protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one embodiment, Protein A immobilized on a solid phase is used for immunoaffinity purification of, for example, full length antibody products of the invention. Protein A is a 41 kD cell wall protein from *Staphylococcus aureus* which binds with a high affinity to the Fc region of antibodies. Lindmark et al. (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. The heteromultimeric protein (e.g., antibody) is recovered from the solid phase by elution.

b. Generating Heteromultimeric Proteins Using Eukaryotic Host Cells:

The vector components generally include, but are not limited to, one or more of the following: a signal sequence, an origin of replication, one or more marker genes, an enhancer element, a promoter, and a transcription termination sequence.

i. Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region is ligated in reading frame to DNA encoding the desired heteromultimeric protein(s) (e.g., antibodies).

ii. Origin of Replication

Generally, an origin of replication component is not needed for mammalian expression vectors. For example, the SV40 origin may typically be used, but only because it contains the early promoter.

iii. Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See, for example, U.S. Pat. No. 4,965,199.

iv. Promoter Component

Expression and cloning vectors usually contain a promoter that is recognized by the host organism and is operably linked to the desired Fc-containing polypeptide(s) (e.g., antibody) nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Desired Fc-containing polypeptide(s) (e.g., antibody) transcription from vectors in mammalian host cells is controlled, for example, by promoters obtained from the genomes of viruses such as, for example, polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

v. Enhancer Element Component

Transcription of DNA encoding the desired Fc-containing polypeptide(s) (e.g., antibody) by higher eukaryotes can be increased by inserting an enhancer sequence into the vector. Many enhancer sequences are now known from mammalian genes (e.g., globin, elastase, albumin, α-fetoprotein, and insulin genes). Also, one may use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) for a description of elements for enhancing activation of eukaryotic promoters. The enhancer may be spliced into the vector at a position 5' or 3' to the antibody polypeptide-encoding sequence, provided that enhancement is achieved, but is generally located at a site 5' from the promoter.

vi. Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

vii. Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for desired Fc-containing polypeptide(s) (e.g., antibody) production and cultured in conventional nutrient media modified as appropriate for inducing promoters, selecting transformants, or amplifying the genes encoding the desired sequences.

viii. Culturing the Host Cells

The host cells used to produce a desired Fc-containing polypeptide(s) (e.g., antibody) of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

ix. Purification of Heteromultimeric Proteins

When using recombinant techniques, the Fc-containing polypeptides can be produced intracellularly, or directly secreted into the medium. If the Fc-containing polypeptide is produced intracellularly, as a first step, the particulate debris, either host cells or lysed fragments, are removed, for example, by centrifugation or ultrafiltration. Where the Fc-containing polypeptide is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The heteromultimer composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt). The production of the heteromultimeric proteins can alternatively or additionally (to any of the foregoing particular methods) comprise dialyzing a solution comprising a mixture of the polypeptides.

x. Antibody Production Using Baculovirus

Recombinant baculovirus may be generated by co-transfecting a plasmid encoding an antibody or antibody fragment and BaculoGold™ virus DNA (Pharmingen) into an insect cell such as a *Spodoptera frugiperda* cell (e.g., Sf9 cells; ATCC CRL 1711) or a *Drosophila melanogaster* S2 cell using, for example, lipofectin (commercially available from GIBCO-BRL). In a particular example, an antibody sequence is fused upstream of an epitope tag contained within a baculovirus expression vector. Such epitope tags include poly-His tags. A variety of plasmids may be employed, including plasmids derived from commercially available plasmids such as pVL1393 (Novagen) or pAcGP67B (Pharmingen). Briefly, the sequence encoding an antibody or a fragment thereof may be amplified by PCR with primers complementary to the 5' and 3' regions. The 5' primer may incorporate flanking (selected) restriction enzyme sites. The product may then be digested with the selected restriction enzymes and subcloned into the expression vector.

After transfection with the expression vector, the host cells (e.g., Sf9 cells) are incubated for 4-5 days at 28° C. and the released virus is harvested and used for further amplifications. Viral infection and protein expression may be performed as described, for example, by O'Reilley et al. (Baculovirus expression vectors: A Laboratory Manual. Oxford: Oxford University Press (1994)).

Expressed poly-His tagged antibody can then be purified, for example, by Ni2+-chelate affinity chromatography as follows. Extracts can be prepared from recombinant virus-infected Sf9 cells as described by Rupert et al. (Nature 362:175-179 (1993)). Briefly, Sf9 cells are washed, resuspended in sonication buffer (25 mL HEPES pH 7.9; 12.5 mM MgCl2; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate; 300 mM NaCl; 10% glycerol pH 7.8) and filtered through a 0.45 μm filter. A Ni2+-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline A280 with loading buffer, at which point fraction collection is started. Next, the column is washed with a secondary wash buffer (50 mM phosphate; 300 mM NaCl; 10% glycerol pH 6.0), which elutes nonspecifically bound protein. After reaching A280 baseline again, the column is developed with a 0 to 500 mM Imidazole gradient in the secondary wash buffer. One mL fractions are collected and analyzed by SDS-PAGE and silver staining or Western blot with Ni2+-NTA-conjugated to alkaline phosphatase (Qiagen). Fractions containing the eluted His10-tagged antibody are pooled and dialyzed against loading buffer.

Alternatively, purification of the antibody can be performed using known chromatography techniques, including for instance, Protein A or protein G column chromatography. In one embodiment, the antibody of interest may be recovered from the solid phase of the column by elution into a solution containing a chaotropic agent or mild detergent. Exemplary chaotropic agents and mild detergents include, but are not limited to, Guanidine-HCl, urea, lithium perchlorate, Arginine, Histidine, SDS (sodium dodecyl sulfate), Tween, Triton, and NP-40, all of which are commercially available.

IV. HETEROMULTIMERIC PROTEIN FORMATION/ASSEMBLY

The formation of the complete heteromultimeric protein involves the reassembly of the first and second Fc-containing polypeptides by disulfide bond formation which in the present invention is referred to as refolding. Refolding includes the association of the first Fc-containing polypeptide with the second Fc-containing polypeptide and the formation of the interchain disulfide bonds. Refolding, also termed renaturing, in the present invention is done in vitro.

The host cells may be cultured using the above described methods either as separate cultures or as a single culture. In one method, the first host cells and second host cells are grown in the same culture vessel (sometimes referred to herein as co-cultured or a mixed culture). In another method, the first and second host cells are grown in separate culture vessels. In one method, the separate cultures are processed separately then mixed/combined prior to disruption of the cellular membrane. In another method, the separate cultures are mixed then processed prior to disruption of the cellular membrane. In one method, the separate cultures are mixed without further processing prior to disruption of the cellular membrane. In one method, the single culture comprising the first and second host cells is processed prior to disruption of the cellular membrane. In another method, the co-cultured cells are not processed prior to disruption of the cellular membrane. Processing of the cells comprises centrifugation and resuspension in an appropriate buffer (e.g., extraction buffer).

Extraction buffers are known in the art and the skilled artisan will be able to determine which buffer to use without undue experimentation.

The host cell membranes are disrupted using methods known in the art. Such methods include cell membrane permeabilization and cell membrane disintegration. Permeablizing the cell membrane refers to rendering the membrane "leaky", e.g., by introducing holes, without destroying the overall integrity of the membrane such that the cell remains viable. In other words, permeabilization provides macromolecular movement across the cellular membrane and preserves cellular structure sufficiently to allow continued cell viability. In contrast, cell membrane disintegration results in the cellular contents being released into the extracellular milieu and cell death.

Methods for disrupting cell membranes include but are not limited to enzymatic lysis, sonication, osmotic shock, passage through a microfluidizer, addition of EDTA, use various detergents, solvents (such as toluene, dimethyl sulfoxide, etc), surfactants (such as Triton-X 100, Tween 20, etc), hypotonic buffers, use of freeze/thaw techniques, electroporation, and passage through a stainless steel ball homogenizer.

Once the Fc-containing polypeptides are released from the cell (either by permeabilization or disintegration) the heteromultimerization domains will drive the association of the heteromultimeric proteins. Inter-chain disulfide formation of the associated Fc-containing polypeptides may proceed with or without the addition of reducing agents. The resultant disulfide linked heteromultimeric protein is then purified. Optionally, it may be formulated for research, diagnostic, therapeutic or other purposes.

V. TARGET MOLECULES

Examples of molecules that may be targeted by a heteromultimeric protein of this invention include, but are not limited to, soluble serum proteins and their receptors and other membrane bound proteins (e.g., adhesins).

In another embodiment the heteromultimeric protein of the invention is capable of binding one, two or more cytokines, cytokine-related proteins, and cytokine receptors selected from the group consisting of BMPI, BMP2, BMP3B (GDFIO), BMP4, BMP6, BMP8, CSFI (M-CSF), CSF2 (GM-CSF), CSF3 (G-CSF), EPO, FGFI (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNAI, IFNA2, IFNA4, IFNA5, IFNA6, IFNA7, IFNBI, IFNG, IFNWI, FELI, FELI (EPSELON), FELI (ZETA), ILIA, ILIB, IL2, IL3, IL4, IL5, IL6, IL7, IL8, IL9, IL10, ILII, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, PDGFA, PDGFB, TGFA, TGFB1, TGFB2, TGFB3, LTA (TNF-b), LTB, TNF (TNF-a), TNFSF4 (OX40 ligand), TNFSF5 (CD40 ligand), TNFSF6 (FasL), TNFSF7 (CD27 ligand), TNFSF8 (CD30 ligand), TNFSF9 (4-1 BB ligand), TNFSFI0 (TRAIL), TNFSF1I (TRANCE), TNFSF12 (APO3L), TNFSF13 (April), TNFSF13B, TNFSF14 (HVEM-L), TNFSF15 (VEGI), TNFSF18, HGF (VEGFD), VEGF, VEGFB, VEGFC, ILIR1, IL1R2, IL1RL1, LL1RL2, IL2RA, IL2RB, IL2RG, IL3RA, IL4R, IL5RA, IL6R, IL7R, IL8RA, IL8RB, IL9R, ILI0RA, ILI0RB, IL1IRA, IL12RB1, IL12RB2, IL13RA1, IL13RA2, IL15RA, IL17R, IL18R1, IL20RA, IL21R, IL22R, IL1HY1, ILIRAP, IL1RAPL1, IL1RAPL2, ILIRN, IL6ST, IL18BP, IL18RAP, IL22RA2, AIFI, HGF, LEP (leptin), PTN, and THPO.

In another embodiment, a target molecule is a chemokine, chemokine receptor, or a chemokine-related protein selected from the group consisting of CCLI (I-309), CCL2 (MCP-1/MCAF), CCL3 (MIP-Ia), CCL4 (MIP-Ib), CCL5 (RANTES), CCL7 (MCP-3), CCL8 (mcp-2), CCLH (eotaxin), CCL13 (MCP-4), CCL15 (MIP-Id), CCL16 (HCC-4), CCL17 (TARC), CCL18 (PARC), CCL19 (MDP-3b), CCL20 (MIP-3a), CCL21 (SLC/exodus-2), CCL22 (MDC/STC-I), CCL23 (MPIF-I), CCL24 (MPIF-2/eotaxin-2), CCL25 (TECK), CCL26 (eotaxin-3), CCL27 (CTACK/ILC), CCL28, CXCLI (GROI), CXCL2 (GRO2), CXCL3 (GR03), CXCL5 (ENA-78), CXCL6 (GCP-2), CXCL9

(MIG), CXCLIO (IP 10), CXCLII (I-TAC), CXCL12 (SDFI), CXCL13, CXCL14, CXCL16, PF4 (CXCL4), PPBP (CXCL7), CX3CL1 (SCYDI), SCYEI, XCLI (lymphotactin), XCL2 (SCM-Ib), BLRI (MDR15), CCBP2 (D6/JAB61), CCRI (CKRI/HM145), CCR2 (mcp-IRB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBII), CCR8 (CMKBR8/TERI/CKR-LI), CCR9 (GPR-9-6), CCRLI (VSHKI), CCRL2 (L-CCR), XCRI (GPR5/CCXCRI), CMKLRI, CMKORI (RDCI), CX3CR1 (V28), CXCR4, GPR2 (CCRIO), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCPIO, CKLFSF2, CKLFSF3, CKLFSF4, CKLFSF5, CKLFSF6, CKLFSF7, CKLFSF8, BDNF, C5R1, CSF3, GRCCIO (CIO), EPO, FY (DARC), GDF5, HDFIA, DL8, PRL, RGS3, RGS13, SDF2, SLIT2, TLR2, TLR4, TREMI, TREM2, and VHL.

In another embodiment the heteromultimeric proteins of the invention are capable of binding one or more targets selected from the group consisting of ABCFI; ACVRI; ACVRIB; ACVR2; ACVR2B; ACVRLI; AD0RA2A; Aggrecan; AGR2; AICDA; AIFI; AIGI; AKAPI; AKAP2; AMH; AMHR2; ANGPTI; ANGPT2; ANGPTL3; ANGPTL4; ANPEP; APC; APOCI; AR; AZGPI (zinc-a-glycoprotein); B7.1; B7.2; BAD; BAFF (BLys); BAGI; BAII; BCL2; BCL6; BDNF; BLNK; BLRI (MDR15); BMPI; BMP2; BMP3B (GDFIO); BMP4; BMP6; BMP8; BMPRIA; BMPRIB; BMPR2; BPAGI (plectin); BRCAI; C19orfIO (IL27w); C3; C4A; C5; C5R1; CANTI; CASP1; CASP4; CAVI; CCBP2 (D6/JAB61); CCLI (1-309); CCLII (eotaxin); CCL13 (MCP-4); CCL15 (MIP-Id); CCL16 (HCC-4); CCL17 (TARC); CCL18 (PARC); CCL19 (MIP-3b); CCL2 (MCP-1); MCAF; CCL20 (MIP-3a); CCL21 (MTP-2); SLC; exodus-2; CCL22 (MDC/STC-I); CCL23 (MPIF-1); CCL24 (MPIF-2/eotaxin-2); CCL25 (TECK); CCL26 (eotaxin-3); CCL27 (CTACK/ILC); CCL28; CCL3 (MTP-Ia); CCL4 (MDP-Ib); CCL5 (RANTES); CCL7 (MCP-3); CCL8 (mcp-2); CCNAI; CCNA2; CCNDI; CCNEI; CCNE2; CCRI (CKRI/HM145); CCR2 (mcp-IRB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBII); CCR8 (CMKBR8/TERI/CKR-LI); CCR9 (GPR-9-6); CCRLI (VSHKI); CCRL2 (L-CCR); CD164; CD19; CDIC; CD20; CD200; CD22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDHI (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKNIA (p21Wapl/CipI); CDKNIB (p27KipI); CDKNIC; CDKN2A (P16INK4a); CDKN2B; CDKN2C; CDKN3; CEBPB; CERI; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLRI; CMKORI (RDCI); CNRI; COL18A1; COLIAI; COL4A3; COL6A1; CR2; CRP; CSFI (M-CSF); CSF2 (GM-CSF); CSF3 (GCSF); CTLA4; CTNNBI (b-catenin); CTSB (cathepsin B); CX3CL1 (SCYDI); CX3CR1 (V28); CXCLI (GROI); CXCL10 (IP-10); CXCLII (1-TAC/IP-9); CXCL12 (SDFI); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYCI; CYSLTRI; DAB2IP; DES; DKFZp451J0118; DNCLI; DPP4; E2F1; ECGFI; EDGI; EFNAI; EFNA3; EFNB2; EGF; EGFR; ELAC2; ENG; ENO1; ENO2; ENO3; EPHB4; EPO; ERBB2 (Her-2); EREG; ERK8; ESRI; ESR2; F3 (TF); FADD; FasL; FASN; FCERIA; FCER2; FCGR3A; FGF; FGFI (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FELI (EPSILON); FILI (ZETA); FLJ12584; FLJ25530; FLRTI (fibronectin); FLTI; FOS; FOSLI (FRA-I); FY (DARC); GABRP (GABAa); GAGEBI; GAGECI; GALNAC4S-6ST; GATA3; GDF5; GFI1; GGT1; GM-CSF; GNASI; GNRHI; GPR2 (CCRIO); GPR31; GPR44; GPR81 (FKSG80); GRCCIO (CIO); GRP; GSN (Gelsolin); GSTPI; HAVCR2; HDAC4; HDAC5; HDAC7A; HDAC9; HGF; HIFIA; HDPI; histamine and histamine receptors; HLA-A; HLA-DRA; HM74; HMOXI; HUMCYT2A; ICEBERG; ICOSL; ID2; IFN-a; IFNAI; IFNA2; IFNA4; IFNA5; IFNA6; IFNA7; IFNB1; IFNgamma; DFNWI; IGBPI; IGFI; IGFIR; IGF2; IGFBP2; IGFBP3; IGFBP6; IL-I; IL10; IL10RA; IL10RB; IL11; IL11 RA; IL-12; IL12A; IL12B; IL12RB1; IL12RB2; 1L13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; ILIF10; IL1F5; IL1F6; IL1F7; IL1F8; IL1F9; IL1HYI; IL1RI; IL1R2; IL1RAP; IL1RAPL1, IL1RAPL2, IL1RL1, IL1RL2, ILIRN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); EL7; EL7R; EL8; IL8RA; DL8RB; IL8RB; DL9; DL9R; DLK; INHA; INHBA; INSL3; INSL4; IRAKI; ERAK2; ITGAI; ITGA2; ITGA3; ITGA6 (a6 integrin); ITGAV; ITGB3; ITGB4 (b 4 integrin); JAGI; JAKI; JAK3; JUN; K6HF; KAII; KDR; KITLG; KLF5 (GC Box BP); KLF6; KLKIO; KLK12; KLK13; KLK14; KLK15; KLK3; KLK4; KLK5; KLK6; KLK9; KRT1; KRT19 (Keratin 19); KRT2A; KHTHB6 (hair-specific type H keratin); LAMAS; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIBI; midkine; MEF; MIP-2; MKI67; (Ki-67); MMP2; MMP9; MS4A1; MSMB; MT3 (metallothionectin-III); MTSSI; MUCI (mucin); MYC; MYD88; NCK2; neurocan; NFKBI; NFKB2; NGFB (NGF); NGFR; NgR-Lingo; NgR-Nogo66 (Nogo); NgR-p75; NgR-Troy; NMEI (NM23A); N0X5; NPPB; NROBI; NR0B2; NRIDI; NR1 D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRPI; NRP2; NT5E; NTN4; ODZI; OPRDI; P2RX7; PAP; PARTI; PATE; PAWR; PCA3; PCNA; PDGFA; PDGFB; PECAMI; PF4 (CXCL4); PGF; PGR; phosphacan; PIAS2; PIK3CG; PLAU (uPA); PLG; PLXDCI; PPBP (CXCL7); PPID; PRI; PRKCQ; PRKDI; PRL; PROC; PROK2; PSAP; PSCA; PTAFR; PTEN; PTGS2 (COX-2); PTN; RAC2 (p21Rac2); RARB; RGSI; RGS13; RGS3; RNFIIO (ZNF144); ROBO2; S100A2; SCGB1D2 (lipophilin B); SCGB2A1 (mammaglobin 2); SCGB2A2 (mammaglobin 1); SCYEI (endothelial Monocyte-activating cytokine); SDF2; SERPINAI; SERPINA3; SERP1 NB5 (maspin); SERPINEI (PAI-I); SERPDMF1; SHBG; SLA2; SLC2A2; SLC33A1; SLC43A1; SLIT2; SPPI; SPRRIB (SprI); ST6GAL1; STABI; STAT6; STEAP; STEAP2; TB4R2; TBX21; TCPIO; TDGFI; TEK; TGFA; TGFBI; TGFBIII; TGFB2; TGFB3; TGFBI; TGFBRI; TGFBR2; TGFBR3; THIL; THBSI (thrombospondin-1); THBS2; THBS4; THPO; TIE (Tie-1); TMP3; tissue factor;

TLRIO; TLR2; TLR3; TLR4; TLR5; TLR6; TLR7; TLR8; TLR9; TNF; TNF-a; TNFAEP2 (B94); TNFAIP3; TNFRSFIIA; TNFRSFIA; TNFRSFIB; TNFRSF21; TNFRSF5; TNFRSF6 (Fas); TNFRSF7; TNFRSF8; TNFRSF9; TNFSFIO (TRAIL); TNFSFI 1 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1 BB ligand); TOLLIP; Toll-like receptors; TOP2A (topoisomerase Ea); TP53; TPMI; TPM2; TRADD; TRAFI; TRAF2; TRAF3; TRAF4; TRAF5; TRAF6; TREMI; TREM2; TRPC6; TSLP; TWEAK; VEGF; VEGFB; VEGFC; versican; VHL C5; VLA-4; XCLI (lymphotactin); XCL2 (SCM-Ib); XCRI(GPR5/CCXCRI); YYI; and ZFPM2.

Preferred molecular target molecules for antibodies encompassed by the present invention include CD proteins such as CD3, CD4, CD8, CD16, CD19, CD20, CD34; CD64, CD200 members of the ErbB receptor family such as the EGF receptor, HER2, HER3 or HER4 receptor; cell adhesion molecules such as LFA-1, Mac1, p150.95, VLA-4, ICAM-1, VCAM, alpha4/beta7 integrin, and alphav/beta3 integrin including either alpha or beta subunits thereof (e.g., anti-CD11a, anti-CD18 or anti-CD11b antibodies); growth factors such as VEGF-A, VEGF-C; tissue factor (TF); alpha interferon (alphaIFN); TNFalpha, an interleukin, such as IL-1beta, IL-3, IL-4, IL-5, IL-8, IL-9, IL-13, IL17A/F, IL-18, IL-13Ralpha1, IL13Ralpha2, IL-4R, IL-5R, IL-9R, IgE; blood group antigens; flk2/flt3 receptor; obesity (OB) receptor; mpI receptor; CTLA-4; RANKL, RANK, RSV F protein, protein C etc.

In one embodiment, the heteromultimeric proteins of this invention bind low-density lipoprotein receptor-related protein (LRP)-1 or LRP-8 or transferrin receptor, and at least one target selected from the group consisting of 1) beta-secretase (BACE1 or BACE2), 2) alpha-secretase, 3) gamma-secretase, 4) tau-secretase, 5) amyloid precursor protein (APP), 6) death receptor 6 (DR6), 7) amyloid beta peptide, 8) alpha-synuclein, 9) Parkin, 10) Huntingtin, 11) p75 NTR, and 12) caspase-6.

In one embodiment, the heteromultimeric proteins of this invention binds to at least two target molecules selected from the group consisting of: IL-Ialpha and IL-Ibeta, IL-12 and IL-18; IL-13 and IL-9; IL-13 and IL-4; IL-13 and IL-5; IL-5 and IL-4; IL-13 and IL-Ibeta; IL-13 and IL-25; IL-13 and TARC; IL-13 and MDC; IL-13 and MEF; IL-13 and TGF-β; IL-13 and LHR agonist; IL-12 and TWEAK, IL-13 and CL25; IL-13 and SPRR2a; IL-13 and SPRR2b; IL-13 and ADAM8, IL-13 and PED2, IL17A and IL17F, CD3 and CD19, CD138 and CD20; CD138 and CD40; CD19 and CD20; CD20 and CD3; CD38 and CD138; CD38 and CD20; CD38 and CD40; CD40 and CD20; CD-8 and IL-6; CD20 and BR3, TNFalpha and TGF-beta, TNFalpha and IL-Ibeta; TNFalpha and IL-2, TNF alpha and IL-3, TNFalpha and IL-4, TNFalpha and IL-5, TNFalpha and IL6, TNFalpha and IL8, TNFalpha and IL-9, TNFalpha and IL-10, TNFalpha and IL-11, TNFalpha and IL-12, TNFalpha and IL-13, TNFalpha and IL-14, TNFalpha and IL-15, TNFalpha and IL-16, TNFalpha and IL-17, TNFalpha and IL-18, TNFalpha and IL-19, TNFalpha and IL-20, TNFalpha and IL-23, TNFalpha and IFNalpha, TNFalpha and CD4, TNFalpha and VEGF, TNFalpha and MIF, TNFalpha and ICAM-1, TNFalpha and PGE4, TNFalpha and PEG2, TNFalpha and RANK ligand, TNFalpha and Te38; TNFalpha and BAFF; TNFalpha and CD22; TNFalpha and CTLA-4; TNFalpha and GP130; TNFα and IL-12p40; VEGF and HER2, VEGF-A and HER2, VEGF-A and PDGF, HER1 and HER2, VEGF-A and VEGF-C, VEGF-C and VEGF-D, HER2 and DR5, VEGF and IL-8, VEGF and MET, VEGFR and MET receptor, VEGFR and EGFR, HER2 and CD64, HER2 and CD3, HER2 and CD16, HER2 and HER3; EGFR(HER1) and HER2, EGFR and HER3, EGFR and HER4, IL-13 and CD40L, IL4 and CD40L, TNFR1 and IL-1R, TNFR1 and IL-6R and TNFR1 and IL-18R, EpCAM and CD3, MAPG and CD28, EGFR and CD64, CSPGs and RGM A; CTLA-4 and BTNO2; IGF1 and IGF2; IGF1/2 and Erb2B; MAG and RGM A; NgR and RGM A; NogoA and RGM A; OMGp and RGM A; PDL-I and CTLA-4; and RGM A and RGM B.

Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule. Other antigens and forms thereof useful for preparing antibodies will be apparent to those in the art.

VI. ACTIVITY ASSAYS

The heteromultimeric proteins of the present invention can be characterized for their physical/chemical properties and biological functions by various assays known in the art.

The purified heteromultimeric proteins can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the immunoglobulins produced herein are analyzed for their biological activity. In some embodiments, the immunoglobulins of the present invention are tested for their antigen binding activity. The antigen binding assays that are known in the art and can be used herein include, without limitation, any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. An illustrative antigen binding assay is provided below in the Examples section.

In one embodiment, the present invention contemplates an altered antibody that possesses some but not all effector functions, which make it a desired candidate for many applications in which the half life of the antibody in vivo is important yet certain effector functions (such as complement and ADCC) are unnecessary or deleterious. In certain embodiments, the Fc activities of the produced heteromultimeric protein are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the heteromultimeric protein lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol* 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and natural killer (NK) cells. Alternatively, or additionally, ADCC activity of the molecule of interest may be assessed in vivo, e.g., in a animal model such as that disclosed in Clynes et al. *PNAS* (USA) 95:652-656 (1998). C1q binding assays may also be carried out to confirm that the antibody is unable to bind C1q and hence lacks CDC activity. To assess complement activation, a CDC assay, e.g. as described in Gazzano-Santoro et al., *J. Immunol. Methods* 202:163 (1996), may be performed. FcRn binding and in vivo clearance/half life determinations can also be performed using methods known in the art.

VII. CONJUGATED PROTEINS

The invention also provides conjugated proteins such as conjugated antibodies or immunoconjugates (for example, "antibody-drug conjugates" or "ADC"), comprising any of the heteromultimeric proteins described herein (e.g., an antibody made according to the methods described herein) where one of the constant regions of the light chain or the heavy chain is conjugated to a chemical molecule such as a dye or cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In particular, as described herein, the use of heteromultimerization domains enables the construction of antibodies containing two different heavy chains (HC1 and HC2) as well as two different light chains (LC1 and LC2). An immunoconjugate constructed using the methods described herein may contain the cytotoxic agent conjugated to a constant region of only one of the heavy chains (HC1 or HC2) or only one of the light chains (LC1 or LC2). Also, because the immunoconjugate can have the cytotoxic agent attached to only one heavy or light chain, the amount of the cytotoxic agent being administered to a subject is reduced relative to administration of an antibody having the cytotoxic agent attached to both heavy or light chains. Reducing the amount of cytotoxic agent being administered to a subject limits adverse side effects associated with the cytotoxic agent.

The use of antibody-drug conjugates for the local delivery of cytotoxic or cytostatic agents, i.e., drugs to kill or inhibit tumor cells in the treatment of cancer (Syrigos and Epenetos, Anticancer Research 19:605-614 (1999); Niculescu-Duvaz and Springer, Adv. Drg. Del. Rev. 26:151-172 (1997); U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., Lancet (Mar. 15, 1986):603-605 (1986); Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., Cancer Immunol. Immunother. 21:183-187 (1986)). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al., Jour. of the Nat. Cancer Inst. 92(19):1573-1581 (2000); Mandler et al., Bioorganic & Med. Chem. Letters 10:1025-1028 (2000); Mandler et al., Bioconjugate Chem. 13:786-791 (2002)), maytansinoids (EP 1391213; Liu et al., Proc. Natl. Acad. Sci. USA 93:8618-8623 (1996)), and calicheamicin (Lode et al., Cancer Res. 58:2928 (1998); Hinman et al., Cancer Res. 53:3336-3342 (1993)). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

i. Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. Patent Application Publication No. 2005/0169933, the disclosures of which are hereby expressly incorporated by reference. Antibody-maytansinoid conjugates comprising the linker component SMCC may be prepared as disclosed in U.S. Patent Application Publication No. 2005/0169933. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

ii. Auristatins and Dolastatins

In some embodiments, the immunoconjugate comprises an antibody of the invention conjugated to dolastatins or dolostatin peptidic analogs and derivatives, the auristatins (U.S. Pat. Nos. 5,635,483 and 5,780,588). Dolastatins and auristatins have been shown to interfere with microtubule dynamics, GTP hydrolysis, and nuclear and cellular division (Woyke et al., Antimicrob. Agents and Chemother. 45(12): 3580-3584 (2001)) and have anticancer (U.S. Pat. No. 5,663,149) and antifungal activity (Pettit et al., Antimicrob. Agents Chemother. 42:2961-2965 (1998)). The dolastatin or auristatin drug moiety may be attached to the antibody through the N-(amino) terminus or the C-(carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Application Publication No. 2005/0238649, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides," volume 1, pp. 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit et al., J. Nat. Prod. 44:482-485 (1981); Pettit et al., Anti-Cancer Drug Design 13:47-66 (1998); Poncet, Curr. Pharm. Des. 5:139-162 (1999); and Pettit, Fortschr. Chem. Org. Naturst. 70:1-79 (1997). See also Doronina, Nat. Biotechnol. 21(7):778-784 (2003); and "Monomethylvaline Compounds Capable of Conjugation to Ligands," U.S. Application Publication No. 2005/0238649, hereby incorporated by reference in its entirety (disclosing, e.g., linkers and methods of preparing monomethylvaline compounds such as MMAE and MMAF conjugated to linkers).

iii. Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA, which is an antifolate. Both calicheamicin and QFA have intracellular sites of action and do not readily cross the plasma membrane. Therefore, cellular uptake of these agents through antibody mediated internalization greatly enhances their cytotoxic effects.

iv. Other Cytotoxic Agents

Other antitumor agents that can be conjugated to the antibodies of the invention or made according to the methods described herein include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes (see, for example, WO 93/21232, published Oct. 28, 1993).

The present invention further contemplates an immunoconjugate formed between an antibody and a compound with nucleolytic activity (e.g., a ribonuclease or a DNA endonuclease such as a deoxyribonuclease; DNase).

For selective destruction of a tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al., Biochem. Biophys. Res. Commun. 80:49-57 (1978)) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

v. Preparation of Conjugated Antibodies

In the conjugated antibodies of the invention, an antibody is conjugated to one or more moieties (for example, drug moieties), e.g., about 1 to about 20 moieties per antibody, optionally through a linker. The conjugated antibodies may be prepared by several routes, employing organic chemistry reactions, conditions, and reagents known to those skilled in the art, including: (1) reaction of a nucleophilic group of an antibody with a bivalent linker reagent via a covalent bond, followed by reaction with a moiety of interest; and (2) reaction of a nucleophilic group of a moiety with a bivalent linker reagent via a covalent bond, followed by reaction with the nucleophilic group of an antibody. Additional methods for preparing conjugated antibodies are described herein.

The linker reagent may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC'), and N-Succinimidyl (4-iodo-acetyl) aminobenzoate ("SIAB"). Additional linker components are known in the art and some are described herein. See also "Monomethylvaline Compounds Capable of Conjugation to Ligands," U.S. Application Publication No. 2005/0238649, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e., cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Conjugated antibodies of the invention may also be produced by modification of the antibody to introduce electrophilic moieties, which can react with nucleophilic substituents on the linker reagent or drug or other moiety. The sugars of glycosylated antibodies may be oxidized, e.g., with periodate oxidizing reagents, to form aldehyde or ketone groups which may react with the amine group of linker reagents or drug or other moieties. The resulting imine Schiff base groups may form a stable linkage, or may be reduced, e.g., by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug or other moiety (Hermanson, Bioconjugate Techniques). In another embodiment, proteins containing N-terminal serine or threonine residues can react with sodium meta-periodate, resulting in production of an aldehyde in place of the first amino acid (Geoghegan and Stroh, Bioconjugate Chem. 3:138-146 (1992); U.S. Pat. No. 5,362,852). Such aldehyde can be reacted with a drug moiety or linker nucleophile.

Likewise, nucleophilic groups on a moiety (such as a drug moiety) include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate. In yet another embodiment, the antibody may be conjugated to a "receptor" (such streptavidin) for utilization in tumor pre-targeting wherein the antibody-receptor conjugate is administered to the individual, followed by removal of unbound conjugate from the circulation using a clearing agent and then administration of a "ligand" (e.g., avidin) which is conjugated to a cytotoxic agent (e.g., a radionucleotide).

VIII. UTILITY

The present Fc variant polypeptides described herein find industrial applicability in the production of heteromultimeric proteins.

The heteromultimeric proteins described herein find use in, for example, in vitro, ex vivo and in vivo therapeutic methods. The invention provides various methods based on using one or more of these molecules. In certain pathological conditions, it is necessary and/or desirable to utilize heteromultimeric proteins, e.g., multispecific antibodies. The invention provides these heteromultimeric proteins, which can be used for a variety of purposes, for example as therapeutics, prophylactics and diagnostics. For example, the invention provides methods of treating a disease, said methods comprising administering to a subject in need of treatment a heteromultimeric protein of the invention, whereby the disease is treated. Any of the heteromultimeric proteins of the invention described herein can be used in therapeutic (or prophylactic or diagnostic) methods described herein.

For example, when the heteromultimeric protein is multivalent, a valuable benefit is the enhanced avidity they pose for their antigen. In addition to having intrinsic high affinity on a binding unit (ie, a Fab) to antigen basis, normal IgG antibodies also exploit the avidity effect to increase their association with antigens as a result of their bivalent binding towards the targets.

A heteromultimeric protein directed against two separate epitopes on the same antigen molecule may not only provide the benefit of enhanced binding avidity (because of bivalent binding), but may also acquire novel properties that are not associated with either of the parent antibodies. Thus, the heteromultimeric proteins of the invention find use in, for example, the blocking of receptor-ligand interactions.

The heteromultimeric proteins described herein also find use in the application of simultaneously blocking the signaling pathways of two targets with one molecule.

IX. THERAPEUTIC USES

The heteromultimeric proteins such as antibodies and antibody fragments described herein (e.g., an antibody and/or fragment thereof made according to the methods described herein) may be used for therapeutic applications. For example, such heteromultimeric proteins can be used for the treatment of tumors, including pre-cancerous, non-metastatic, metastatic, and cancerous tumors (e.g., early stage cancer), for the treatment of allergic or inflammatory disorders, or for the treatment of autoimmune disease, or for the treatment of a subject at risk for developing cancer (for example, breast cancer, colorectal cancer, lung cancer, renal cell carcinoma, glioma, or ovarian cancer), an allergic or inflammatory disorder, or an autoimmune disease.

The term cancer embraces a collection of proliferative disorders, including but not limited to pre-cancerous growths, benign tumors, and malignant tumors. Benign tumors remain localized at the site of origin and do not have the capacity to infiltrate, invade, or metastasize to distant sites. Malignant tumors will invade and damage other tissues around them. They can also gain the ability to break off from where they started and spread to other parts of the body (metastasize), usually through the bloodstream or through the lymphatic system where the lymph nodes are located. Primary tumors are classified by the type of tissue from which they arise; metastatic tumors are classified by the tissue type from which the cancer cells are derived. Over time, the cells of a malignant tumor become more abnormal and appear less like normal cells. This change in the appearance of cancer cells is called the tumor grade and cancer cells are described as being well-differentiated, moderately-differentiated, poorly-differentiated, or undifferentiated. Well-differentiated cells are quite normal appearing and resemble the normal cells from which they originated. Undifferentiated cells are cells that have become so abnormal that it is no longer possible to determine the origin of the cells.

The tumor can be a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia), or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further separated into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin. Solid tumors of non-epithelial origin include sarcomas, brain tumors, and bone tumors.

Epithelial cancers generally evolve from a benign tumor to a preinvasive stage (e.g., carcinoma in situ), to a malignant cancer, which has penetrated the basement membrane and invaded the subepithelial stroma.

Multispecific protein complexes can also be used in these therapeutic applications, and antibodies that bind HER2 can in particular be used to treat breast cancer, colorectal cancer, lung cancer, renal cell carcinoma, glioma, or ovarian cancer.

Other subjects that are candidates for receiving compositions of this invention have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu), osteoarthritis, Paget's disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sogren's syndrome, solid tumors, Stargart's disease, Steven's Johnson disease, superior limbic keratitis, syphilis, systemic lupus, Terrien's marginal degeneration, toxoplasmosis, tumors of Ewing sarcoma, tumors of neuroblastoma, tumors of osteosarcoma, tumors of retinoblastoma, tumors of rhabdomyosarcoma, ulcerative colitis, vein occlusion, Vitamin A deficiency, Wegener's sarcoidosis, undesired angiogenesis associated with diabetes, parasitic diseases, abnormal wound healing, hypertrophy following surgery, injury or trauma (e.g., acute lung injury/ARDS), inhibition of hair growth, inhibition of ovulation and corpus luteum formation, inhibition of implantation, and inhibition of embryo development in the uterus.

Examples of allergic or inflammatory disorders or autoimmune diseases or disorders that may be treated using an antibody made according to the methods described herein include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and autoimmune asthma, conditions involving infiltration of T-cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extrarenal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia areata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as Leishmania, toxic-shock syndrome, food poisoning, conditions involving infiltration of T-cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

In addition to therapeutic uses, the antibodies of the invention can be used for other purposes, including diagnostic methods, such as diagnostic methods for the diseases and conditions described herein.

X. DOSAGES, FORMULATIONS, AND DURATION

The proteins of this invention will be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The "therapeutically effective amount" of the proteins to be administered will be governed by such considerations, and is the minimum amount necessary to prevent, ameliorate, or treat a particular disorder (for example, a cancer, allergic or inflammatory disorder, or autoimmune disorder). The proteins need not be, but are optionally, formulated with one or more agents currently used to prevent or treat the disorder. The effective amount of such other agents depends on the amount of proteins present in the formulation, the type of disorder or treatment, and other factors discussed above. These are generally used in the same dosages and with administration routes as used hereinbefore or about from 1 to 99% of the heretofore employed dosages. Generally, alleviation or treatment of a cancer involves the lessening of one or more symptoms or medical problems associated with the cancer. The therapeutically effective amount of the drug can accomplish one or a combination of the following: reduce (by at least 10%, 20%, 30%, 40%, 50%, 60%, 70%, 80%, 90%, 100% or more) the number of cancer cells; reduce or inhibit the tumor size or tumor burden; inhibit (i.e., to decrease to some extent and/or stop) cancer cell infiltration into peripheral organs; reduce hormonal secretion in the case of adenomas; reduce vessel density; inhibit tumor metastasis; reduce or inhibit tumor growth; and/or relieve to some extent one or more of the symptoms associated with the cancer. In some embodiments, the proteins are used to prevent the occurrence or reoccurrence of cancer or an autoimmune disorder in the subject.

In one embodiment, the present invention can be used for increasing the duration of survival of a human subject susceptible to or diagnosed with a cancer or autoimmune disorder. Duration of survival is defined as the time from first administration of the drug to death. Duration of survival can also be measured by stratified hazard ratio (HR) of the treatment group versus control group, which represents the risk of death for a subject during the treatment.

In yet another embodiment, the treatment of the present invention significantly increases response rate in a group of human subjects susceptible to or diagnosed with a cancer who are treated with various anti-cancer therapies. Response rate is defined as the percentage of treated subjects who responded to the treatment. In one embodiment, the combination treatment of the invention using proteins of this invention and surgery, radiation therapy, or one or more chemotherapeutic agents significantly increases response rate in the treated subject group compared to the group treated with surgery, radiation therapy, or chemotherapy alone, the increase having a Chi-square p-value of less than 0.005. Additional measurements of therapeutic efficacy in the treatment of cancers are described in U.S. Patent Application Publication No. 20050186208.

Therapeutic formulations are prepared using standard methods known in the art by mixing the active ingredient having the desired degree of purity with optional physiologically acceptable carriers, excipients or stabilizers (Remington's Pharmaceutical Sciences (20$^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the heteromultimeric protein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated heteromultimeric protein(s) remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The proteins described herein (e.g., a heteromultimeric protein such as a multispecific antibody made according to the methods described herein) are administered to a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration may be particularly desired if extensive side effects or toxicity is associated with antagonism to the target molecule recognized by the proteins. An ex vivo strategy can also be used for therapeutic applications. Ex vivo strategies involve transfecting or transducing cells obtained from the subject with a polynucleotide encoding a protein of this invention. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

In one example, the protein complex is (e.g., a heteromultimeric protein such as a multispecific antibody made according to the methods described herein) is administered locally, e.g., by direct injections, when the disorder or location of the tumor permits, and the injections can be repeated periodically. The protein complex can also be delivered systemically to the subject or directly to the tumor cells, e.g., to a tumor or a tumor bed following surgical excision of the tumor, in order to prevent or reduce local recurrence or metastasis.

XI. ARTICLES OF MANUFACTURE

Another embodiment of the invention is an article of manufacture containing one or more protein complexes described herein, and materials useful for the treatment or diagnosis of a disorder (for example, an autoimmune disease or cancer). The article of manufacture comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). At least one active agent in the composition is a heteromultimeric protein (e.g., an antibody or antibody fragment) of the invention. The label or package insert indicates that the composition is used for treating the particular condition. The label or package insert will further comprise instructions for administering the heteromultimeric protein composition to the subject. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In certain embodiments, the package insert indicates that the composition is used for treating breast cancer, colorectal cancer, lung cancer, renal cell carcinoma, glioma, or ovarian cancer.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials considered from a commercial and user standpoint, including other buffers, diluents, filters, needles, and syringes.

Kits are also provided that are useful for various purposes, e.g., for purification or immunoprecipitation of an antigen (e.g., HER2 or EGFR) from cells. For isolation and purification of an antigen (e.g., HER2 or EGFR) the kit can contain a heteromultimeric protein (e.g., an EGFR/HER2 antibody) coupled to beads (e.g., sepharose beads). Kits can be provided which contain the heteromultimeric protein(s) for detection and quantitation of the antigen in vitro, e.g., in an ELISA or a Western blot. As with the article of manufacture, the kit comprises a container and a label or package insert on or associated with the container. The container holds a composition comprising at least one heteromultimeric protein (e.g., multispecific antibody or antibody fragment) of the invention. Additional containers may be included that contain, e.g., diluents and buffers or control antibodies. The label or package insert may provide a description of the composition as well as instructions for the intended in vitro or diagnostic use.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds); ADCC (antibody-dependent cellular cytotoxicity)); BsAb (bispecific antibody); $C_L$ (constant domain of light chain); $C_H$ (constant domain of heavy chain); CMC (complement-mediated cytotoxicity); Fab (antigen binding fragment); Fc (crystallized fragment); Fv (variable fragment ($V_L+V_H$)); EGFR (epidermal growth factor receptor); HC (heavy chain); IGFR (insulin-like growth factor receptor); LC (light chain); scFv (singlechain variable fragment ($V_L$ and $V_H$ tethered by an amino acid linker); VEGF (vascular endothelial growth factor); VEGFR2 (vascular endothelial growth factor receptor 2); $V_H$ (variable heavy domain); $V_L$ (variable light domain).

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

Construction of Expression Vectors

This example illustrates the nucleic acid construct used to transform host cells.

Figure 2A:
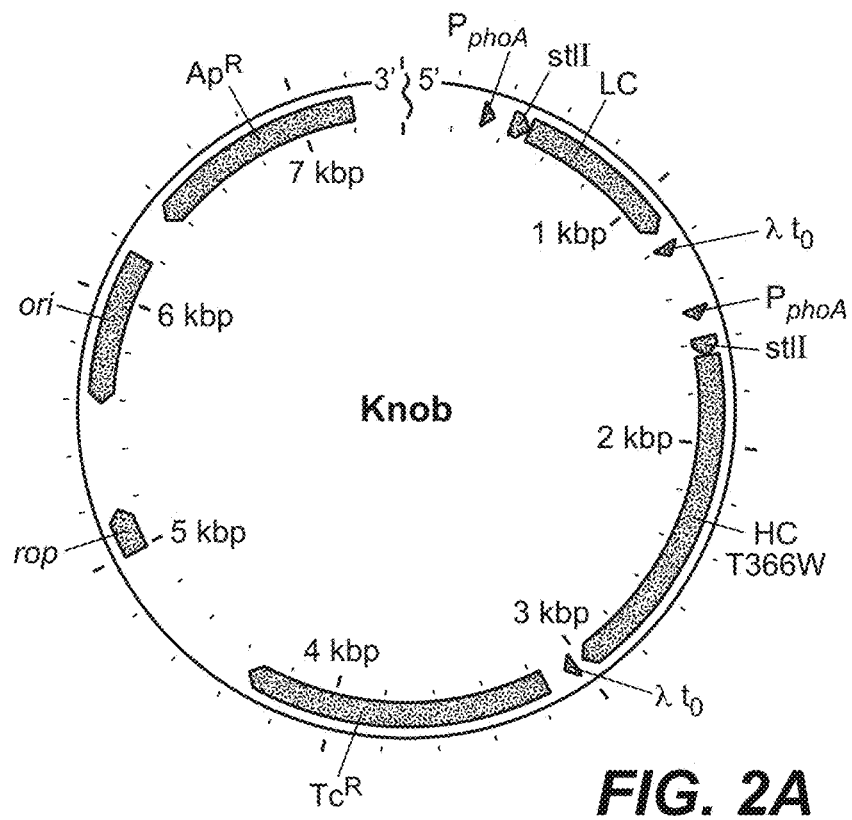
FIGS. 2A & B illustrates plasmids encoding the knob and hole half-antibodies, respectively.
Figure 2B:
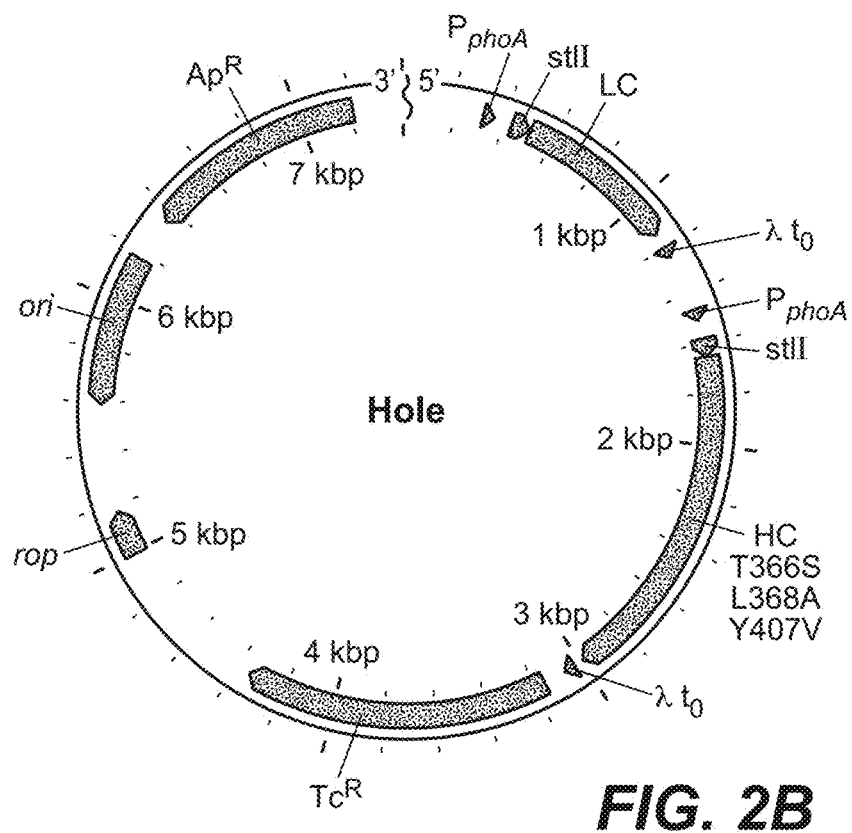

Generally, both the heavy and light chain DNA coding sequences were cloned into an expression plasmid that contained separate promoter elements for each of the sequences and antibiotic resistance for selection of bacterial cells that contain the expression plasmid. The vector constructs also encode the heat-stable enterotoxin II (STII) secretion signal (Picken et al., 1983, Infect. Immun. 42:269-275, and Lee et al., 1983, Infect. Immun. 42:264-268) for the export of the antibody polypeptides into the periplasmic space of the bacterial cell. Transcription of each chain is controlled by the phoA promoter (Kikuchi et al., 1981, Nucleic Acids Res., 9:5671-5678) and translational control is provided by previously described STII signal sequence variants of measured relative translational strength, which contain silent codon changes in the translation initiation region (TIR) (Simmons and Yansura, 1996, Nature Biotechnol. 14:629-634 and Simmons et al., 2002, J. Immunol Methods, 263:133-147). A schematic drawing of the knob and hole plasmids is shown in FIGS. 2A and 2B, respectively.

While the present invention does not rely on specific antibody binding sequences, and is applicable to any half-antibody combinations, the Examples herein are directed to heteromultimeric antibodies directed to c-met, EGFR, IL-4 and IL-13. Examples of anti-c-met antibodies are given in U.S. Pat. Nos. 7,472,724, and 7,498,420. Examples of anti-EGFR antibodies are given in U.S. Provisional Application 61/210,562 (filed 20 Mar. 2009), US Pat. Appln. Pub. No. 20080274114 (published 6 Nov. 2008) and U.S. Pat. No. 5,844,093 (granted 1 Dec. 1998). Examples of anti-IL-13 antibodies are described in U.S. Pat. No. 7,501,121 (granted 10 Mar. 2009), U.S. Pat. No. 7,615,213 (granted 10 Nov. 2009), WO 2006/085938 (published 17 Aug. 2006), US Pat Appln. Pub. No. 20090214523 (published 27 Aug. 2009), and U.S. Pat. No. 7,674,459 (granted 9 Mar. 2010). Examples of anti-IL-4 antibodies are described in US Pat. Appln. Pub. No. US 20080241160 (published 2 Oct. 2008), and U.S. Pat. No. 6,358,509 (granted 19 Mar. 2002).

Each half-antibody had either a knob (protuberance) or a hole (cavity) engineered into the heavy chain as described in U.S. Pat. No. 7,642,228. Briefly, a $C_H3$ knob mutant was generated first. A library of $C_H3$ hole mutants was then created by randomizing residues 366, 368 and 407 that are in proximity to the knob on the partner $C_H3$ domain. In the following examples, the knob mutation is T366W, and the hole has mutations T366S, L368A and Y407V in an IgG1 backbone. Equivalent mutations in other immunoglobulin isotypes is easily determined by one skilled in the art. Further, the skilled artisan will readily appreciate that it is preferred that the two half-antibodies used for the bispecific be the same isotype. Half-antibodies of different isotypes may be used but may need further mutations.

In some instances each half-antibody had further mutations introduced at residues F241 and F243 in the $C_H2$ domains. Point mutations were introduced using known techniques in the art to change the wild-type phenylalanine to either a serine or arginine so that the combination was either F241 S/F243R or F241R/F243S.

Although the vector described in this Example is for either the anti-c-Met or anti-EGFR half-antibody, one skilled in the art will readily appreciate that any antibody can be encoded in the plasmid. The starting plasmid for all constructs used herein is the previously described anti-tissue factor separate cistron plasmid, paTF50, with relative TIRs of 1 for heavy and 1 for light (Simmons et al., 2002, J. Immunol Methods, 263:133-147, and U.S. Pat. No. 6,979, 556). An increase in the relative TIR strengths was used to increase the expression titers of these half-antibodies.

Example 2

Heteromultimeric Protein Production Using Separate Cell Cultures

The following example shows the production of heteromultimeric proteins when the cells expressing the monomeric components (e.g., a half-antibody) are grown in separate cultures. In this method the cells are grown and induced to express the half-antibody in separate cultures. In this method the components may be purified first and then combined to form the heteromultimeric protein.

In this method, a nucleic acid encoding the first Fc-containing polypeptide (e.g., a half-antibody (knob)) is introduced into a first host cell and a nucleic acid encoding the second Fc-containing polypeptide (e.g., a half-antibody (hole)) is introduced into a second host cell. Although this example illustrates the formation of a BsAb one skilled in the art will readily appreciate that the methods described are applicable to any heteromultimeric protein comprising a hinge region, e.g., affibodies, etc.

Figure 4A:
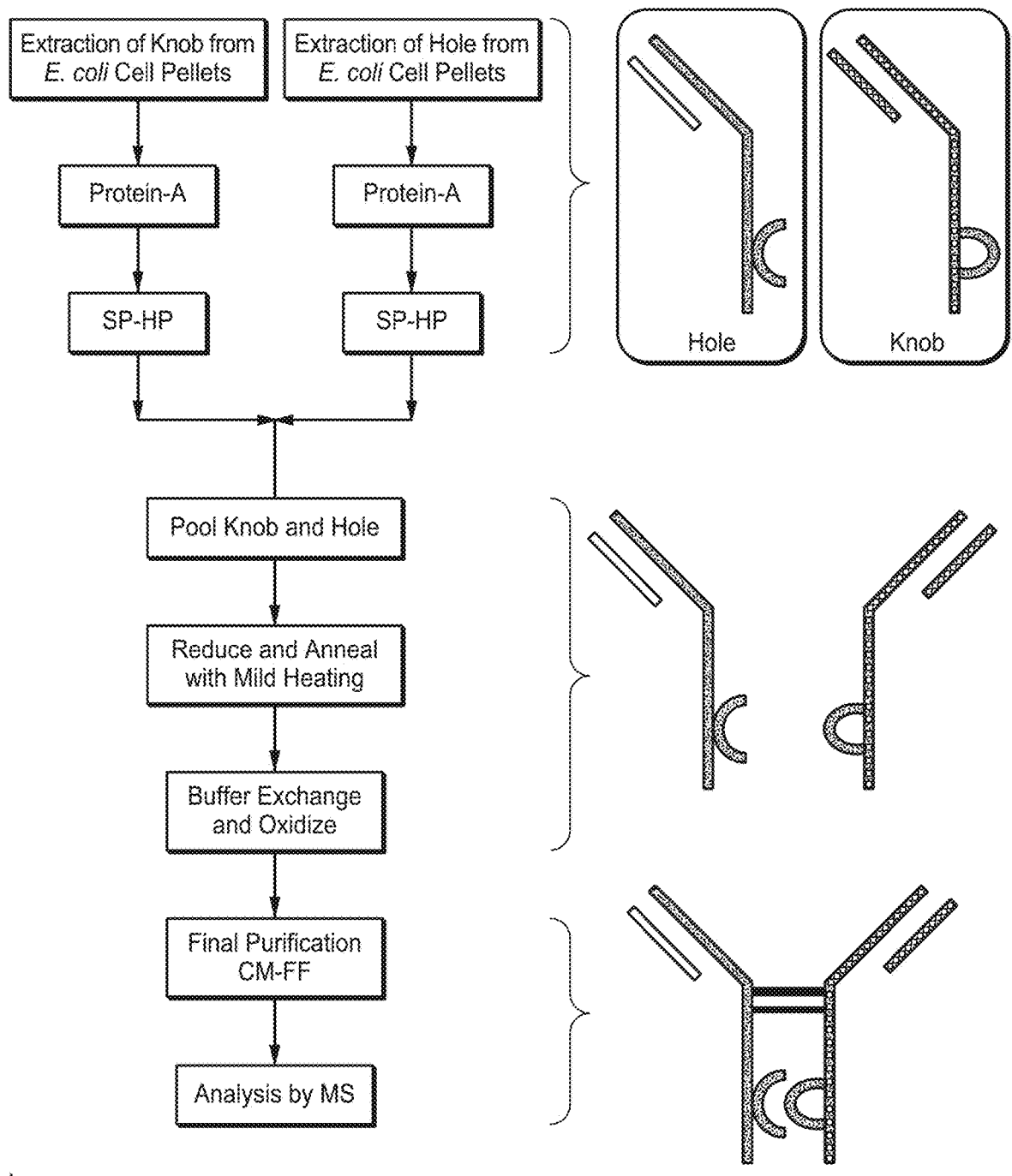
FIG. 4A is a flow diagram for the production of bispecific antibodies using separately engineered and expressed half-antibodies. In this method, redox chemistry is used.

Independent Production of Knob Half-Antibody and Hole Half-Antibody in Separate Cultures, Separate Purification of the Half-Antibodies, Mixing and Redox to Form Intact BsAb Half-antibodies containing either the knob or hole mutations (with or without the F241 and F243 mutations) were generated in separate cultures by expressing the heavy and light chains using the constructs described in Example 1 in a bacterial host cell, e.g., E. coli. See FIGS. 3 and 4A. In this method the knob half-antibody was an anti-EGFR and the hole half-antibody was an anti-c-met. The expression plasmids of Example 1 were introduced into E. coli host strains 33D3 (Ridgway et al. (1999) 59 (11): 2718) or 64B4 (W3110 ΔfhuA ΔphoA ilvG+Δprc spr43H1 ΔdegP ΔmanA lacI$^q$ ΔompT) and transformants were selected on carbenicillin containing LB plates. Transformants were then used to inoculate an LB starter culture containing carbenicillin, and this was grown overnight with shaking at 30° C. The starter culture was diluted 100× into a phosphate limiting media C.R.A.P. (Simmons et al., 2002, J. Immunol Methods, 263:133-147) containing carbenicillin, and this was grown for 24 hours with shaking at 30° C. The cultures were centrifuged, and the cell pellets frozen until the start of antibody purification. The pellets were thawed and resuspended in an extraction buffer containing 25 mM Tris-base adjusted to pH 7.5 with hydrochloric acid, 125 mM NaCl and 5 mM EDTA (TEB or Tris Extraction Buffer) with a volume to weight ratio of 100 mL TEB per 5 grams of cell pellet, and extracted by disrupting the cells using microfluidics by passing the resuspended mixture through a Microfluidics Corporation model 110F microfluidizer (Newton, Mass.) three times. The bacterial cell extract was then clarified by centrifugation for 20 minutes at 15,000×g and the supernatant collected and filtered through a 0.22 micron acetate filter prior to purification.

Figure 4B:
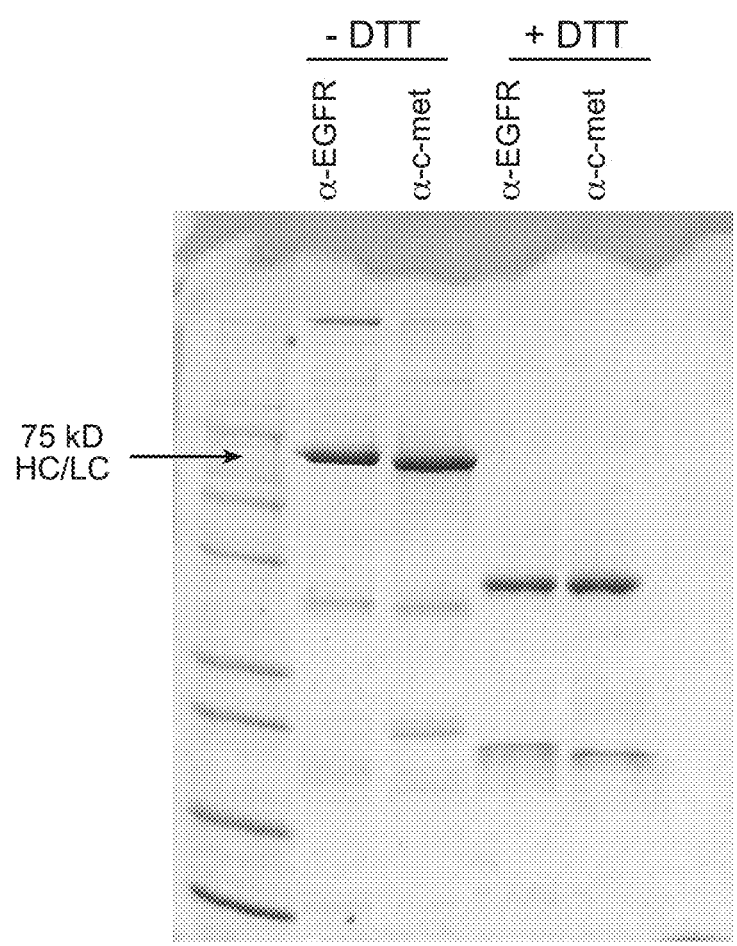
FIG. 4B shows a Coomassie stained gel. The two half-antibodies were analyzed under reducing and non-reducing conditions by SDS-PAGE. The predominant fraction is the 75 kD light chain-heavy chain pair for each half-antibody under non-reducing conditions. Under reducing conditions (e.g., treatment with DTT) each chain is visible as a separate band.
Figure 4C:
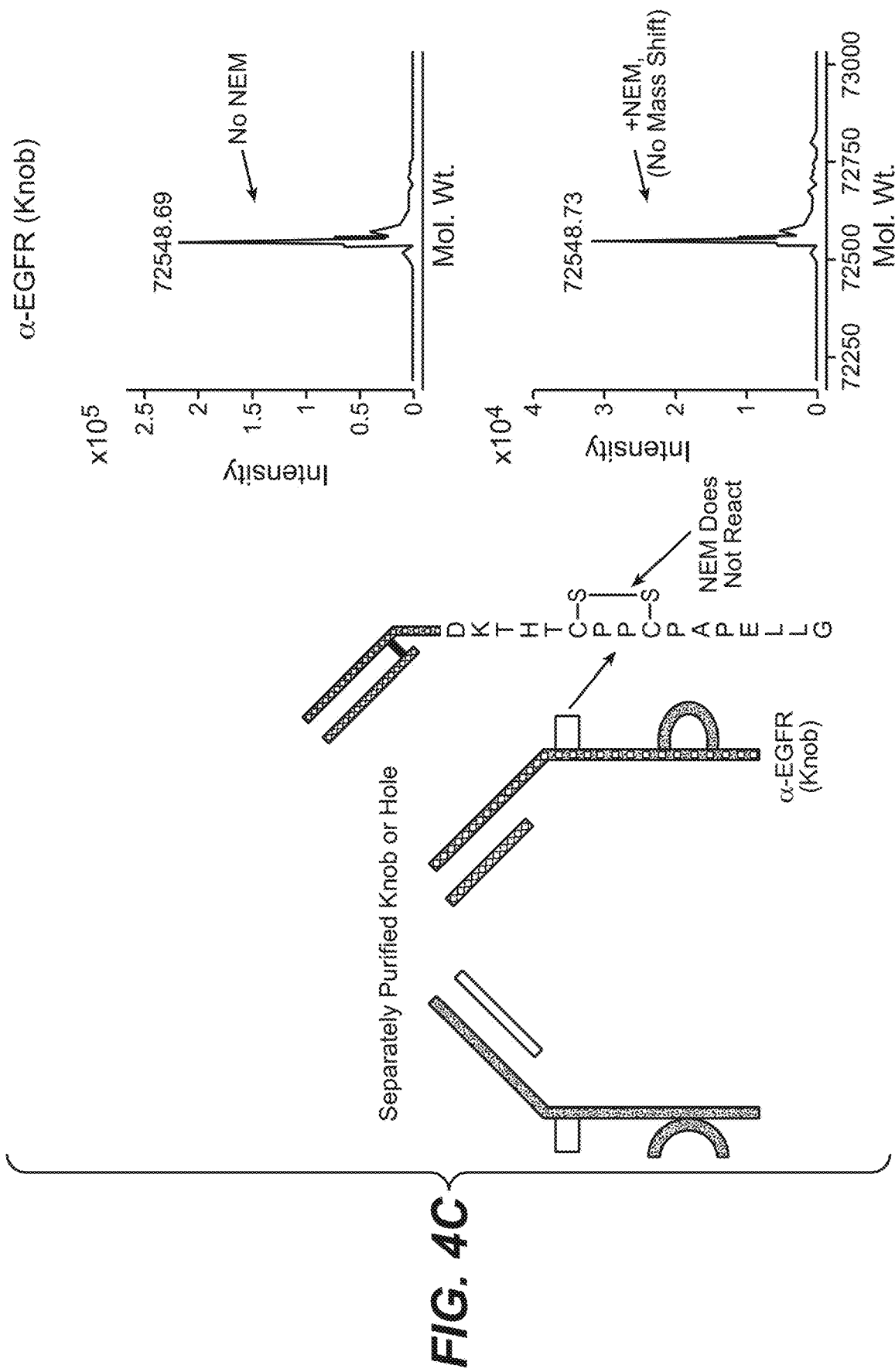
FIG. 4C shows the results of ESI-TOF mass spectrometry of a half-antibody with and without 1 mM N-ethylmaleimide (NEM) treatment. No change in the mass of the half-antibody is observed upon treatment with NEM indicating that all cysteines are fully oxidized. The oxidized hinge cysteines are represented as a cyclic disulfide in the depicted amino acid sequence. The expected mass for the half-antibody is 72,548 Daltons, which is what is observed by mass spectrometry indicating no covalent adducts. The amino acid sequence DKTHTCPPCPAPELLG is SEQ ID NO:5.

Each half-antibody was purified separately by Protein A capture followed by cation exchange chromatography. Clarified cell extracts from the knob half-antibody were loaded onto a 1 mL HiTrap MabSelect™ SuRe column from GE Healthcare (Pistcataway, N.J.) at 2 mL/min. After loading the column was washed with 10 column volumes (CV) of 40 mM sodium citrate, pH 6.0, 125 mM sodium chloride, and 5 mM EDTA followed by 5 column volumes of 20 mM sodium citrate at pH 6.0 to facilitate capture by the cation exchange column. The affinity captured half-antibodies were eluted with 10 column volumes (CV) of 0.2 mM acetic acid (pH 2-3) and directly captured on a 1 mL HiTrap SP-HP strong cation exchange column from GE Healthcare. The column was washed with 10 CV of buffer A containing 25 mM 2-(N-morpholino)ethanesulfonic acid (MES) pH 5.8. The half-antibodies were eluted with a linear gradient of 0-50% buffer B (25 mM MES, pH 5.8 and 1 M sodium chloride (NaCl)). Both proteins eluted between 20-40% B and the eluant peak as determined by UV absorbance at 280 nm and by non-reducing SDS-PAGE analysis of the collected fractions were pooled separately as the knob or hole half-antibody. Both proteins generally exhibited a major elution peak and all fractions that contained heavy chain and light chain species that were oxidized to one another were included in the pool. Analysis of the purified half-antibodies by reducing and non-reducing SDS-PAGE are shown in FIG. 4B. The results indicate that most of the expressed and captured protein is 75 kD in size. We confirmed this by ESI-TOF mass spectrometry shown in FIG. 4C. The mass of the half-antibodies were the expected masses indicating that there were no disulfide adducts on any cysteine, including the two cysteine residues in the hinge region. To determine if the hinge cysteines were reduced exhibiting a reactive free thiol, the proteins were reacted in at a neutral pH with 1 mM N-ethylmaleimide (NEM) for one hour before analysis by mass spectrometry. The mass of the protein was unchanged indicating that the hinge cysteines were oxidized to each other most likely in an intrachain disulfide, e.g., a cyclic disulfide. In order to assemble a fully intact, bispecific antibody using these two half-antibodies (knob and hole), it was necessary to first reduce the intrachain disulfides at the hinge region to liberate the cysteine free thiols so that they could subsequently be oxidized to the other heavy chain to form the 150 kD bispecific antibody.

Figure 5:
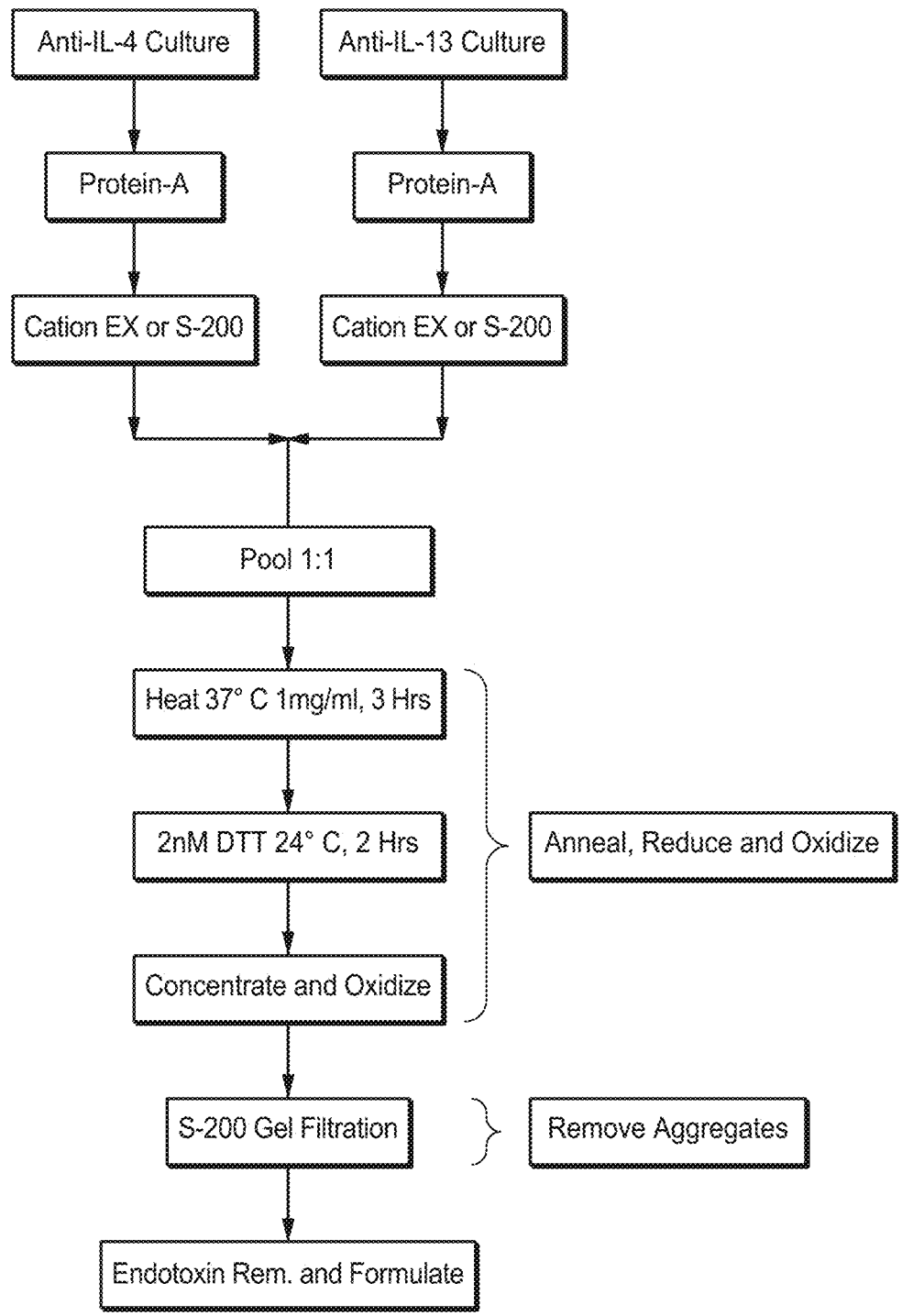
FIG. 5 is a flow diagram for the large scale production of bispecific antibodies using separately engineered and expressed half-antibodies.
Figure 6:
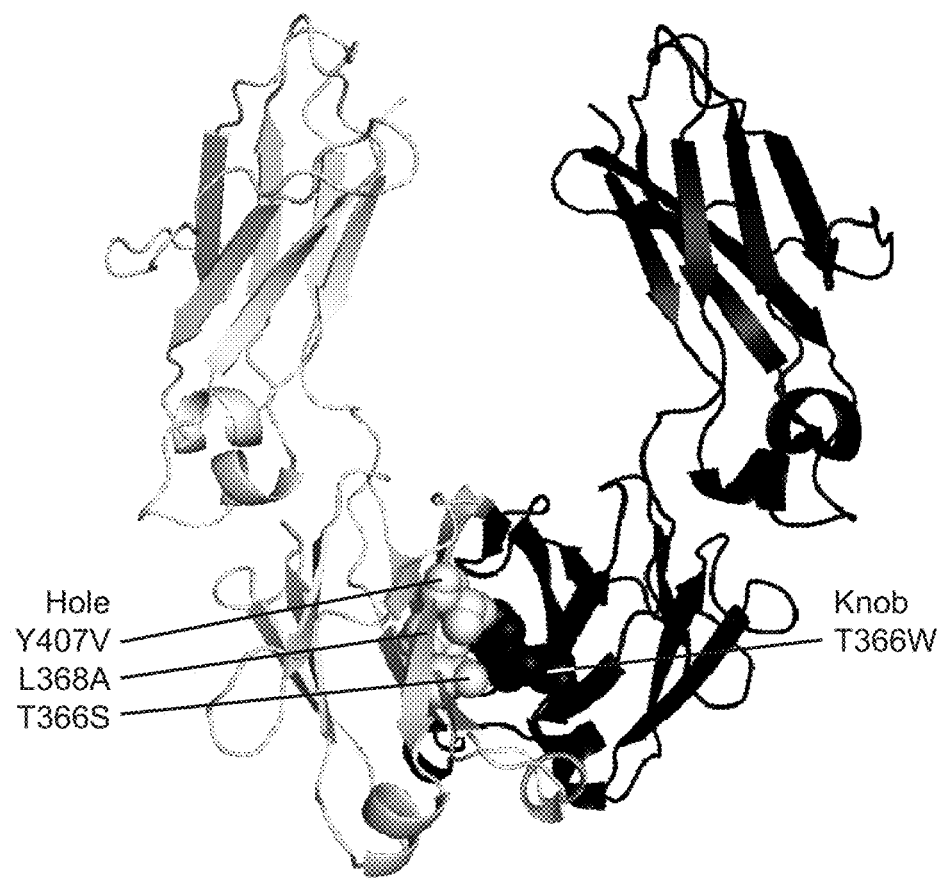
FIG. 6 is a graphic representation of the knob-into-holes Fc heterodimer. The heterodimer was crystallized in the presence of a mini-Z domain peptide (not shown). The mini-Z peptide was bound to the $C_H2$-$C_H3$ interface and presumably helps stabilize the $C_H2$ regions of the Fc. The knob and hole structure makes contact with the two $C_H3$ domains and is not significantly different from aglycosylated wild-type $IgG_1$ Fc's.

To accomplish the annealing, reduction and reoxidation of the two complementary half-antibodies to form the intact bispecific molecules the following procedure was developed. After independent isolation, the purified proteins were combined together at equal mass in the Pool step of the procedure (shown in FIG. 5), the pH of the pool was adjusted to 8.0 by adding one-tenth volume of 1 M Tris, pH 8.0, and proteins were reduced with 2.0 mM dithiothreitol (DTT) at room temperature. After reduction for 2 hours the pooled proteins were buffer exchanged into 25 mM Tris, pH 8.0, and 125 mM NaCl using 5 mL Zeba Desalt spin columns (Pierce, Rockford, Ill.) resulting in a volume of about 4 mLs of a protein concentration of 1 mg/mL. The proteins were then annealed by heating the mixture to 37° C. for 3 hours followed by cooling to room temperature, about 24° C. The annealed antibodies were concentrated using 10 kD MW cutoff spin concentrators to a volume of 0.5 mL with a protein concentration of about 10 mg/mL and oxidized by air while being dialyzed into 50 mM Tris pH 8.0, and 150 mM NaCl with 10 kD membranes (SpectrumLabs, Rancho Dominguez, Calif.). After oxidation overnight at room temperature, the oxidized material was run on an S-200 gel filtration column (22 mL S200 Tricorn from GE Healthcare) in a buffer containing 25 mM MES pH 6.0 and 300 mM NaCl. The intact antibody was pooled and diluted 10-fold in water.

The BsAb protein was then purified by weak cation exchange chromatography using a carboxymethyl (CM) resin (1 mL HiTrap CM-FF, GE Healthcare) with a pH gradient elution from 4.5 to 9.2. The buffer A and B composition consisted of 20 mM sodium citrate, 30 mM MES, 20 mM HEPES, 20 mM imidizole, 20 mM Tris, 20 mM CAPS, and 25 mM NaCl, where the A buffer is adjusted to pH 4.2 with HCl and the B buffer is adjusted to pH 9.2 (or 10.4) using NaOH. The purified material obtained after CM chromatography was analyzed by mass spectrometry to determine the exact molecular composition (FIG. 4D). Mass spec analysis indicated that the only detectable intact antibody product was with a MW of 146,051.89, which matches nearly identically with the heterodimeric knob-hole species anti-EGFR/anti-c-met with a theoretical MW of 145,051.75. The yield of this procedure, beginning with about 2 mg of the knob and 2 mg of the hole was about 0.5-1 mg.

The same procedure was performed for the half-antibodies containing the F241 and F243 mutations.

Example 3

Crystallization of Fc

During the assembly process, certain losses are associated with misformed disulfide bonds as demonstrated by the low yields in Example 2. This example is an analysis of different structural forms of the knob and hole Fc observed by X-ray crystallography. The Fc crystal structure was obtained for various heteromultimeric proteins, with only the knob and hole mutations described above.

Knob and Hole Fc for Crystallography

A one-armed knob-into-hole antibody consisting of an IgGI heavy chain (hole), one light chain, and one truncated heavy chain Fc (knob) was purified from *E. coli* using standard antibody purification methods. See, for example, WO2005/063816. The purified one-arm-antibody was digested with a 1/1000 wt/wt ratio with lysine endopeptidase-C for 15 minutes at 37° C. The digest was stopped with 5 µM of the protease inhibitor N-alpha-tosyl-L-lysinyl-chloromethylketone (TLCK). Intact one-arm-antibody and FAb were removed from the knob-hole Fc using kappa select resin which did not bind free Fc. The knob/hole Fc was then purified over an S75 column (GE Biosciences) prior to crystallization. The resulting knob and hole Fc fragments have the following sequences (the starting residue number based on a full length IgG1 heavy chain is provided):

Crystallization conditions required the addition of a miniZ domain from protein A (Starovasnik reference below) to stabilize the protein. Protein was buffer exchanged into 0.15M NaCl, 50 mM Tris pH 8.0 and concentrated to 15 mg/mL. Equimolar concentration Mini-Z peptide was added and incubated overnight. Proteins were crystallized by hanging drop method (See, for example, Experimental and theoretical analysis of the rate of solvent equilibration in the hanging drop method of protein crystal growth. Journal of Crystal Growth, volume 90, Issues 1-3, 2 Jul. 1988, pages 117-129) at 18° C. with a buffer reservoir containing 20% w/v PEG2000-MME, 0.1 M MES pH 6.5, 10% v/v isopropanol. Blades of protein formed after 1 week. Data was collected at the ALS beamline 5.0.2.

The minimized version of the Protein A, B-domain ("miniZ") was prepared as previously described (Starovasnik M. A., Braisted A. C., Wells J. A. (1997) *Proc. Natl. Acad. Sci. USA Vol.* 94, pp. 10080-10085).

The knob-into-holes Fc heterodimer was crystallized in the presence of a mini-Z domain peptide (as described above). See FIG. 6. The mini-Z peptide was bound to the CH2-CH3 interface and presumably helps stabilize the CH2 regions of the Fc. The structure makes contact with the two CH3 domains and is not significantly different from aglycosylated wt IgG1 Fc's.

Knob Knob Fc for Crystallography:

Knob-knob protein dimer was produced by expression in *E. coli* as described above except Fc variants were expressed as single Fc chains with hinge cysteines removed by mutation to serine to prevent covalent dimerization (see, for example, WO2006028936) and the cation exchange step was omitted. The knob-knob Fc was present as a non-covalent dimer and isolated by a combination of Protein A affinity chromatography and gel filtration using an S200 column (GE Biosciences). The purified protein was used for crystal screening. For crystal growth screens, the protein was buffer exchanged into PBS and concentrated to 10 mg/mL. The protein crystallized in 20% w/v PEG2000-monomethylether (MME), 0.2 M Ammonium sulfate, 0.1 M Sodium cacodylate pH 6.5 with 2 µl of protein in 2 µl of reservoir by the hanging drop method at 18° C. Thick blades appeared after five days and the data were collected at the ALS beamline 5.0.1. using a cryoprotectant of 25% w/v PEG 2000-MME.

```
Chain1 (hole)
                                                     (SEQ ID NO: 1)
223 THTCPPCPAP ELLGGPSVFL FPPKPKDTLM ISRTPEVTCV VVDVSHEDPE

VKFNWYVDGV EVHNAKTKPR EEQYNSTYRV VSVLTVLHQD WLNGKEYKCK

VSNKALPAPI EKTISKAKGQ PREPQVYTLP PSREEMTKNQ VSLSCAVKGF YPSDIAVEWE

SNGQPENNYK TTPPVLDSDG SFFLVSKLTV DKSRWQQGNV FSCSVMHEAL

HNHYTQKSLS LSPGK

Chain2 (knob)
                                                     (SEQ ID NO: 2)
221 DKTHTCPPCP APELLGGPSV FLFPPKPKDT LMISRTPEVT CVVVDVSHED

PEVKFNWYVD GVEVHNAKTK PREEQYNSTY RVVSVLTVLH QDWLNGKEYK

CKVSNKALPA PIEKTISKAK GQPREPQVYT LPPSREEMTK NQVSLWCLVK GFYPSDIAVE

WESNGQPENN YKTTPPVLDS DGSFFLYSKL TVDKSRWQQG NVFSCSVMHE

ALHNHYTQKS LSLSPGK
```

The sequence for the knob sequence was (SEQ ID NO: 3):

```
221 DKTHTSPPSP APELLGGPSV FLFPPKPKDT LMISRTPEVT CVVVDVSHED

PEVKFNWYVD GVEVHNAKTK PREEQYNSTY RVVSVLTVLH QDWLNGKEYK

CKVSNKALPA PIEKTISKAK GQPREPQVYT LPPSREEMTK NQVSLWCLVK GFYPSDIAVE

WESNGQPENN YKTTPPVLDS DGSFFLYSKL TVDKSRWQQG NVFSCSVMHE

ALHNHYTQKS LSLSPGK
```

The hole/hole homodimer was prepared in the same manner as the knob/knob Fc variants above.

The sequence for the hole sequence was (SEQ ID NO:4):

```
221 DKTHTSPPSP APELLGGPSV FLFPPKPKDT LMISRTPEVT CVVVDVSHED

PEVKFNWYVD GVEVHNAKTK PREEQYNSTY RVVSVLTVLH QDWLNGKEYK

CKVSNKALPA PIEKTISKAK GQPREPQVYT LPPSREEMTK NQVSLSCAVK GFYPSDIAVE

WESNGQPENN YKTTPPVLDS DGSFFLVSKL TVDKSRWQQG NVFSCSVMHE

ALHNHYTQKS LSLSPGK
```

Figure 7:
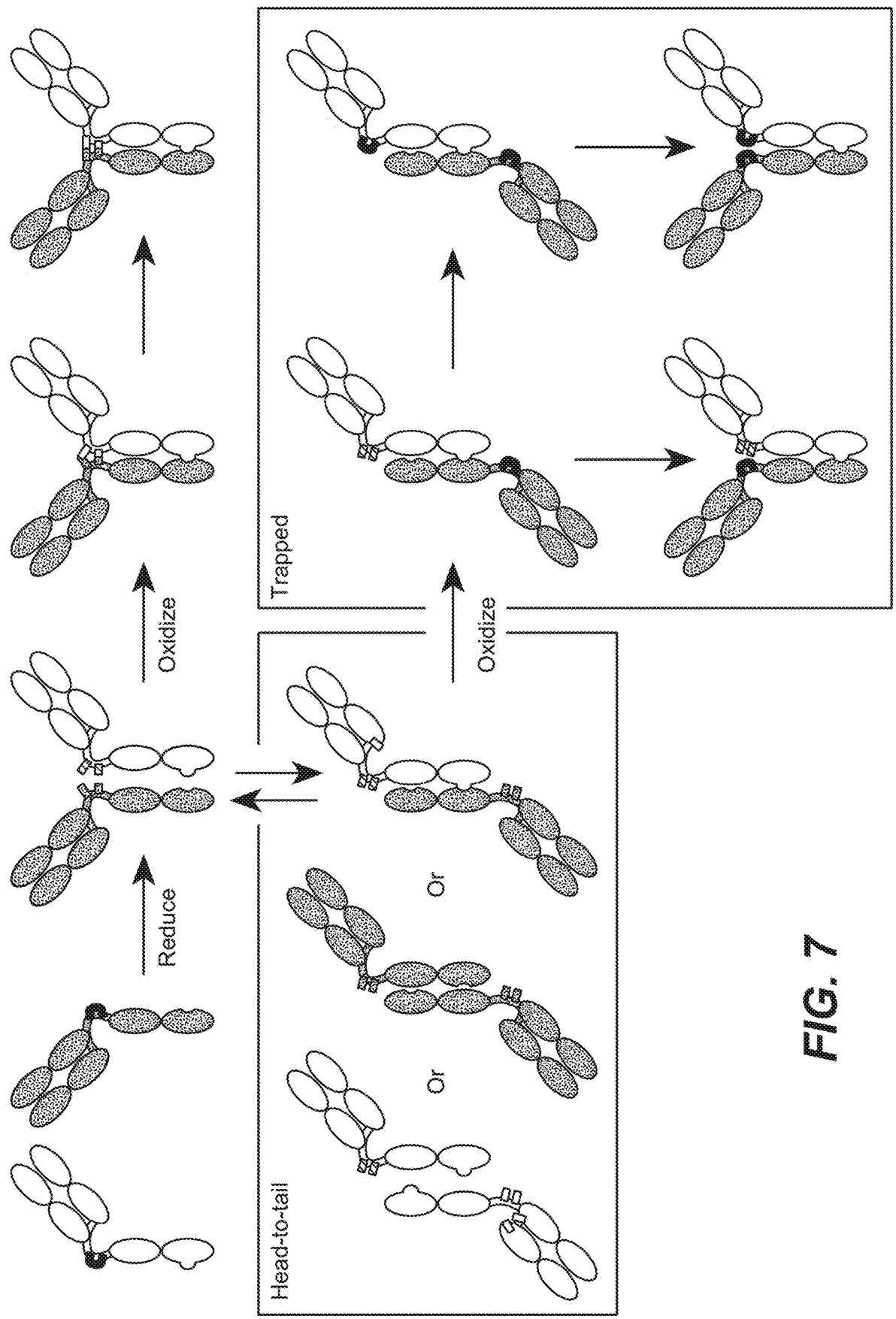
FIG. 7 is a graphic representation of head-to-tail pairings suggested by Fc crystal structure analysis. The pairings may be partially responsible for redox inefficiency. The Head-to-tail pairing of the Fc's cause a portion of the antibodies to escape hinge disulfide pairing. Though dimeric, the uncertainty of their true identity requires their removal. This impacts the overall yields/efficiency of the annealment process and remains a target for platform improvement.
Figure 9A:
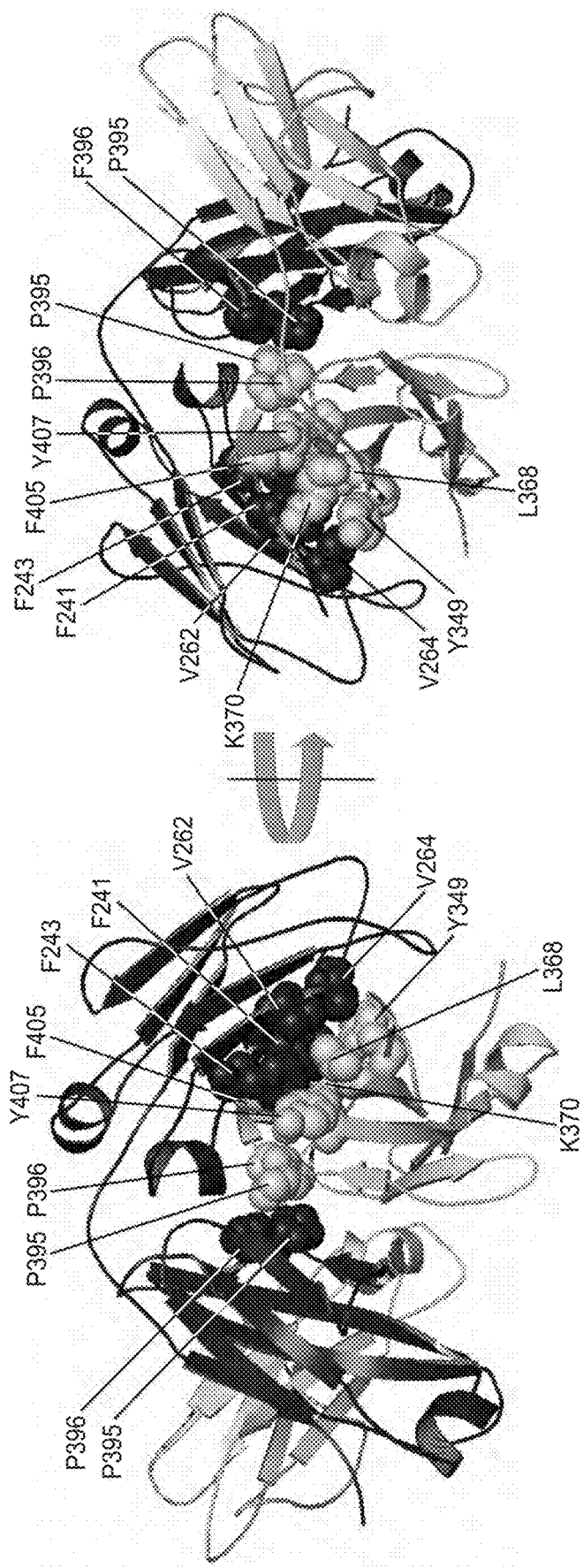
FIGS. 9A and 9B show the contact regions between the Knob-Knob Fcs.
Figure 9B:
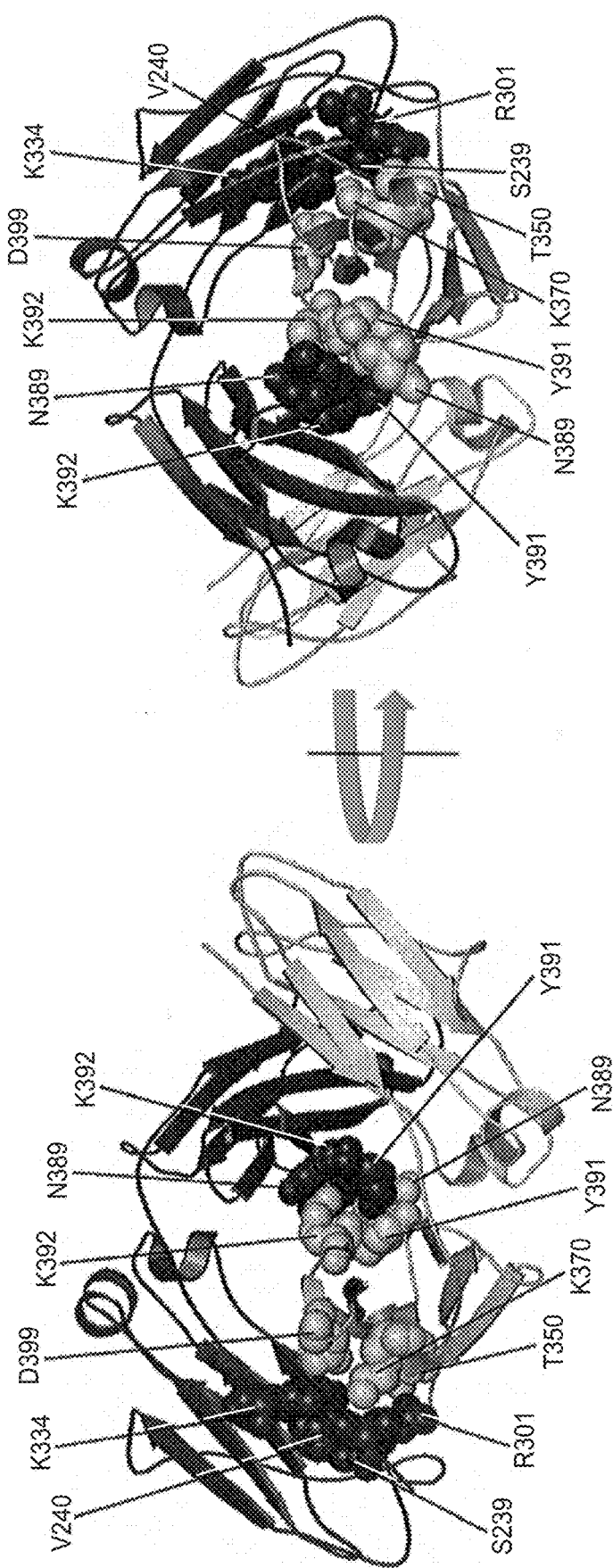

The homodimeric Fc's, however, formed a head to tail conformation which would present either of the bispecific's Fabs 180° from one another as depicted in FIG. 7. Not only would this be a novel conformation for an Fc, it would also prevent normal hinge oxidation as the disulfide pairs are on opposite ends of the Fc. Without a matching Fc the hinge cysteines tend to cyclize and then are unreactive unless redoxidized. Thus, these structures suggest alternative conformations which may contribute to redox inefficiency.

Table 1 shows the Data Collection and Refinement for homodimers—knob/knob and hole/hole—and the heterodimer—knob/hole. Based on the crystal structure analysis the following Table 3 of contact residues was developed:

TABLE 3

| Chain A | Chain B |
| --- | --- |
| S239 | K370 |
| V240 | K370 |
| F241 | L368 |
| F241 | K370 |
| F243 | F405 |
| F243 | Y407 |
| P244 | V397 |
| V264 | Y349 |
| R301 | T350 |
| K334 | D399 |
| Y349 | D265 |
| L368 | V262 |
| K392 | N389 |
| K392 | Y391 |
| P395 | P396 |

For clarity, Chain A and B have both sets of contacts. The above table represents one of two sets. So a complete table would have double the contacts listed above. For example S239 in A contacts K370 in B, and S239 in B makes contact with K370 in A.

Example 4

Orientation Stabilization

The limiting step during annealing and purification is the redox step. Oxidized heterodimer typically only makes up 70-80% of the protein after this step (BioAnalyzer and MS-TOF). The remaining 20-30% of antibody is dimeric and lacks a covalent linkage (SEC-LLS). This can be removed but significantly impacts overall yields. Thus, to test if we can disrupt the head-to-tail associations, and thus improve bispecific recoveries, we generated knob Fcs with F241 S/F243R or F241R/F243S mutations.

Knob and hole Fc's have approximately the same amount of homodimer by size exclusion chromatography. Mutations to the knob Fc reduced the amount of homodimer present when compared to wild-type (i.e., only the knob mutations) by as much as 83.5% (see FIG. 8). See Table 4 below.

TABLE 4

|  | Knob F241S/F243R | Knob F241R/F243S |
| --- | --- | --- |
| Reduction in homodimer content | 83.5% | 64.5% |

Annealing of the knob and hole bispecific antibody is improved with the Fc mutants compared to the wild-type knob. The percent of intact antibody quantified by bioanalyzer is 27.6% for the wt pair, 46.4% for the F241 S/F243R mutant knob, and 45.5% for the F241R/F243S mutant knob. Making either F241 S/F243R or F241R/F243S mutations disrupt the hydrophobic centers of head-to-tail pairing. The incorporation of the mutations in the knob chain decreased the amount of homodimer relative to the wild-type knob and appears to be beneficial for yield improvement. It is believed that similar mutations in a wild-type hole alone or in the wild-type knob-into-hole Fc would result in similar improvements.

Glutathione Bispecific Time Course

Figure 10:
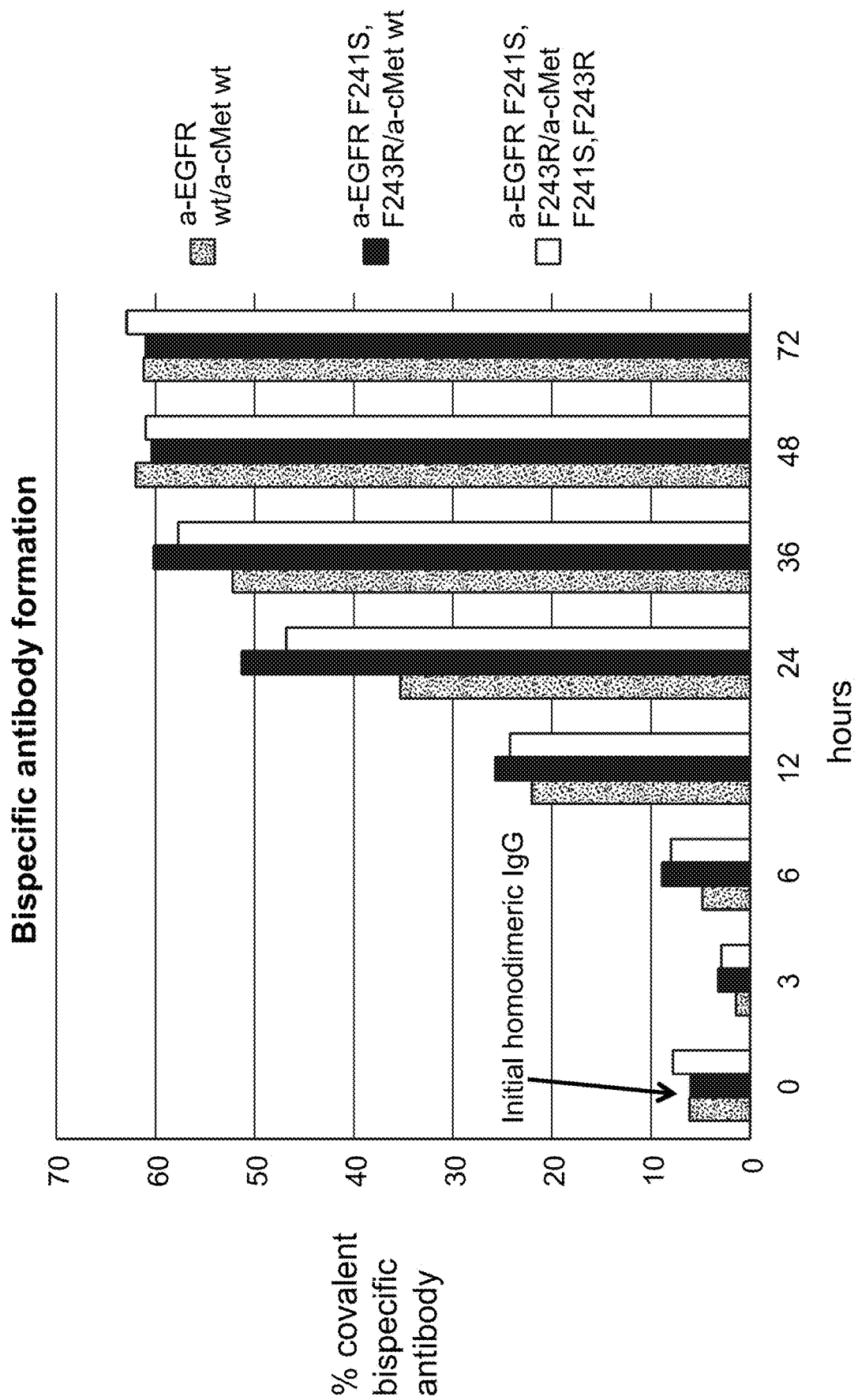
FIG. 10 is a bar graph showing the rate of disulfide formation to yield the correct knob-into-hole heterodimer. When the half-antibodies are initially mixed together a low level of homodimers are seen at time zero. As the reduced glutathione begins reducing the hinge disulfides, the homodimers begin to disappear. As the time course progresses the glutathione begins the oxidation process and an increase in intact IgG formation is seen.
Figure 11A:
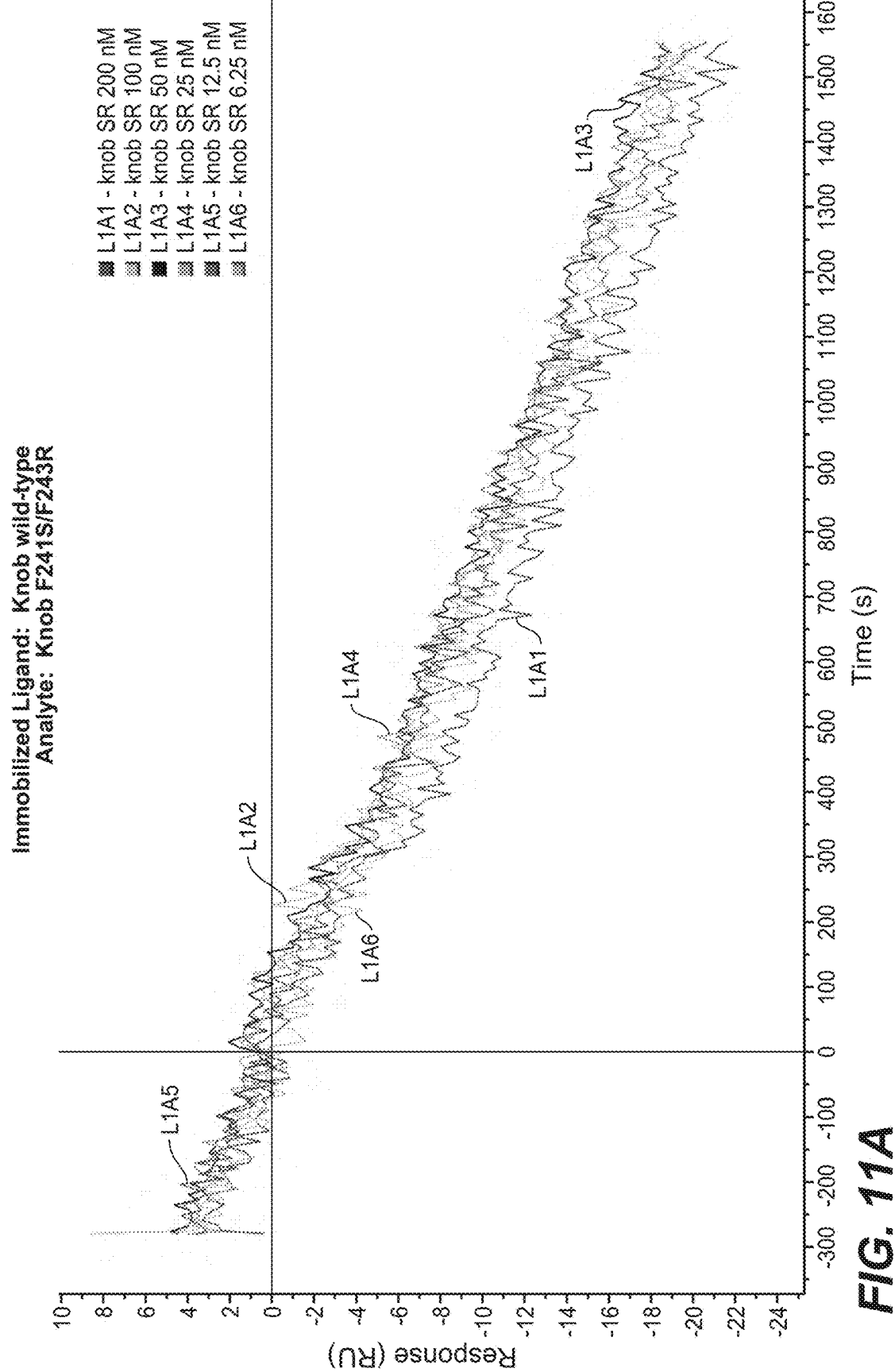
FIGS. 11A-11E area series of the surface plasmon resonance (SPR) spectra curves from experiments using an immobilized ligand. The analyte was passed over the ligand and the homodimerization was monitored. Analyte concentrations were tested at 6.25 nM, 12.5 nM, 25 nM, 50 nM, 100 nM and 200 nM. The ligands were: (A) The knob wild-type, (B) hole wild-type, (C) knob F241R/F243S, (D) knob F241 S/F243R, and (E) hole F241S/F243R. The y-axis shows the response units and the x-axis is time (seconds).
Figure 11B:
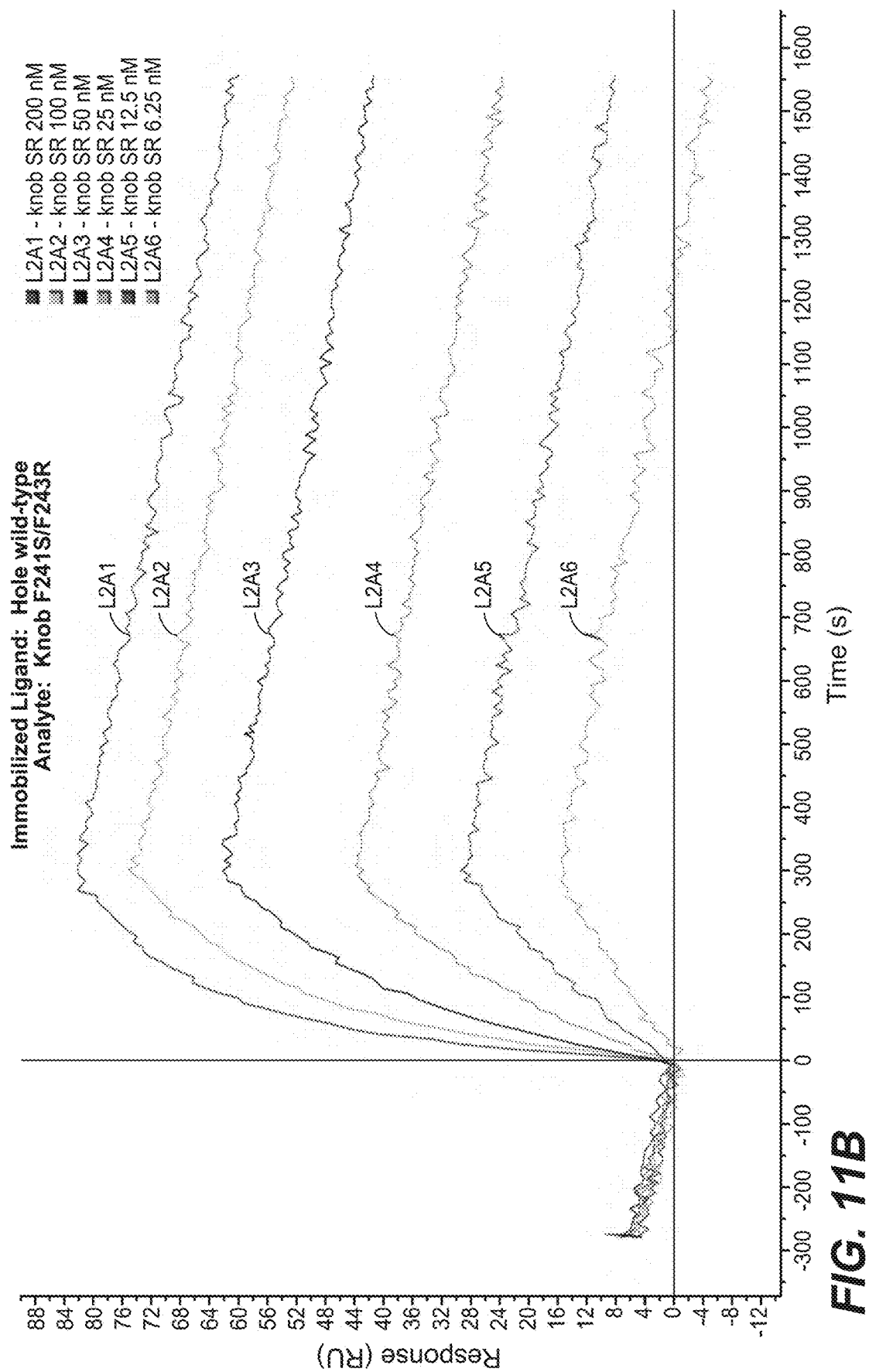
Figure 11C:
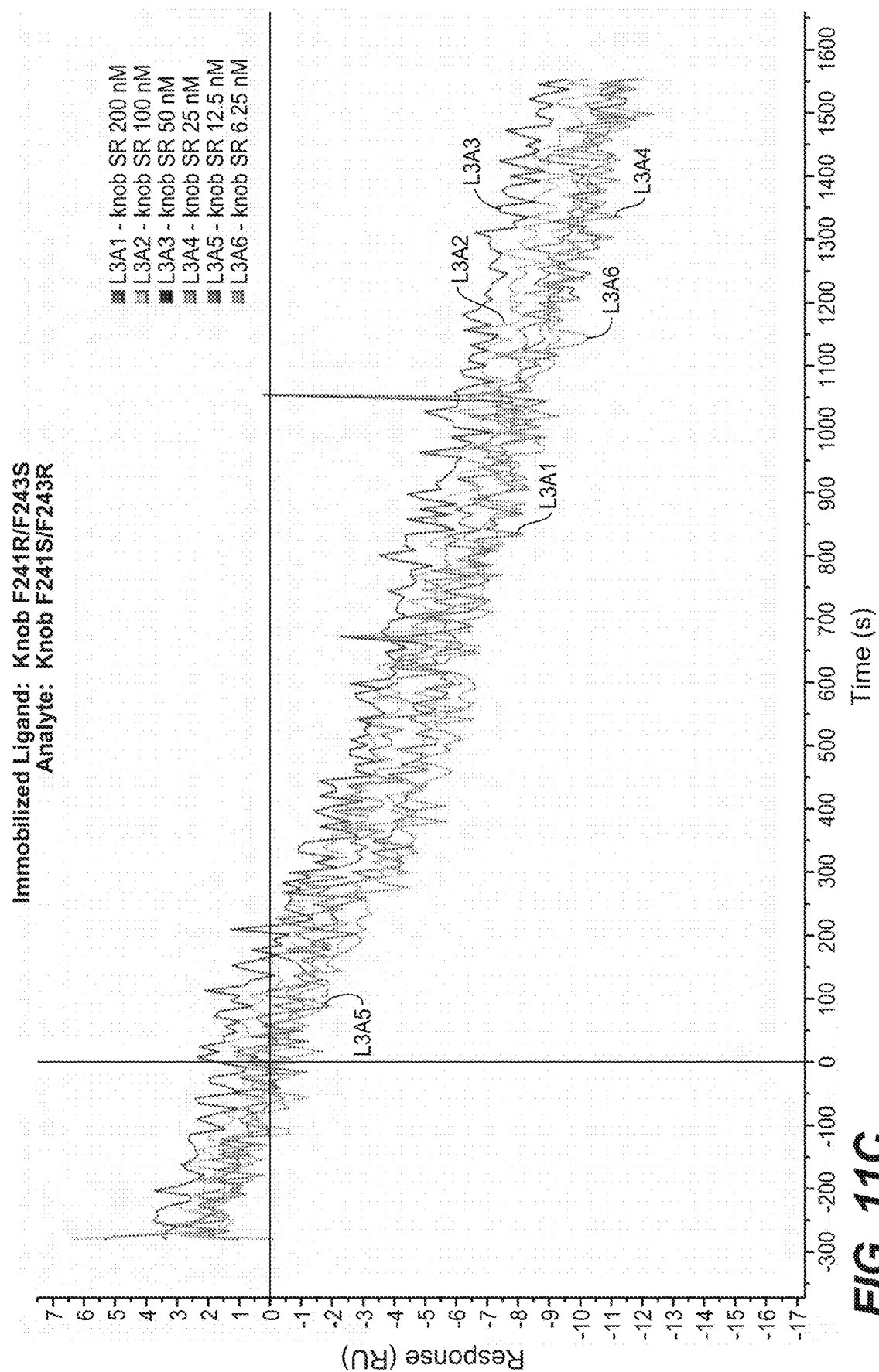
Figure 11D:
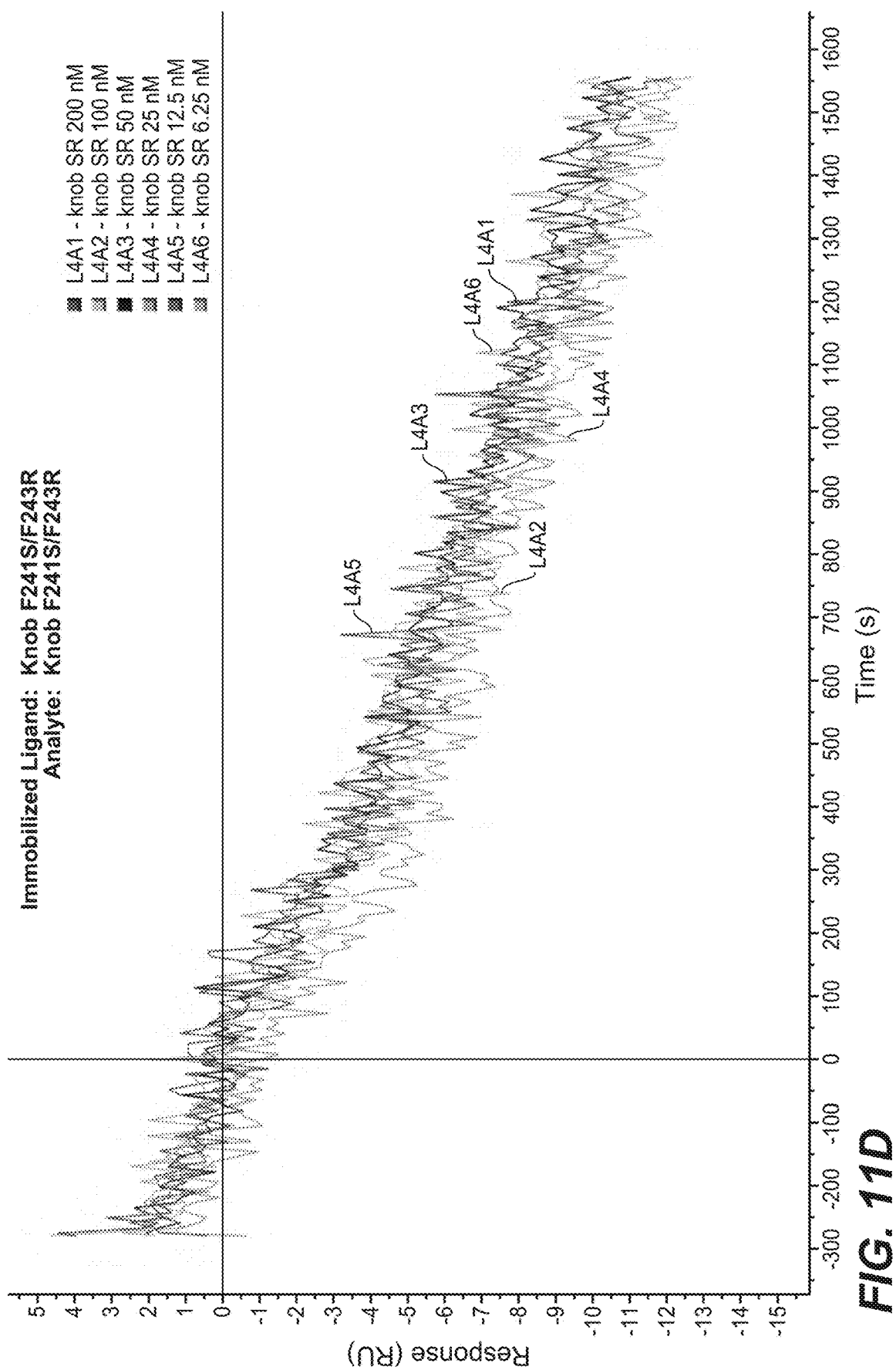
Figure 11E:
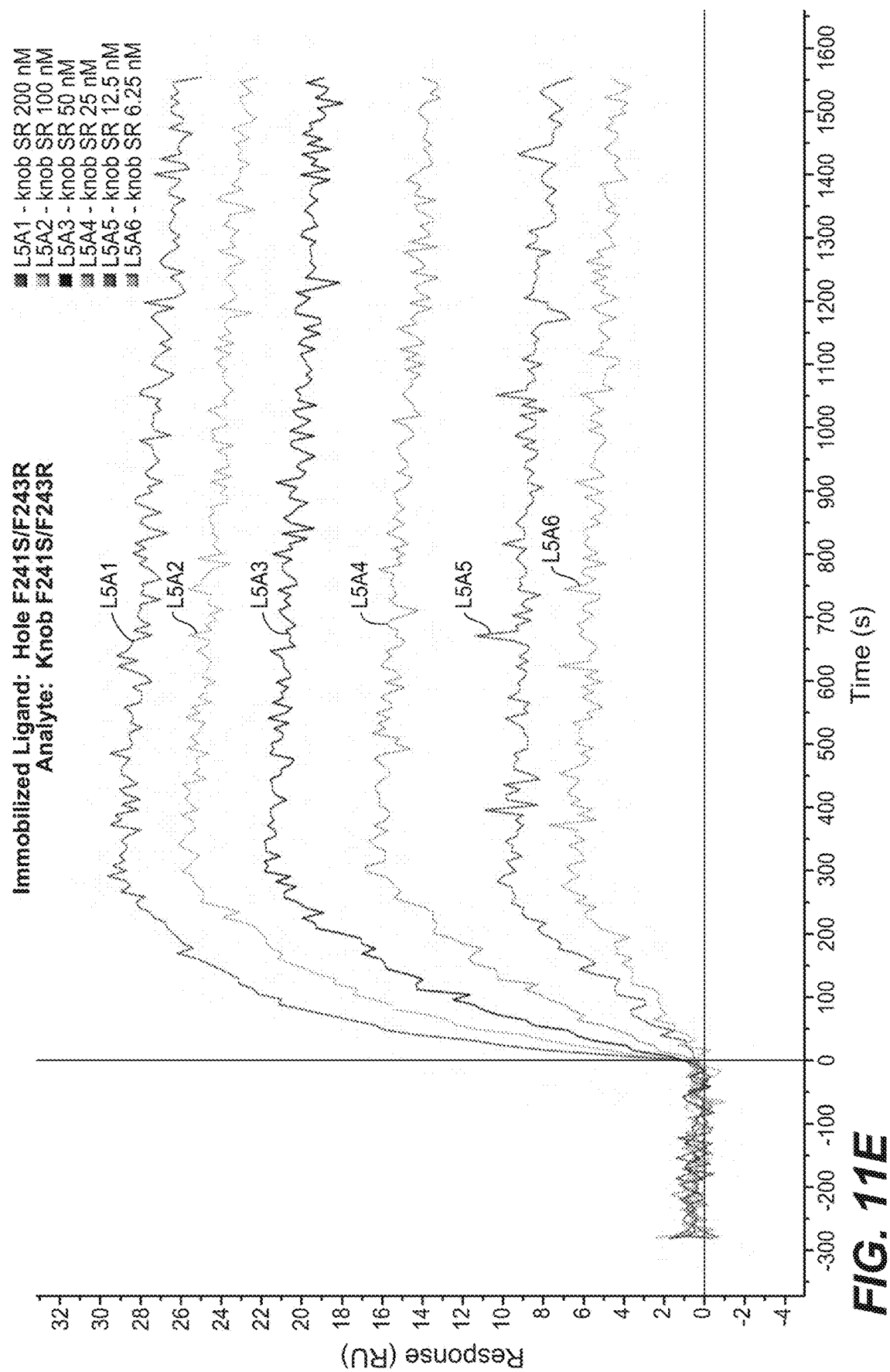

F241 S/F243R mutations increased the rate of correct disulfide formation between bispecific antibodies. Half antibodies were mixed 1:1 in 200 mM Arginine succinate pH8.5 with 200 molar excess reduced glutathione at room temperature. During the reaction samples were taken at the following time points: 0, 3 hrs, 6 hrs, 12 hrs, 24 hrs, 36 hrs, 48 hrs, and 72 hrs. Upon collection, an equivalent volume of 0.15 M acetic acid was added to stop the assembly reaction. Samples were then analyzed on an Agilent BioAnalyzer 2100 with a Protein 230 kit. Utilizing the F241 S/F243R mutations either on knob and/or hole half antibodies increases the rate of oxidation under these conditions in the 12 to 48 hour time frames (FIG. 10). This demonstrates the advantage of these mutants for increasing assembly rates and overall assembly efficiency.

Knob and Hole Associations Via Surface Plasmon Resonance (SPR)

Using a BioRad ProteOn™ system, knob wild-type, hole wild-type, knob F241R/F243S, knob F241 S/F243R, and hole F241 S/F243R ligands were immobilized on an NHS activated sensor. The analyte, knob F241 S/F243R, was passed over the sensor in 25 mM Tris 150 mM NaCl 0.05% Tween-20 pH 8.0. Analyte concentrations were 200 nM, 100 nM, 50 nM, 25 nM, 12.5 nM, and 6.25 nM. The ProteOn™ chip was regenerated between each analyte concentration using 10 mM Glycine pH3. The data demonstrated that the F241/F243 mutations do not interfere with CH3 heterodimerization, nor is there any measurable homodimerization with or without these changes at these concentrations (FIGS. 11A-E). The Kd for the heterodimers is in the single digit nanomolar range in both cases.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A heteromultimeric protein or an IgG antibody, wherein the heteromultimeric protein or the IgG antibody each comprises an Fc region comprising substitution mutations at residues 241 and 243 on at least one heavy chain, wherein said substitution mutations are selected from the group consisting of (a) F241R and F243 S and (b) F241S and F243R, wherein numbering is according to the EU numbering scheme, wherein no amino acid residue of any Fc polypeptide of the heteromultimeric protein or the IgG antibody is glycosylated, and wherein said heteromultimeric protein or IgG antibody exhibits decreased mispairing, decreased head-to-tail formation or increased overall yield as compared to a heteromultimeric protein or an IgG antibody without said amino acid substitution mutations at residues 241 and 243.

2. The heteromultimeric protein or the IgG antibody of claim 1, wherein both heavy chains comprise the F241R and F243 S or the F241S and F243R substitutions.

3. A composition comprising the heteromultimeric protein or the IgG antibody of claim 1 and a carrier.

4. The heteromultimeric protein or the IgG antibody of claim 1 wherein the Fc region is an IgG1 Fc region comprising the substitution mutations at residues 241 and 243 on at least one heavy chain, wherein said substitution mutations are selected from the group consisting of (a) F241R and F243S and (b) F241S and F243R.

5. The heteromultimeric protein or the IgG antibody of claim 1, wherein the Fc region further comprises at least one knob-into-hole modification at amino acid residues other than residues 241 and 243, wherein numbering is according to the EU numbering scheme.

6. The heteromultimeric protein or the IgG antibody of claim 5, wherein the at least one knob-into-hole modification comprises a knob modification comprising a T366W substitution, wherein numbering is according to the EU numbering scheme.

7. The heteromultimeric protein or the IgG antibody of claim 5, wherein the at least one knob-into-hole modification comprises a hole modification comprising replacing an original amino acid residue from the interface of the Fc region with an amino acid residue with a smaller side chain than the original amino acid residue, wherein the substituting amino acid residue is selected from the group consisting of serine, threonine, valine, and alanine.

8. The heteromultimeric protein or the IgG antibody of claim 7, wherein the hole modification comprises two or more amino acid substitutions selected from the group consisting of T366S, L368A and Y407V, wherein all numbering is according to the EU numbering scheme.

9. The heteromultimeric protein or the IgG antibody of claim 5, wherein the Fc region is an IgG1 Fc region comprising the substitution mutations at residues 241 and 243 on at least one heavy chain, wherein said substitution mutations are selected from the group consisting of (a) F241R and F243S and (b) F241S and F243R and comprising the at least one knob-into-hole modification.

10. The heteromultimeric protein or the IgG antibody of claim 1, which is an IgG antibody.

11. The IgG antibody according to claim 10, wherein the IgG antibody is a multi-specific antibody.

12. The IgG antibody of claim 10, wherein the IgG antibody comprises an IgG1 Fc region comprising the substitution mutations at residues 241 and 243 on at least one heavy chain, wherein said substitution mutations are selected from the group consisting of (a) F241R and F243S and (b) F241S and F243R.

13. An isolated heteromultimeric protein or an isolated IgG antibody produced by culturing a prokaryotic host cell comprising an expression vector encoding the heteromultimeric protein or the IgG antibody, and recovering the heteromultimeric protein or the IgG antibody from the cell culture, wherein the heteromultimeric protein or the IgG antibody each comprises an Fc region comprising substitution mutations at residues 241 and 243 on at least one heavy chain, wherein said substitution mutations are selected from the group consisting of (a) F241R and F243S and (b) F241S and F243R, wherein numbering is according to the EU numbering scheme, and wherein no amino acid residue of any Fc polypeptide of the heteromultimeric protein or the IgG antibody is glycosylated.

14. The heteromultimeric protein or the IgG antibody of claim 13 wherein the Fc region is an IgG1 Fc region comprising the substitution mutations at residues 241 and 243 on at least one heavy chain, wherein said substitution mutations are selected from the group consisting of (a) F241R and F243S and (b) F241S and F243R.

15. The heteromultimeric protein or the IgG antibody of claim 13, wherein the prokaryotic host cell is an *E. coli* cell.

16. The heteromultimeric protein or the IgG antibody of claim 14, wherein the prokaryotic host cell is an *E. coli* cell.

17. The heteromultimeric protein or the IgG antibody of claim 13, wherein the Fc region further comprises at least one knob-into-hole modification at amino acid residues other than residues 241 and 243, wherein numbering is according to the EU numbering scheme.

18. The heteromultimeric protein or the IgG antibody of claim 17, wherein the at least one knob-into-hole modification comprises a T366W substitution, wherein numbering is according to the EU numbering scheme.

19. The heteromultimeric protein or the IgG antibody of claim 17, wherein the at least one knob-into-hole modification comprises a hole modification comprising replacing an original amino acid residue from the interface of the Fc region with an amino acid residue with a smaller side chain than the original amino acid residue, wherein the substituting amino acid residue is selected from the group consisting of serine, threonine, valine, and alanine.

20. The heteromultimeric protein or the IgG antibody of claim 19, wherein the hole modification comprises two or more amino acid substitutions selected from the group consisting of T366S, L368A and Y407V, wherein all numbering is according to the EU numbering scheme.

21. The heteromultimeric protein or the IgG antibody of claim 13, wherein both heavy chains comprise the F241R and F243 S or the F241S and F243R substitutions.

22. The heteromultimeric protein or the IgG antibody of claim 13, which is an IgG antibody.

23. The IgG antibody of claim 22, wherein the IgG antibody comprises an IgG1 Fc region comprising the substitution mutations at residues 241 and 243 on at least one heavy chain, wherein said substitution mutations are selected from the group consisting of (a) F241R and F243S and (b) F241S and F243R.

24. The IgG antibody according to claim 22, wherein the IgG antibody is a multi-specific antibody.

25. The IgG antibody according to claim 5, wherein the at least one knob-into-hole modification comprises a knob modification comprising a T366W substitution and a hole modification comprising two or more amino acid substitutions selected from the group consisting of T366S, L368A and Y407V, wherein all numbering is according to the EU numbering scheme.

26. The IgG antibody according to claim 25, wherein the at least one knob-into-hole modification comprises a knob modification comprising a T366W substitution and a hole modification comprising T366S, L368A and Y407V substitutions, wherein all numbering is according to the EU numbering scheme.

* * * * *

```
SEQUENCE LISTING

<160> NUMBER OF SEQ ID NOS: 5

<210> SEQ ID NO 1
<211> LENGTH: 225
<212> TYPE: PRT
<213> ORGANISM: Homo sapiens

<400> SEQUENCE: 1

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Ser
    130                 135                 140

Cys Ala Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Val Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 2
<211> LENGTH: 227
<212> TYPE: PRT
<213> ORGANISM: Homo sapiens
```

```
<400> SEQUENCE: 2

Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 3
<211> LENGTH: 227
<212> TYPE: PRT
<213> ORGANISM: Homo sapiens

<400> SEQUENCE: 3

Asp Lys Thr His Thr Ser Pro Pro Ser Pro Ala Pro Glu Leu Leu Gly
  1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125
```

```
Tyr Thr Leu Pro Pro Ser Arg Glu Glu Met Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 4
<211> LENGTH: 227
<212> TYPE: PRT
<213> ORGANISM: Homo sapiens

<400> SEQUENCE: 4

Asp Lys Thr His Thr Ser Pro Pro Ser Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
            130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 5
<211> LENGTH: 16
<212> TYPE: PRT
<213> ORGANISM: Artificial Sequence
```

```
<220> FEATURE:
<223> OTHER INFORMATION: Synthetic Construct

<400> SEQUENCE: 5

Asp Lys Thr His Thr Cys Pro Pro Cys Pro Ala Pro Glu Leu Leu Gly
1               5                   10                  15
```